US012782338B2

(12) United States Patent
Pfeil

(10) Patent No.: US 12,782,338 B2
(45) Date of Patent: Nov. 3, 2026

(54) SYSTEM AND METHOD FOR DISCOVERING VALIDATING AND PERSONALIZING TRANSPOSABLE ELEMENT CANCER VACCINES

(71) Applicant: THE REGENTS OF THE UNIVERSITY OF CALIFORNIA, Oakland, CA (US)

(72) Inventor: Jacob Pfeil, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 1204 days.

(21) Appl. No.: 17/769,277

(22) PCT Filed: Oct. 19, 2020

(86) PCT No.: PCT/US2020/056344
§ 371 (c)(1),
(2) Date: Apr. 14, 2022

(87) PCT Pub. No.: WO2021/077094
PCT Pub. Date: Apr. 22, 2021

(65) Prior Publication Data

US 2024/0142436 A1 May 2, 2024

Related U.S. Application Data

(60) Provisional application No. 62/916,816, filed on Oct. 18, 2019.

(51) Int. Cl.

| | |
|---|---|
| ***C12Q 1/6874*** | (2018.01) |
| ***C12Q 1/6886*** | (2018.01) |
| ***G01N 33/50*** | (2006.01) |
| ***G01N 33/575*** | (2026.01) |
| ***G01N 33/68*** | (2006.01) |
| *C07K 14/705* | (2006.01) |

(52) U.S. Cl.
CPC ....... *G01N 33/5011* (2013.01); *C12Q 1/6874* (2013.01); *C12Q 1/6886* (2013.01); *G01N 33/6848* (2013.01); *C12Q 2600/136* (2013.01); *G01N 2333/70539* (2013.01)

(58) Field of Classification Search
None
See application file for complete search history.

(56) References Cited

U.S. PATENT DOCUMENTS 12,152,077 B1 * 11/2024 Amigorena ............ A61K 35/17
12,622,926 B2 * 5/2026 Amigorena ............ A61K 35/17
2016/0047004 A1 2/2016 Bentwich et al.
2016/0153053 A1 6/2016 Skog et al.
2017/0202939 A1 7/2017 Carreno et al.
2019/0256924 A1 8/2019 Vogelstein et al.

FOREIGN PATENT DOCUMENTS

WO 2019075112 A1 4/2019

OTHER PUBLICATIONS

Zhang et al (J. Thoracic Oncol., 2018, 13(125) abstract P079, 2 pages) (Year: 2018).*
Kong et al (Nature Comm., 2019 10:5228, pp. 1-14, https://doi.org/10.1038/s41467-019-13035-2) (Year: 2019).*
Roberts et al (nature Genetics, 2013, 45(9): 970-977) (Year: 2013).*
PCT/US2020/056344, "International Preliminary Report on Patentability", Apr. 28, 2022, 13 pages.
Anwar et al., "Transposable Elements in Human Cancer: Causes and Consequences of Deregulation", International Journal of Molecular Sciences, vol. 18, Issue 5, May 4, 2017, pp. 1-20.
PCT/US2020/056344, "International Search Report and Written Opinion", Mar. 22, 2021, 18 pages.
PCT/US2020/056344, "Invitation to Pay Additional Fees and, Where Applicable, Protest Fee", Jan. 28, 2021, 3 pages.

* cited by examiner

*Primary Examiner* — Misook Yu
*Assistant Examiner* — Marianne Dibrino
(74) *Attorney, Agent, or Firm* — Kilpatrick Townsend & Stockton LLP

(57) ABSTRACT

Candidate cancer antigens are identified using transposable elements. Differential expression levels are determined for proteins using baseline expression levels (using measurements of healthy tissue) and tumor expression levels (using measurements of tumor tissue). Protein(s) having a differential expression level greater than a threshold are selected. Cancer vaccine(s) are generated for the selected cancer antigens (s). Particular cancer vaccine(s) are selected for a patient based on differential expression levels for proteins using baseline expression levels of the patient and tumor expression levels of the patient. A vaccine for protein(s) having a differential expression level greater than a threshold can be selected. A microarray can be used for the measurements of the patient. A first array of probes can hybridize to RNA from transposable elements. A second array of probes can hybridize to RNA of different MHC haplotypes. A third array of probes can hybridize to RNA of different APOBEC genotypes.

19 Claims, 15 Drawing Sheets

Specification includes a Sequence Listing.

SEQUENCE LISTING

<160> NUMBER OF SEQ ID NOS: 304

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tacgttagac ctaaaaccat aaaaacccta g 31

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
aattcaagat ggattaaaga tttatacgtt a 31

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
aaagatttat acgttagacc taaaaccata a 31

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 4
tcaagatgga ttaaagattt atacgttaga c 31

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 5
caagatggat taaagattta tacgttagac c 31

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 6
tcgcctccta aagtgctggg attacaggcg t 31

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 7
gatctcttga cctcgtgatc caccctcctt g 31

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 8
cctctgcctc ctgggtttga gcaattctcc t 31

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 9
aagtgctagg attacaggcg tgagcctctg c 31

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 10
ctaacagtga aaccctgtct ctactaaaaa t 31

<210> SEQ ID NO 11
<211> LENGTH: 8
<212> TYPE: PRT
<213> ORGANISM: Homo sapiens

<400> SEQUENCE: 11

Lys Ile Lys Gly Trp Arg Lys Ile
1 5

<210> SEQ ID NO 12
<211> LENGTH: 8
<212> TYPE: PRT
<213> ORGANISM: Homo sapiens

<400> SEQUENCE: 12

Ile Lys Arg Asn Glu Gln Ser Leu
1 5

<210> SEQ ID NO 13
<211> LENGTH: 9
<212> TYPE: PRT
<213> ORGANISM: Homo sapiens

<400> SEQUENCE: 13

Ser Phe Tyr Glu Ala Ser Ile Ile Leu
1 5

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 14
gatttatacg ttagacctaa aaccataaaa a 31

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 15
aagatttata cgttagacct aaaaccataa a 31

<210> SEQ ID NO 16
<211> LENGTH: 31
<212> TYPE: DNA

<213> ORGANISM: Artificial Sequence
<220> FEATURE:
<223> OTHER INFORMATION: Description of Artificial Sequence: Synthetic probe

<400> SEQUENCE: 16
attcaagatg gattaaagat ttatacgtta g 31

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 17
atcaattcaa gatggattaa agatttatac g 31

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 18
tcaattcaag atggattaaa gatttatacg t 31

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 19
tatacgttag acctaaaacc ataaaaaccc t 31

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 20
tatacaaaaa tcaattcaag atggcttaaa g 31

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 21
taggcgtggg caaggacttc acgtccaaaa c 31

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 22
cttatacaaa aatcaattca agatggctta a 31

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 23
gccctaaaag agctcctgaa ggaagcggta a 31

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 24
agctcctgaa ggaagcggta aacatggaaa g 31

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 25
aagcggtaaa catggaaagg aacaaccggt a 31

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 26
gcggtaaaca tggaaaggaa caaccggtac c 31

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 27
ctaaaagagc tcctgaagga agcggtaaac a 31

<210> SEQ ID NO 28
<211> LENGTH: 31
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 28
gaagcggtaa acatggaaag gaacaaccgg t 31

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
gacaagaatg ccctctctca ccgctcctat t 31

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
agacaagaat gccctctctc accgctccta t 31

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tcaactacat ggaaactgat caacctgctc c 31

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
gctcaactac atggaaactg atcaacctgc t 31

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
aactgatcaa cctgctcctg aatgactact g 31

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 34
tgatcaacct gctcctgaat gactactggg t 31

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 35
aaactgatca acctgctcct gaatgactac t 31

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 36
atgagtgaat tcccattcac aattgtttca a 31

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 37
cacagactgg caagttggat aaagactcaa g 31

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 38
gacacagact ggcaagttgg ataaagactc a 31

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 39
acagactggc aagttggata aagactcaag a 31

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 40
agctcctgaa ggaagcgcta aacatggaaa g 31

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 41
aggaaataaa agaggacaca aacaattgga a 31

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 42
agagaaatgc aaatcaaaac cactatgaga t 31

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 43
tcagagaaat gcaaatcaaa accactatga g 31

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 44
atcagagaaa tgcaaatcaa aaccactatg a 31

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 45
gaaatgcaaa tcaaaaccac tatgagatat c 31

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 46
gagaaatgca aatcaaaacc actatgagat a 31

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 47
ctcacaccag ttagaatggc aatcattaaa a 31

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 48
tcacaccagt tagaatggca atcattaaaa a 31

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 49
acaccagtta gaatggcaat cattaaaaag t 31

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 50
aagcgctaaa catggaaagg aacaaccggt a 31

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 51
gaatcactaa acatggaaag gaacaaccgg t 31

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 52
tccacacgta tgtttattgc agcactattc a 31

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 53
catccacacg tatgtttatt gcagcactat t 31

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 54
gagctgatgg agctgaaaac caagactcga g 31

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 55
agctgatgga gctgaaaacc aagactcgag a 31

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 56
atggagctga aaaccaagac tcgagaacta c 31

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 57
gagctgaaaa ccaagactcg agaactacgt g 31

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 58
tgaaaaccaa gactcgagaa ctacgtgaag a 31

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 59
ctgaaaacca agactcgaga actacgtgaa g 31

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 60
ttccccaatc tagcaaggca gaccaacgtt c 31

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 61
ggcagaccaa cgttcagatt caggaaatac a 31

<210> SEQ ID NO 62
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 62
gcgctaaaca tggaaaggaa caaccggtac c 31

<210> SEQ ID NO 63
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 63
aagatttaaa cgttaaacct aaaaccataa a 31

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 64
ttgtccctgt ttgcagacga catgattgtt t 31

<210> SEQ ID NO 65
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
gtctatgtga aaagaccaaa tctacgtctg a 31

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
caacaagagg agctaactat cctaaatatg t 31

<210> SEQ ID NO 67
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
gaagcgctaa acatggaaag gaacaaccgg t 31

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
ataggcgtgg gcaaggactt cacgtccaaa a 31

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
gtcgggttac cctcaaagga aagcccatca g 31

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
cgggttaccc tcaaaggaaa gcccatcaga c 31

<210> SEQ ID NO 71
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 71
ctcctgaagg aagcgctaaa catggaaagg a 31

<210> SEQ ID NO 72
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 72
aggacatagg cgtgggcaag cacttcatgt c 31

<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 73
attcaggaca taggcgtggg caagcacttc a 31

<210> SEQ ID NO 74
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 74
ataggcgtgg gcaagcactt catgtccaaa a 31

<210> SEQ ID NO 75
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 75
ggcgtgggca agcacttcat gtccaaaaca c 31

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 76
ttcaggacat aggcgtgggc aagcacttca t 31

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 77
gcaagcactt catgtccaaa acaccaaaag c 31

<210> SEQ ID NO 78
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 78
taggcgtggg caagcacttc atgtccaaaa c 31

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 79
ctaaaagagc tcctgaagga agcactaaac a 31

<210> SEQ ID NO 80
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 80
gttaccctca aaggaaagcc catcagacta a 31

<210> SEQ ID NO 81
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 81
aaagagctcc tgaaggaagc actaaacatg g 31

<210> SEQ ID NO 82
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 82
ccagattcat aaagcaagtc ctcagtcacc t 31

<210> SEQ ID NO 83

<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 83
gattcataaa gcaagtcctc agtcacctac a 31

<210> SEQ ID NO 84
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 84
agattcataa agcaagtcct cagtcaccta c 31

<210> SEQ ID NO 85
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 85
taaagcaagt cctcagtcac ctacaaagag a 31

<210> SEQ ID NO 86
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 86
aagtcctcag tcacctacaa agagacttag a 31

<210> SEQ ID NO 87
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 87
agattcataa agcaagtcct caatgaccta c 31

<210> SEQ ID NO 88
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 88
gattcataaa gcaagtcctc aatgacctac a 31

<210> SEQ ID NO 89
<211> LENGTH: 31

<212> TYPE: DNA
<213> ORGANISM: Artificial Sequence
<220> FEATURE:
<223> OTHER INFORMATION: Description of Artificial Sequence: Synthetic
probe

<400> SEQUENCE: 89
atacagagaa gtgcttaaag gagctgatgg a 31

<210> SEQ ID NO 90
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 90
ctcctgaagg aagcggtaaa catggaaagg a 31

<210> SEQ ID NO 91
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 91
aagagctcct gaaggaagcg gtaaacatgg a 31

<210> SEQ ID NO 92
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 92
gatcaagtgg aagaaagggt atcagcaatg g 31

<210> SEQ ID NO 93
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 93
atcaagtgga agaaagggta tcagcaatgg a 31

<210> SEQ ID NO 94
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 94
caagtggaag aaagggtatc agcaatggaa g 31

<210> SEQ ID NO 95
<211> LENGTH: 31
<212> TYPE: DNA

<213> ORGANISM: Artificial Sequence
<220> FEATURE:
<223> OTHER INFORMATION: Description of Artificial Sequence: Synthetic probe

<400> SEQUENCE: 95
aaagagctcc tgaaggaagc agtaaacatg g 31

<210> SEQ ID NO 96
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 96
aatatttatg cacccaatac aggagcactc a 31

<210> SEQ ID NO 97
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 97
cgtctgactg gtgtacctga aagtgatgtg g 31

<210> SEQ ID NO 98
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 98
ttaccctcaa aggaaagccc atcagactaa c 31

<210> SEQ ID NO 99
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 99
ctgccctaaa agagctcctg aaggaagcgc t 31

<210> SEQ ID NO 100
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 100
ccctaaaaga gctcctgaag gaagcgctaa a 31

<210> SEQ ID NO 101
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
agaataacca atacagagaa gtgcttaaag g 31

<210> SEQ ID NO 102
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
gaataaccaa tacagagaag tgcttaaagg a 31

<210> SEQ ID NO 103
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
aatacagaga agtgcttaaa ggagctgatg g 31

<210> SEQ ID NO 104
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
aagtgcttaa aggagctgat ggagctgaaa a 31

<210> SEQ ID NO 105
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
agtgcttaaa ggagctgatg gagctgaaaa c 31

<210> SEQ ID NO 106
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
tacttcatgt ccaaaacacc aaaagcaatg g 31

<210> SEQ ID NO 107
<211> LENGTH: 31
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 107
atatatatgc acccaataca ggagcactca g 31

<210> SEQ ID NO 108
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
gccctaaaag agctcctgaa ggaagcgcta a 31

<210> SEQ ID NO 109
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
tcttttctct ttgatgtaaa agtctttgat c 31

<210> SEQ ID NO 110
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
gcggaaaccc cgactcaaat acaggaaatg t 31

<210> SEQ ID NO 111
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
cataccattt ggtttaagcc ttacattcat g 31

<210> SEQ ID NO 112
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
ttccaaatga atggtctctg gtcaaatgaa t 31

<210> SEQ ID NO 113
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 113
tcttgcccca aatatgcatt tgttctcagt t 31

<210> SEQ ID NO 114
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 114
gaagaccctg aatggagggc cctgcaggag a 31

<210> SEQ ID NO 115
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 115
tggcaggtgc ctgtagtccc agctactcgg c 31

<210> SEQ ID NO 116
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 116
ataccttgta gcctacatag tttgtgattt c 31

<210> SEQ ID NO 117
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 117
aagcagcccc gcacttctcg aaggtctgag t 31

<210> SEQ ID NO 118
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 118
ttcttttgta ttgttattta caatattgtt a 31

<210> SEQ ID NO 119
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 119
tcttccttgc tccatgccca ggggctgact t 31

<210> SEQ ID NO 120
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 120
atggatcaaa tttaatgtgg gcatgaatgg c 31

<210> SEQ ID NO 121
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 121
ttcccctaat aaccatcaca gtgaggggga g 31

<210> SEQ ID NO 122
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 122
tagggaggtg attttttttc tctctctgct t 31

<210> SEQ ID NO 123
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 123
tcgggccgaa gcgccgctca gcgccagcct g 31

<210> SEQ ID NO 124
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 124
ctttctcaac attattgtat tttccactta t 31

<210> SEQ ID NO 125
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 125
ccagagcact gaagcatctc caaaacgtag t 31

<210> SEQ ID NO 126
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 126
gttttggtca cctgaggaac ctatctttgt t 31

<210> SEQ ID NO 127
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 127
ctctgttgct gacttgattc aagttgcagc g 31

<210> SEQ ID NO 128
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 128
tactattgct tgtatattgt ggtatacggt g 31

<210> SEQ ID NO 129
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 129
agtgggcagt ttcttgtgca gatttgcctt t 31

<210> SEQ ID NO 130
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 130
taaaggaaag tatgaatgga gaggggaaag c 31

<210> SEQ ID NO 131
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 131
ctgcagacag ttcagcgcgc ccaccagatc c 31

<210> SEQ ID NO 132
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 132
aaataatgca acagtcaaac ctaattttac a 31

<210> SEQ ID NO 133
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 133
gatgaggaaa ctgaagctca aagaggctca a 31

<210> SEQ ID NO 134
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 134
tgctccagag ttctttttgt tcactcctac c 31

<210> SEQ ID NO 135
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 135
ctttctttca tcctggggct gacttgcagc t 31

<210> SEQ ID NO 136
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 136
agctttgcat aaaactcctc aaaagagttg c 31

<210> SEQ ID NO 137
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 137
taattttaca gagaaactga catgaaatca c 31

<210> SEQ ID NO 138
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 138
tgatgccatc taatggtccc agaagaaact g 31

<210> SEQ ID NO 139
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 139
cccgctacat cgccgtggag tacgtagacg a 31

<210> SEQ ID NO 140
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 140
ataaatttta aaaataaaga ataaaaatat a 31

<210> SEQ ID NO 141
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 141
aaatgggcta tttagagtgt tacctctcac t 31

<210> SEQ ID NO 142
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 142
aggtcctgtt tttgttctac cccaatcact g 31

<210> SEQ ID NO 143
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 143
tcagcggaaa cttgatgata acatggtggt c 31

<210> SEQ ID NO 144
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 144
atgcaagtca cctttctaag tcccagacag c 31

<210> SEQ ID NO 145
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 145
tgactttata gaagccaact tcagtttgaa c 31

<210> SEQ ID NO 146
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 146
aacagataat tatccagccc caataccaag a 31

<210> SEQ ID NO 147
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 147
aaggaggctg atccctgaga ttgttgggat a 31

<210> SEQ ID NO 148
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 148
gcaccatctt atgaaaaggg tccagattaa g 31

<210> SEQ ID NO 149
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 149
tctgcggacg ctgcgcggct actacaatca g 31

<210> SEQ ID NO 150
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 150
caccttccca ggctgatctg aggtaaactt t 31

<210> SEQ ID NO 151
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 151
gtggaaaagg agggagctac tctaaggctg a 31

<210> SEQ ID NO 152
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 152
cacaccctgc agtggatgca tggctgcgag c 31

<210> SEQ ID NO 153
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 153
agagagcctc cactagagtg atgctaagtg g 31

<210> SEQ ID NO 154
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 154
tccgaggatg gtgccgcggg cgccgtggat g 31

<210> SEQ ID NO 155
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 155
cgggtctcac accctgcagt ggatgcatgg c 31

```
<210> SEQ ID NO 156
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156

tcattcccct caccttccca ggctgatctg a                                   31


<210> SEQ ID NO 157
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 157

ggtgacaggg tgaaacgcca tctcaaaaaa t                                   31


<210> SEQ ID NO 158
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 158

gatggaaacg gcctctaccg ggagtagaga g                                   31


<210> SEQ ID NO 159
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159

ctacttcatg atctccagcc ttcctaataa a                                   31


<210> SEQ ID NO 160
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 160

tcgaaactta actctcatgt ccattctcac c                                   31


<210> SEQ ID NO 161
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 161

aaggctgtgg gctcctcaga gaaaatattt g                                   31


<210> SEQ ID NO 162
```

<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 162
tgctggtgcc caccgcgctg ccactgctcc g 31

<210> SEQ ID NO 163
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 163
tgcaggcatg agccactgcg cccgactggt t 31

<210> SEQ ID NO 164
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 164
ccgctacctg cacaggcagg tggctgcagt g 31

<210> SEQ ID NO 165
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 165
gcgtcggctt ctaggctgcc tgggctcgga g 31

<210> SEQ ID NO 166
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 166
agtccctttt tttgtggtct ctttatagat t 31

<210> SEQ ID NO 167
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 167
gaagccaact atggaggaaa tcacagctgc t 31

<210> SEQ ID NO 168
<211> LENGTH: 31

<212> TYPE: DNA
<213> ORGANISM: Artificial Sequence
<220> FEATURE:
<223> OTHER INFORMATION: Description of Artificial Sequence: Synthetic probe

<400> SEQUENCE: 168
tcgggagcct ctgggtgccc ggcggtcagg g 31

<210> SEQ ID NO 169
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 169
gaatggagaa tggcatgagt tttcctgagt t 31

<210> SEQ ID NO 170
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 170
aggagcgagg ggaccgcagg cgggggcgca g 31

<210> SEQ ID NO 171
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 171
attttctgac tcttcccatc agacccccca a 31

<210> SEQ ID NO 172
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 172
cagcgctaga atgtcgccct ccgttgaatg g 31

<210> SEQ ID NO 173
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 173
gtgtaggagg aagagttcag gtggaaaagg a 31

<210> SEQ ID NO 174
<211> LENGTH: 31
<212> TYPE: DNA

<213> ORGANISM: Artificial Sequence
<220> FEATURE:
<223> OTHER INFORMATION: Description of Artificial Sequence: Synthetic
      probe

<400> SEQUENCE: 174
catgggtggt cctagggtgt cccatgaaag a 31

<210> SEQ ID NO 175
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 175
ctcagagact cgaactttcc aatgaatagg a 31

<210> SEQ ID NO 176
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
gcagcgggat ggcgaggacc aaactcagga c 31

<210> SEQ ID NO 177
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
gacgtctctg aggaaatgga ggggaagaca g 31

<210> SEQ ID NO 178
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
gccctcacag gacattttct tcccacaggt g 31

<210> SEQ ID NO 179
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 179
ctgaggacta tttatagaca gctctaacat g 31

<210> SEQ ID NO 180
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 180
cagagtaaca ttttagcagg gaaagaagaa t 31

<210> SEQ ID NO 181
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 181
gaccaaaaca tcatatcagc attttttctt c 31

<210> SEQ ID NO 182
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 182
agctctgcag acatcccatt cctgtatggg g 31

<210> SEQ ID NO 183
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 183
tggtattgca ggataaaggc aggtggttac c 31

<210> SEQ ID NO 184
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 184
ctccagagaa aggctcttaa aaatgcagcg c 31

<210> SEQ ID NO 185
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 185
agccgacatt gaagttgact tactgaagaa t 31

<210> SEQ ID NO 186
<211> LENGTH: 31
<212> TYPE: DNA
<213> ORGANISM: Artificial Sequence
<220> FEATURE:

<223> OTHER INFORMATION: Description of Artificial Sequence: Synthetic probe

<400> SEQUENCE: 186
gggtgtttct agagagatat atctggtcaa g 31

<210> SEQ ID NO 187
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 187
aggaatctga tgctcaaaga agttaaatgg c 31

<210> SEQ ID NO 188
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 188
ttaagatagt taagcgtgca taagttaact t 31

<210> SEQ ID NO 189
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 189
tagaagtgtg ccccgccttg ttactggaag c 31

<210> SEQ ID NO 190
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 190
gcggagcagc tgagagccta cctggagggc a 31

<210> SEQ ID NO 191
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 191
gggaagcggc ctctgcggag aggagcgagg g 31

<210> SEQ ID NO 192
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 192
cccggcccgg ccgcggagta ttgggaccgg g 31

<210> SEQ ID NO 193
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 193
ttcttgtccc actgggagtt tcaagcccca g 31

<210> SEQ ID NO 194
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 194
gaccgcgggg gcggggccag ggtctcacac c 31

<210> SEQ ID NO 195
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 195
ccctgagctg ggagccatct tcccagccca c 31

<210> SEQ ID NO 196
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 196
cgcccagagt ctccccgtct gagatccacc c 31

<210> SEQ ID NO 197
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 197
aggaagagct caggtggaaa aggagggagc t 31

<210> SEQ ID NO 198
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 198
gcaaaggcac ctgaatgtgt ctgcgttcct g 31

<210> SEQ ID NO 199
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 199
actgagaggc aagagttgtt cctgcccttc c 31

<210> SEQ ID NO 200
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 200
agtttctttt ctccctctcc caacctacgt a 31

<210> SEQ ID NO 201
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 201
actctcgggg gccctggccc tgacccagac c 31

<210> SEQ ID NO 202
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 202
gggccaggtt ctcacaccat ccagataatg t 31

<210> SEQ ID NO 203
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 203
cgtccacaat catgggccta cccagtctgg g 31

<210> SEQ ID NO 204
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 204
cgctgttcta aagcccgcac gcacccaccg g 31

<210> SEQ ID NO 205
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 205
gaaggcccag tcacagactg accgagtgga c 31

<210> SEQ ID NO 206
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 206
tccaggaccc acacctgctt tcttcatgtt t 31

<210> SEQ ID NO 207
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 207
ggaagagctc agatagaaaa ggagggagtt a 31

<210> SEQ ID NO 208
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 208
atgagaagga tggagggaag ggctggagaa g 31

<210> SEQ ID NO 209
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 209
gtattttgag tagagatggg gtttcactgt g 31

<210> SEQ ID NO 210
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 210
tgtattttga gtagagatgg ggtttcactg t 31

<210> SEQ ID NO 211
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 211
ttgtattttg agtagagatg gggtttcact g 31

<210> SEQ ID NO 212
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 212
tcctgggccc aagcgatcct cctacctcag c 31

<210> SEQ ID NO 213
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 213
gcctcctaag tagctgggat tacagacgtg t 31

<210> SEQ ID NO 214
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 214
actcctgggc tcaagtgatc ctcttacctt g 31

<210> SEQ ID NO 215
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 215
cctgggccca agcgatcctc ctacctcagc c 31

<210> SEQ ID NO 216
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 216
ccgccattgc cgcagatcca gcgcccagag a 31

<210> SEQ ID NO 217
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 217
aacctctgcc tcctgggttt gagcaattct c 31

<210> SEQ ID NO 218
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 218
ctttctctaa aaggtatttg aaatatctca c 31

<210> SEQ ID NO 219
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 219
ctcctgggcc caagcgatcc tcctacctca g 31

<210> SEQ ID NO 220
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 220
gggattacag gcatgcacca ctacgcctgg c 31

<210> SEQ ID NO 221
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 221
gagtctcact ctgtcactag gctggagtgc a 31

<210> SEQ ID NO 222
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 222
cgccattgcc gcagatccag cgcccagaga g 31

<210> SEQ ID NO 223
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 223
gccgcttcta gaccatggag gagaagaaag c 31

<210> SEQ ID NO 224
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 224
caaaagggtc attatctctg ccccctctgc t 31

<210> SEQ ID NO 225
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 225
cctcagcctc ctaagtaact gggactacag g 31

<210> SEQ ID NO 226
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 226
cagcctccct agtagctggg actacaggcg t 31

<210> SEQ ID NO 227
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 227
ccacgccatt ctcctgcctc agcctcccta g 31

<210> SEQ ID NO 228
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 228
ggccatggcc gcttctagac catggaggag a 31

<210> SEQ ID NO 229
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 229
gccatggccg cttctagacc atggaggaga a 31

<210> SEQ ID NO 230
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 230
tgtgcggggc gccctctgcc acgcagccgg c 31

<210> SEQ ID NO 231
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 231
cgacctcagg tgatcctcct gcctcggcct c 31

<210> SEQ ID NO 232
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 232
ccatggccgc ttctagacca tggaggagaa g 31

<210> SEQ ID NO 233
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 233
aggagaagat gtggagactt ctaagaaatg g 31

<210> SEQ ID NO 234
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 234
cctcctgagt agctgggatt acaggcgcct a 31

<210> SEQ ID NO 235
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 235
tgcctcagcc tcctaagtaa ctgggactac a 31

<210> SEQ ID NO 236
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 236
cgtgcaggta ccattaggaa gcagcgggat a 31

<210> SEQ ID NO 237
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 237
gtgcaggtac cattaggaag cagcgggata a 31

<210> SEQ ID NO 238
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 238
tgcaggtacc attaggaagc agcgggataa g 31

<210> SEQ ID NO 239
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 239
ttcaagtgat tctcctgcct cagtctcctg a 31

<210> SEQ ID NO 240
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 240
gggaagctga aagtccctga atgggtggat a 31

<210> SEQ ID NO 241

<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 241
tccgcctcct ggttcaagca attctcctgc c 31

<210> SEQ ID NO 242
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 242
cgcccgccac tacgcccggc taattttttt t 31

<210> SEQ ID NO 243
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 243
caagtgattc tcctgcctca gtctcctgag t 31

<210> SEQ ID NO 244
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 244
tgctgggatt gcaggcatga gccactgcgc c 31

<210> SEQ ID NO 245
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 245
aaagggtcat tatctctgcc ccctctgctg a 31

<210> SEQ ID NO 246
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 246
ccattgccgc agatccagcg cccagagaga c 31

<210> SEQ ID NO 247
<211> LENGTH: 31

<212> TYPE: DNA
<213> ORGANISM: Artificial Sequence
<220> FEATURE:
<223> OTHER INFORMATION: Description of Artificial Sequence: Synthetic probe

<400> SEQUENCE: 247
aaaagggtca ttatctctgc cccctctgct g 31

<210> SEQ ID NO 248
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 248
cgggaagctg aaagtccctg aatgggtgga t 31

<210> SEQ ID NO 249
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 249
ggattggtta ttactcttct gtgatgcctg c 31

<210> SEQ ID NO 250
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 250
attggttatt actcttctgt gatgcctgct t 31

<210> SEQ ID NO 251
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 251
gattggttat tactcttctg tgatgcctgc t 31

<210> SEQ ID NO 252
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 252
tcaagtgatt ctcctgcctc agtctcctga g 31

<210> SEQ ID NO 253
<211> LENGTH: 31
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 253

cgtttctaga tgagaattca caagcgactc a                                    31


<210> SEQ ID NO 254
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 254

ttggccatgg ccgcttctag accatggagg a                                    31


<210> SEQ ID NO 255
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 255

tggccatggc cgcttctaga ccatggagga g                                    31


<210> SEQ ID NO 256
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 256

cctcctgggc ccaagcgatc ctcctacctc a                                    31


<210> SEQ ID NO 257
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 257

attaactcga gcctttagtt tttatccatg t                                    31


<210> SEQ ID NO 258
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 258

cagcctcctg agcagctggg actacaggcg c                                    31


<210> SEQ ID NO 259
<211> LENGTH: 31
<212> TYPE: DNA
<213> ORGANISM: Artificial Sequence
```

<220> FEATURE:
<223> OTHER INFORMATION: Description of Artificial Sequence: Synthetic
probe

<400> SEQUENCE: 259
gccattgccg cagatccagc gcccagagag a 31

<210> SEQ ID NO 260
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 260
tttggccatg gccgcttcta gaccatggag g 31

<210> SEQ ID NO 261
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 261
aagtgattct cctgcctcag tctcctgagt a 31

<210> SEQ ID NO 262
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 262
ctgccgccat tgccgcagat ccagcgccca g 31

<210> SEQ ID NO 263
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 263
ccattaagcc agatgtcaga agctacacca t 31

<210> SEQ ID NO 264
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 264
tgccgccatt gccgcagatc cagcgcccag a 31

<210> SEQ ID NO 265
<211> LENGTH: 31
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 265
atgtgcgggg cgccctctgc cacgcagccg g                                    31

<210> SEQ ID NO 266
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 266
gaggagaaga tgtggagact tctaagaaat g                                    31

<210> SEQ ID NO 267
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 267
cggcctccta gagtgctggg attacaggcc t                                    31

<210> SEQ ID NO 268
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 268
ctccgcctcc tggttcaagc aattctcctg c                                    31

<210> SEQ ID NO 269
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 269
tttgttcaag tctctctgtg tccggggtga g                                    31

<210> SEQ ID NO 270
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 270
ttgttcaagt ctctctgtgt ccggggtgag c                                    31

<210> SEQ ID NO 271
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 271
gtttgttcaa gtctctctgt gtccggggtg a 31

<210> SEQ ID NO 272
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 272
ttttagtaga gacagggctt cactatgttg g 31

<210> SEQ ID NO 273
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 273
agagaaaggg tttcactatg ttggccaggc t 31

<210> SEQ ID NO 274
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 274
agccttctga gtagctggga ttacaggcac c 31

<210> SEQ ID NO 275
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 275
acgtgcaggt accattagga agcagcggga t 31

<210> SEQ ID NO 276
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 276
gacgtgcagg taccattagg aagcagcggg a 31

<210> SEQ ID NO 277
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 277
ccgggaagct gaaagtccct gaatgggtgg a 31

<210> SEQ ID NO 278
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 278
tttagtagag acagggcttc actatgttgg c 31

<210> SEQ ID NO 279
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 279
tgcctcagcc tccttagtag ctgagattac a 31

<210> SEQ ID NO 280
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 280
atgatgtgcg gggcgccctc tgccacgcag c 31

<210> SEQ ID NO 281
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 281
gcttcagtca acttcttaga gttttctaag a 31

<210> SEQ ID NO 282
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 282
gtgtttgttc aagtctctct gtgtccgggg t 31

<210> SEQ ID NO 283
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 283
agtgtttgtt caagtctctc tgtgtccggg g 31

<210> SEQ ID NO 284
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 284
tgtttgttca agtctctctg tgtccggggt g 31

<210> SEQ ID NO 285
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 285
tagtgtttgt tcaagtctct ctgtgtccgg g 31

<210> SEQ ID NO 286
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 286
ctagtgtttg ttcaagtctc tctgtgtccg g 31

<210> SEQ ID NO 287
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 287
ctgcctcagc ctcctgagca gctgggacta c 31

<210> SEQ ID NO 288
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 288
gctagtgttt gttcaagtct ctctgtgtcc g 31

<210> SEQ ID NO 289
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 289
cgaggtgcct ttctctaaaa ggtatttgaa a 31

<210> SEQ ID NO 290
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 290
gaggtggggt ttcactatgt tggccaggct g 31

<210> SEQ ID NO 291
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 291
gcctcctaga gtgctgggat tacaggcctg a 31

<210> SEQ ID NO 292
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 292
tatgctagtg tttgttcaag tctctctgtg t 31

<210> SEQ ID NO 293
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 293
tgctagtgtt tgttcaagtc tctctgtgtc c 31

<210> SEQ ID NO 294
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 294
atgctagtgt ttgttcaagt ctctctgtgt c 31

<210> SEQ ID NO 295
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 295

```
ttagtagaga cggagtttca ctgtgttagc c                                  31


<210> SEQ ID NO 296
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 296

ccaaaagggt cattatctct gccccctctg c                                  31


<210> SEQ ID NO 297
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 297

ctgggcccaa gcgatcctcc tacctcagcc t                                  31


<210> SEQ ID NO 298
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 298

ttacaggcgt gagccactgt gcccagccat a                                  31


<210> SEQ ID NO 299
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 299

aaactttcct taaagttctt attgcctttg c                                  31


<210> SEQ ID NO 300
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 300

aactttcctt aaagttctta ttgcctttgc a                                  31


<210> SEQ ID NO 301
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 301

actttcctta aagttcttat tgcctttgca c                                  31
```

-continued

```
<210> SEQ ID NO 302
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 302

gccaaaaggg tcattatctc tgccccctct g                                31


<210> SEQ ID NO 303
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 303

ctttccttaa agttcttatt gcctttgcac t                                31


<210> SEQ ID NO 304
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304

acgugccacg auucaacgug gcacag                                      26
```

SYSTEM AND METHOD FOR DISCOVERING VALIDATING AND PERSONALIZING TRANSPOSABLE ELEMENT CANCER VACCINES

CROSS-REFERENCES TO RELATED APPLICATIONS

The present application is the National Stage of International Application No. PCT/US2020/056344, filed Oct. 19, 2020, claims priority from and is a nonprovisional application of U.S. Provisional Application No. 62/916,816, entitled "System And Method For Discovering, Validating, And Personalizing Transposable Element Cancer Vaccines," filed Oct. 18, 2019, the entire contents of which are herein incorporated by reference for all purposes.

SEQUENCE LISTING

The instant application contains a Sequence Listing which has been submitted electronically in ASCII format and is hereby incorporated by reference in its entirety. Said ASCII copy, created on Nov. 25, 2020, is named 102913-002210WO1-1192415_SL.txt and is 68,922 bytes in size.

STATEMENT AS TO RIGHTS TO INVENTIONS MADE UNDER FEDERALLY SPONSORED RESEARCH AND DEVELOPMENT

This invention was made with government support under grant no. U54HG007990 awarded by the National Human Genome Research Institute of the National Institutes of Health. The government has certain rights in the invention.

BACKGROUND

Cancer immunotherapy heightens the immune system's ability to recognize a cancer and destroy the cancer cells, as opposed to more traditional compounds that directly inhibit the cancer's ability to proliferate. Cancer immunotherapy can provide good responses, even in advanced stages of cancer. Some current immunotherapies include cancer vaccines, antibodies, T cell infusions, and checkpoint blockade therapy. Malignant tumors often co-opt immune suppressive and tolerance mechanisms to avoid immune destruction. Immune checkpoint blockade removes inhibitory signals of T-cell activation, which enables tumor-reactive T cells to overcome regulatory mechanisms and mount an effective antitumor response. Accordingly, immune checkpoint blockade inhibits T cell-negative costimulation in order to unleash antitumor T-cell responses that recognize tumor antigens.

However, only a subset of patients respond to current cancer immunotherapies, and it is difficult to predict which patients will respond. To increase the number of patients who benefit, combination therapies are being used. Cancer vaccine in combination with checkpoint blockade therapy is a promising approach to increasing the antitumor immune response. But, cancers typically have specific mutations (private mutations) in a person; cancer vaccines based on private mutations may be prohibitively expensive and inhibit widespread adoption of this approach.

BRIEF SUMMARY

Embodiments of the present disclosure provide a strategy for personalized cancer vaccines that use public antigens that are shared across individuals. Genomewide dysregulation of transcription and translation leads to overexpression of non-canonical protein coding genes, including transposable elements (TEs). TEs are strongly repressed in healthy cells to prevent genomic instability but can become dysregulated in cancer. Disclosed herein is a computational framework for identifying potential cancer antigens within transposable elements, e.g., using RNA-seq or mass spectrometry data. Some embodiments use autonomous transposable elements in the human genome, e.g., L1HS.

Embodiments of the present disclosure may include a method for identifying cancer antigens that may be used as cancer vaccines. The method may include identifying a group of candidate cancer antigens that are generated from transposable elements. Embodiments may also include determining a baseline expression level for each of the candidate cancer antigens using measurements of healthy tissue from a first cohort of healthy subjects. Embodiments may also include determining a tumor expression level for each of the candidate cancer antigens using measurements of tumor tissue from a second cohort of cancer subjects. Embodiments may also include determining a differential expression level for each of the candidate cancer antigens using the baseline expression levels and the tumor expression levels. Embodiments may also include selecting one or more of the candidate cancer antigens having a differential expression level greater than a threshold.

Embodiments of the present disclosure may include a method of identifying a cancer vaccine for a patient, the method may include identifying a group of candidate cancer antigens that are generated from transposable elements. Embodiments may also include determining a baseline expression level for each of the candidate cancer antigens, where the baseline expression levels are determined using measurements of healthy tissue from healthy subjects. Embodiments may also include determining a tumor expression level for each of the candidate cancer antigens using measurements of tumor tissue from the patient. Embodiments may also include determining a differential expression level for each of the candidate cancer antigens using the baseline expression levels and the tumor expression levels. Embodiments may also include selecting one or more of the candidate cancer antigens having a differential expression level greater than a threshold. Embodiments may also include selecting a cancer vaccine corresponding to the one or more of the candidate cancer antigens.

Embodiments of the present disclosure may include a microarray including a first array of nucleic acid probes that hybridize to expressed transposable element mRNA from tumor samples or to cDNA derived from such mRNA. Embodiments may also include a second array of nucleic acid probes that hybridize to mRNA or cDNA corresponding to different MHC haplotypes. Embodiments may also include a third array of nucleic acid probes that hybridize to mRNA or cDNA corresponding to mutated different genotypes of APOBEC These and other embodiments of the disclosure are described in detail below. For example, other embodiments are directed to systems, devices, and computer readable media associated with methods described herein.

A better understanding of the nature and advantages of embodiments of the present disclosure may be gained with reference to the following detailed description and the accompanying drawings.

BRIEF DESCRIPTION OF THE DRAWINGS

FIG. 1 provides a high-level overview of an approach for developing probes for TE vaccine development according to embodiments of the present disclosure.

FIG. 2 provides an outline of computational tools available for developing a TE vaccine database according to embodiments of the present disclosure. FIG. 2 discloses SEQ ID NO: 304.

Figure 1:
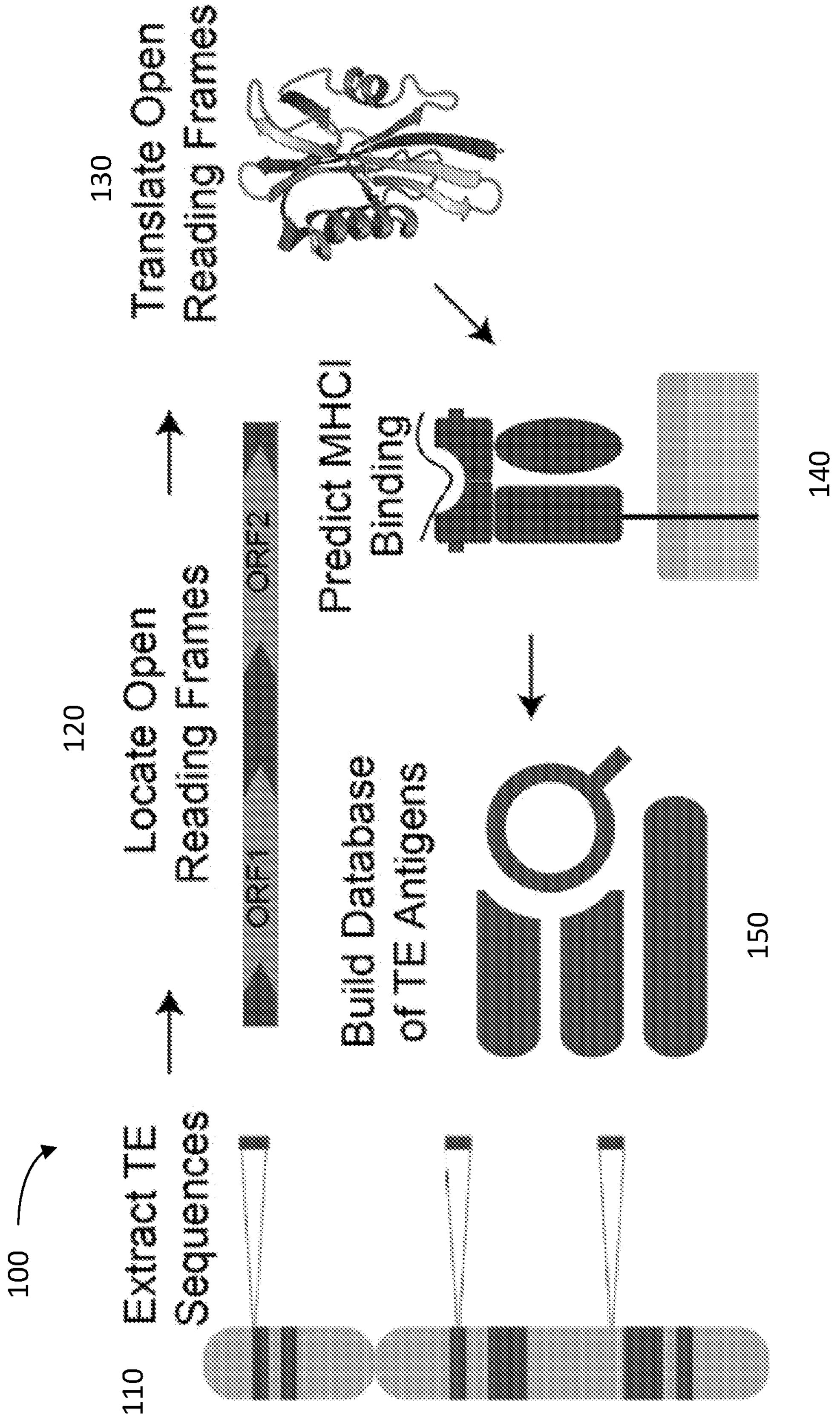
FIGS. 1-2 provide an overview of tools for quantifying transposable element (TE) epitope kmers and APOBEC mutated kmers according to embodiments of the present disclosure.

An Appendix includes: table 2 showing example nucleic acid probes that hybridize to cDNA from transposable elements in a human genome, table 3 showing example nucleic acid probes that hybridize to cDNA corresponding to different antigen presentation pathway genes, and table 4 showing nucleic acid probes that hybridize to cDNA corresponding to APOBEC mutated RNA transcripts.

Terms

The term "transposable element" may refer to a DNA sequence that can change its position within a genome, sometimes creating or reversing mutations and altering the cell's genetic identity and genome size. Transposable elements are shared across individuals and related species.

DETAILED DESCRIPTION

This disclosure provides novel strategies for personalized cancer vaccines by identifying antigens in cancer cells that are shared across at least some individuals. Mutations are typically not shared among a large segment of cancer patients. Thus, proteins associated with such private mutations are not good antigens for a widespread approach. Instead, embodiments recognize that certain proteins (corresponding to transposable elements) are commonly expressed in tumors as a result of dysregulation (e.g., epigenetic dysregulation, as may occur from widespread DNA hypomethylation), where such dysregulation is not caused by sequence variations in the corresponding coding regions. Thus, these antigens will be common among a cohort of the population that share relevant parts of the genetic code, e.g., a same major histocompatibility complex (WIC) and APOBEC ("apolipoprotein B mRNA editing enzyme haplotype") mutational signature. Different tissues may have different regulation of such antigen proteins, but tumors in a same tissue type tend to have dysregulation of similar antigens, thereby enabling a given vaccine to have relatively widespread applicability.

Genomewide dysregulation of transcription and translation leads to overexpression of non-canonical protein coding genes, including transposable elements (TEs). TEs are strongly repressed in healthy cells to prevent genomic instability but can become dysregulated in cancer. Disclosed herein is a computational framework for identifying potential cancer vaccine antigens within transposable elements. Such antigens can be used to stimulate a subpopulation of the patient's T-cells that are capable of identifying cancer cells. By immunizing a patient with the vaccine or by using the peptide to stimulate and expand T cells ex vivo, embodiments can expand and activate the T-cells that are in lymph nodes and circulating throughout the body to attack cancer cells that present TE peptides in the context of a major histocompatibility (MHC) protein.

Since the TEs are highly conserved across a population, cancer vaccines derived from TE's can have wide applicability. Further, since TE antigens are not normally expressed in healthy cells, there is potentially limited toxicity in such a vaccine. TE antigens can be selected using further criteria, e.g., solubility of the peptide or ability to be presented by the HLA molecules of an individual patient.

To identify TE proteins that are overexpressed in tumors, various embodiments can be used to analyze RNA sequencing data (from which protein expression can be inferred) or direct protein measurements, such as mass spectrometry. From this, a set of candidate TE proteins (candidate cancer antigens) can be identified. Such TE proteins can be defined/identified by kmers in TE loci in the genome or directly as described above. In particular, a TE type of long interspersed nuclear elements (LINEs) may be used, more specifically L1HS may be used. The L1HS subclass of LINEs is human-specific and its protein coding sequences are strongly conserved. As described herein, a kmer is a subsequence of a biological sequence (such as a polynucleotide or polypeptide) of a length k. The term kmer can also refer to all of a biological sequences subsequences of length k.

To detect overexpression of a TE protein, a baseline expression can be established in the candidate set of kmers/proteins. The baseline expression may be specific to a particular demographic, e.g., age, tissue type of the tumor, etc. The kmers/proteins can be ranked by levels of overexpression, with the ones being most highly overexpressed identified as candidate cancer antigens and peptides corresponding to those candidate cancer antigens can be synthesized. For example, clinical grade peptides corresponding to all or a portion of a particular kmer/protein in a ranked set of kmers/proteins can be synthesized using a solid-phase peptide synthesizer according to the 9-fluorenylmethoxycarbonyl group (Fmoc) protocol and validated using reverse-phase high-performance liquid chromatography followed by mass-spectrometry, or by other methods known to those of ordinary skill in the art.

When measuring expression levels and/or identifying genomic locations corresponding to directly measured proteins, the occurrence of RNA having a particular kmer (e.g., 24 mer) sequence can be identified. A particular kmer can correspond to multiple loci, and more than one kmer can correspond to a particular locus. Such knowledge of kmers and loci in the transposable elements (e.g., L1HS) can be used to create a mapping between certain proteins and certain kmers, potentially with different weights of a mapping between a kmer and a protein. The weights can be used to estimate a total expression of a particular protein by determining a weighted sum of the expression levels for each of the kmers mapped to the particular protein. The frame of each locus and the MHC haplotype of the patient can be used, along with the corresponding kmers, to determine the resulting proteins that are highly overexpressed.

Thus, a set of peptides can be generated for a set of protein antigens that are likely to be generally applicable for use as vaccines for administration to cancer patients. Then, for a second patient, RNA or protein measurements can be used to determine TE proteins that are overexpressed in the second patient. Peptides corresponding to the TE proteins from the second patient can be synthesized, or if a peptide is common to the first patient and the second patient, the common peptide can be selected for use as a vaccine. In this manner, a vaccine can be personalized to a patient (e.g., a particular vaccine can be newly synthesized or selected from a library).

Further, an APOBEC mutation signature can be used to determine whether the patient is likely to respond to a TE cancer vaccine. The APOBEC mutation signature can be inferred from RNA sequencing data.

The disclosed methods were applied to triple negative breast cancer (TNBC) and melanoma and it was determined that L1HS epitope kmers correlate with better survival in TNBC and complete response to checkpoint blockade therapy in melanoma. This illustrates that these elements correlate with better survival, presumably through activation of the host immune system. Further activation through vaccination can lead to even stronger antitumor immune responses, which can work synergistically with checkpoint blockade therapy.

I. INTRODUCTION

Cancer is the second leading cause of death in the United States [1], and while there have been significant medical advances in treating this disease, the standard of care has not changed significantly over the past few decades. Chemotherapy, radiation, and surgery have been the frontline defense against cancer progression, but new therapeutic strategies are being developed that personalize the therapy to individuals. For example, targeted therapies are small-molecule drugs designed to inhibit specific molecular alterations, such as an activating kinase mutation. These therapies have generated complete responses in late-stage disease, but resistance often emerges and the cancer relapses. Targeted therapies are routinely used against recurrent activating mutations, including BRAF V600E in melanoma, but most patients do not have an actionable variant and do not benefit from these approaches. Furthermore, targeted therapies do not yield durable responses, since the cancer eventually relapses, and incur significant cost to the healthcare system [2].

Another approach for treating cancer is to amplify the antitumor immune response. This approach has achieved remarkable responses while inducing minimal toxic side-effects. The discovery that the immune system can recognize and destroy cancer cells has opened the door to an entirely new therapeutic approach. Genome-wide dysregulation of transcription and translation leads to the presentation of tumor-specific antigens by major histocompatibility complex molecules on the cell surface. Cytotoxic T cells recognize tumor-specific antigens and induce immune-mediated cell death of those tumors.

Unfortunately, this process can select for cancer cells that evade immune recognition, which leads to an immunosuppressive tumor microenvironment that is able to coexist with the host's immune system [3]. Cancer cells can evade immune recognition via inhibitory signals. Inhibitory signals can be created by (1) a reduction in the expression of proteins that would otherwise be detected by the immune system, or by (2) an increase in the expression of proteins that stop the immune system from attacking cancer cells or drowning out other antigenic proteins that the immune system could otherwise identify and attack. As an example, some cancer cells adopt immunosuppressive cell-surface markers to curb the antitumor immune response. These include the immune checkpoint molecules CTLA4 and PDL1. Identification of immune checkpoint expression in cancer has led to the development of antibody therapies that block the immunosuppressive signal allowing cytotoxic T-cells to continue the antitumor attack. Checkpoint blockade therapy can reduce the effect of immune checkpoint proteins, resulting in. durable responses with relatively minor toxic side-effects [4-7].

The anti-CTLA4 antibody, ipilimumab, was the first checkpoint blockade therapy to achieve FDA approval [6,8]. CTLA4 has a stronger binding affinity to CD80 and CD86 than the costimulatory CD28 molecules, leading to inhibition of T-cell activation [3]. CTLA4 normally becomes expressed after T-cell activation in order to prevent off-target autoimmunity; cancer cells may express CTLA4 to prevent cytotoxic T-cell activation [4-6]. The anti-PD1 antibody pembrolizumab came later and was found to be more efficacious and have fewer side-effects [9]. PD1 is a cell-surface receptor expressed after T-cell activation. Activation of the PD1 receptor by its ligand PDL1 leads to interference of downstream signaling from the T-cell receptor which suppresses the T-cell response [7,8].

The extraordinary responses to checkpoint blockade therapy has led to this therapy becoming widely used and at increasingly earlier stages in cancer treatment [7]. Using checkpoint blockade as a monotherapy achieves a response rate between 20 and 40% for melanoma [4,9]. Current biomarkers for response include PDL1 expression, T-cell infiltration, tumor bulk, mutation burden, crippled DNA repair machinery, and microsatellite instability. One of the markers for checkpoint blockade therapy is a high mutation burden. That is a problem for many patients who do not have a high mutation burden. In pediatric cancers, the mutation burden is extremely low and in some cases patients do not have a single mutation. And, even if there are mutations, these coding mutations only represent a small fraction (e.g., 5%) of the genome. Thus, there is a desperate need for therapeutic strategies that can induce responses similar to checkpoint blockade therapy, but in tumors that do not have the traditional biomarkers for response to check the blockade therapy.

In addition to identifying predictive biomarkers of response, combination immune checkpoint therapies are being investigated. Administering anti-CTLA4 and anti-PD1 therapies increases the response rate (>40%), but at the cost of increasing the number of adverse events, including fatal pulmonary toxicity [9]. The increased response rate with combination immunotherapy shows that further activation of the immune system correlates with increased antitumor effects. The additional toxic side-effects limit this approach's utility, so new approaches are needed to similarly activate the antitumor immune response while avoiding toxic side-effects. Checkpoint blockade therapy allows infiltrating T-cells to continue their cytotoxic functions, but does not influence the T-cell clones that travel to the tumor. Therapies that expand T-cell clones that are able to recognize cancer cells may work synergistically with checkpoint blockade therapy to tip the balance in favor of immune-mediated destruction of tumors [10].

During a normal infection, antigen-presenting cells enter peripheral lymph nodes to excite T-cells that recognize the antigen into rapidly expanding and circulating throughout the body in search of the antigen. Another strategy for improving response to checkpoint blockade therapy may be to increase the number of circulating T-cells able to recognize cancer cells using a cancer vaccine approach. Cancer vaccines expand the T-cells able to recognize cancer cells and increase the number of T-cells infiltrating the tumor [11].

Despite extensive research into cancer vaccines, the clinical response to cancer vaccine monotherapy has been modest [12,13]. Sipuleucel-T is the only FDA-approved cancer vaccine that stimulates the immune response against a tumor-specific antigen [14]. This suggests that expanding the number of antitumor T-cells is not sufficient, so checkpoint blockade therapy may be required to overcome the inhibitory mechanisms within the tumor microenvironment. Recent studies have shown that vaccines work synergistically with checkpoint blockade therapy to increase response rates [10,11].

Sipuleucel-T does not target a mutated protein, but instead targets a shared antigen that is overexpressed in prostate cancer cells but not in healthy somatic cells. Being shared across patients has facilitated the development of Sipuleucel-T. The alternative cancer strategy being investigated is to identify private mutations within each tumor and synthesize a unique set of peptide vaccines based on that individuals cancer mutations. The private mutation approach does not scale well since it requires DNA sequencing, alignment, variant calling, MHC binding prediction, peptide synthesis, quality control, and safety validation for each individual patient. It would be ideal to identify a set of protein-coding genes within the genome that are uniquely expressed in cancer cells but are also shared across individuals. However, this approach may also need to be personalized to the individual since the immunopeptidome reflects that patient's particular HLA genotype.

Accordingly, embodiments of the present disclosure can identify neoantigens that are uniquely (or at least predominantly) expressed in cancer cells, where new vaccines can be engineered to train the immune system to recognize and react to these neoantigens. Such vaccines can be used in combination with (e.g., before) checkpoint blockade therapy, e.g., to boost the number of T cells that can recognize these neoantigens (like viral peptides) in the patient's body. In this manner, when checkpoint blockade therapy is administered, the immunosuppression of the cancer cells is removed, and the number of T-cells that are able to recognize the cancer cells has been increased. The checkpoint blockade therapy can unleash the immune system, and the vaccine can help the immune system recognize and react to the cancer cells. The disclosed vaccines can also be used in the absence of checkpoint blockade therapy.

II. TRANSPOSABLE ELEMENTS (TE)

There is one FDA-approved cancer vaccine that helps the immune system recognize and react to a non-mutated gene that is overexpressed in cancer cells and not normal cells. This is an attractive model because cancer cells typically overexpress a large number of genes not usually expressed in healthy cells. Dysregulation of transcription and translation is a hallmark of cancer and causes many non-canonical genes to be expressed in tumor cells.

Epigenetic dysregulation is a hallmark of cancer. Cancer cells take on a stem-cell-like state, with the genome taking on a more euchromatic structure. This, in combination with widespread DNA hypomethylation, allows genes that are normally silenced to become expressed. Notably, 40% of the genome is composed of self-propagating DNA elements known as transposable elements (TEs), which the genome silences early in development via repressive epigenetic marks. TEs encode virus-like genes that facilitate reintegration of their sequences throughout the genome. These elements are normally repressed to prevent genomic instability, but have been identified in specific tissues and developmental stages. For example, transposable elements are under selective pressure to retrotranspose in germline cells in order to propagate across generations. There have also been reports of higher expression in brain tissue and stem cells [16-24]. But, in cancer, these repressive mechanisms get broken, resulting in wonton expression of these TE genes.

Transposable elements can be subdivided into DNA transposons and retrotransposons. DNA transposons replicate with a DNA intermediate, and retrotransposons replicate with an RNA intermediate coupled with a reverse transcription. There are two major classes of retrotransposon: long terminal repeat (LTR) and non-LTR elements [16]. LTR elements are related to retroviruses. The non-LTR elements contain two subclasses, the short interspersed nuclear elements (SINEs) and the long interspersed nuclear elements (LINEs). LINEs are the only class of TE that contain the necessary protein machinery to retrotranspose. Moreover, autonomous LINEs are required for other TEs, including Alu SINEs, to retrotranspose. Rodriguez-Martin, B., Alvarez, E. G., Baez-Ortega, A. et al. Pan-cancer analysis of whole genomes identifies driver rearrangements promoted by LINE-1 retrotransposition. Nat Genet 52, 306-319 (2020); incorporated by reference herein. For this reason, the LINEs are strongly repressed in somatic tissues to prevent genomic instability caused from widespread retrotransposition.

LINE-1 (L1) element L1 *Homo sapiens* (L1HS) is the youngest transposable element in the human genome and is one of the few classes of TEs that is autonomous. It was hypothesized that L1HS would be strongly repressed in somatic tissue, but likely expressed in tumors and thus would be an ideal candidate antigen for developing antitumor vaccine therapies. As the youngest class of TE, L1HS is the most potent at becoming activated in cancer cells since these elements have conserved regulatory sequences and coding regions. Despite the strong conservation, there is sufficient variation for L1HS elements to show differential expression across individuals due to differences in transcriptional regulation at different loci. To account for such differential expression, some embodiments of the disclosed methods can personalize vaccines to each tumor, and allow the re-use of peptides as vaccines for the peptides that are shared across individuals.

Accordingly, some embodiments of the disclosed methods make use of L1HS. L1HS vaccines have been developed to treat HIV patients because, like cancer cells, HIV infected cells also over-express transposable elements. The L1HS HIV vaccines were tested in pre-clinical models, including primates, and found to be immunogenic and safe [25]. However, immunization against these elements did not have an effect in protecting macaques from SIV infection, potentially because these vaccines were based on a consensus sequence of transposable elements and endogenous retro-elements. Therefore they may not have been sufficiently variable to generate a response [26].

Methods for quantifying TE expression are currently being developed, but these methods are not designed for precision immuno-oncology applications. TE expression methods quantify expression at the class level using a consensus sequence or an average across all loci [15,27]. This approach does not capture candidate cancer antigen sequences, particularly those that are present at multiple loci or those that are unique to a specific locus.

Disclosed herein is a novel TE epitope expression quantification method that identifies unique TE sequences for precision cancer vaccine development by DNA and RNA analysis of TE expression. Also disclosed is a mass spectrometry method that identifies MHC bound TE peptides. This approach confirms that TE peptides are presented on MHCs and can be recognized by T cells.

Embodiments include novel approaches based on expression of unique L1HS epitope kmers and peptides in RNA-seq and mass spectrometry data. The disclosed method prioritizes L1HS epitopes that can be identified to facilitate the identification of cancer antigens. Also disclosed herein is a novel process for identifying tumor-specific epitopes that are shared among individuals, allowing for a panel of candidate cancer antigen peptide vaccines to be synthesized, validated, and matched to patient tumors. Normal expression of potential TE epitopes were quantified in several human tissue samples and across developmental stages. L1HS peptides were shown to be processed and presented on triple negative breast cancer (TNBC) tumors but not matched normal tissue. Finally, L1HS epitope expression correlates with better survival in TNBC and with a complete response to checkpoint blockade therapy in melanoma.

III. BUILDING A DATABASE OF TE ANTIGENS

A software toolkit (also referred to as vaccinaTE) was developed to facilitate the identification of candidate cancer antigens. Three functionalities within the toolkit are as follows. A first function generates reference files for building a database of unique transposable element (TE) kmers and peptides. A second function quantifies unique kmers (corresponding to TEs) in RNA-seq data, which can provide RNA kmer frequencies for identifying candidate proteins that are overexpressed in tumor cells.

A third function generates in Silk® mutated kmers to detect APOBEC activity related to activation of an antiviral response within cancer cells. APOBEC randomly mutates mRNA when it senses there is expression of active transposable elements. The third function creates a database of all of the possible mutated mRNA that could result from APOBEC activation, and then quantifies this signal in the patient's RNA-seq data. A high rate of APOBEC-associated mutations correlates with more TE expression and response to vaccine therapy.

The vaccinaTE toolkit facilitates the analysis of transposable elements and their expression for large cancer gene expression datasets. The vaccinaTE toolkit includes routines for identifying open reading frames, predicting WIC binding, ranking peptides by their druggability, quantifying expression of peptides, and assembling full-length transposable elements from RNA-seq data. The vaccinaTE software is written in the C++ programming language to scale to genome-wide analysis of transposable element candidate cancer antigens, but other languages may be used. As further examples, some embodiments also provide several Python routines for preprocessing and analyzing the output of vaccinaTE.

Figure 2:
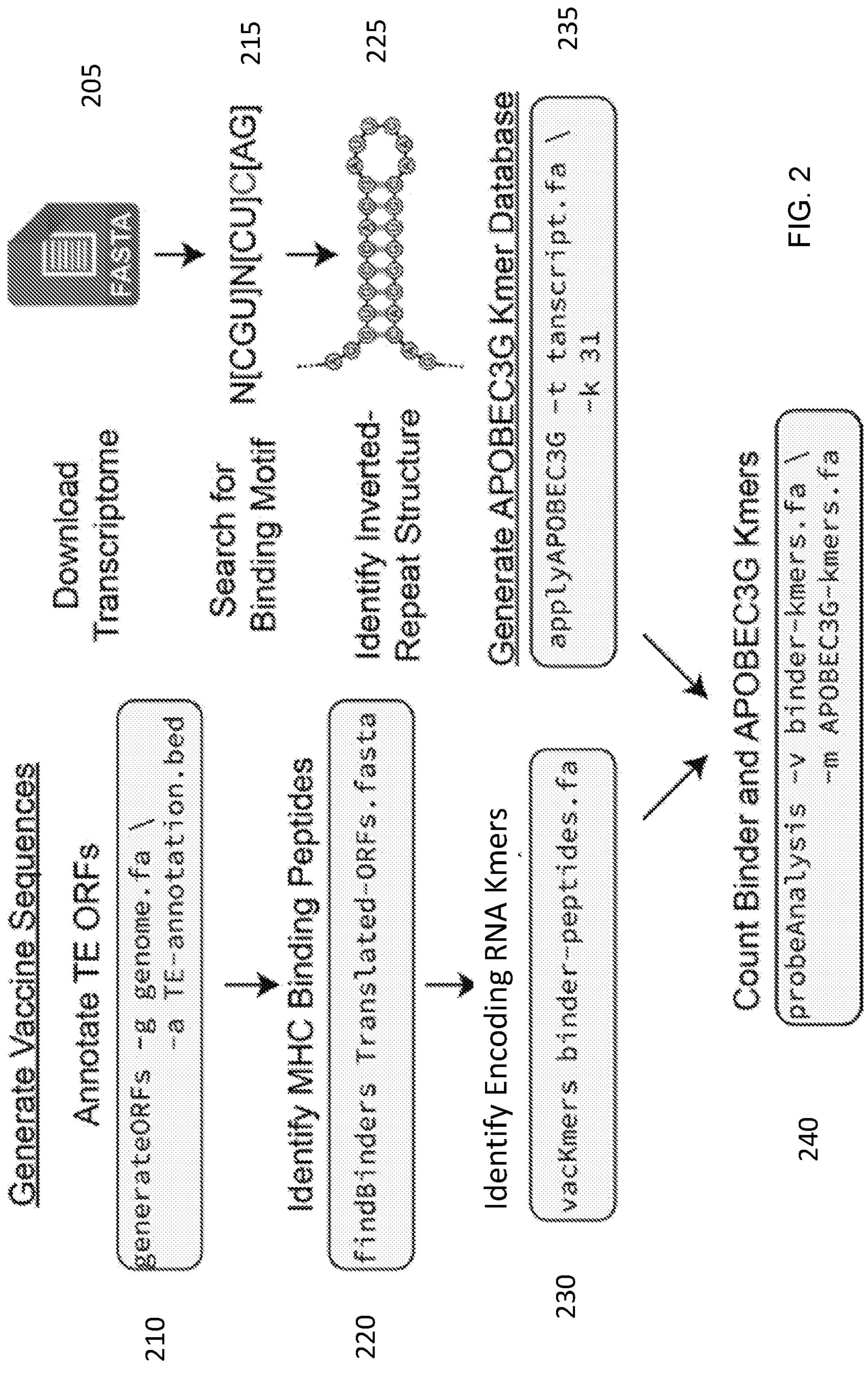

FIGS. 1-2 provide an overview of tools for quantifying transposable element (TE) epitope kmers and APOBEC mutated kmers according to embodiments of the present disclosure.

FIG. 1 provides a high-level overview of an approach 100 for developing probes for TE vaccine development according to embodiments of the present disclosure. Approach 100 can provide a database of proteins to investigate. FIG. 1 provides an explanation for identifying antigens that can be analyzed using experimental data, e.g., whose expression can be analyzed in FIG. 2.

At block 110, transposable element sequences are located and extracted. The TE sequences can be identified using a reference human genome (e.g., hg 38). The transposable sequences can be used to generate kmer sequences (i.e., subsequences of the TE sequence), potentially of various lengths. For example, kmers can be extracted from the transposable sequences. Each instance of a kmer in the TE regions can be identified and used in the approach. The location of each kmer can also be determined. The location can be used to assign a unique identifier to each kmer. A given kmer may appear at multiple locations, potentially with two instances of the kmer overlapping with a same genomic position. In some embodiments, the TE sequences are specific to L1HS.

Of the thousands of L1HS loci, the majority have become degraded and may not generate sufficient protein for vaccine development. The L1base2 database was used to prioritize full-length L1HS elements and L1HS loci with intact ORF2 sequences [37].

At block 120, the open reading frames are located. An open reading frame defines how the protein is encoded. An open reading frame is defined by a start codon (3-base sequence, usually AUG in terms of RNA) and a stop codon (usually UAA, UAG or UGA). The open reading frames can be identified in the transposable elements, for which kmer locations are known. As the open reading frames provides a complete protein sequence, the open reading frames can be used to map a kmer to a protein sequence, which can be needed when measuring expression levels for a particular protein using RNA measurements (e.g., RNA sequencing data).

The hg38 genome annotation was used to generate L1HS ORFS. The generate ORFs tool was used to identify protein-coding regions within L1HS elements. Protein domains within ORFs were investigated using the Pfam tool [38].

At block 130, the open reading frames are translated into a protein sequence. The standard human genetic code can be used to translate each open reading frame into a corresponding protein sequence (Osawa S. et al., Microbiol Rev., 56, 229-264; (1992) incorporated by reference herein). The open reading frames that map to known transposable element domains are used for downstream identification of candidate cancer antigens.

At block 140, it is predicted which of the protein sequences (peptides) from candidate cancer antigens are able to bind to MHC, and thus would present on a surface of the cell. MHC is the complex that holds the epitope on the cell surface. MHC is the general term, and human leukocyte antigen (HLA) is the human specific term for human Class I MHC. Different MHCs can be tested, as different MHC haplotypes exist in the population. Peptides that do not bind to at least one version of MHC can be removed (discarded). In some embodiments, it is determined whether the peptides will bind to the MHC (including HLA) haplotypes present in an individual patient.

In some implementations, the netMHCpan-4.0 software was applied to the translated L1HS ORFs for 2427 HLA genotypes. 8mers, 9mers, 10mers, and 11mers were investigated (although other kmers can be investigated). Certain peptides found in the open reading frames of proteins can be selected, for examples, peptides that were predicted to bind to at least one HLA allele with a minimum percentile rank, e.g., 2%.

At block 150, the peptides meeting specified criteria (e.g., the minimum percentile rank) can be assembled into a database. The peptides from block 140 can be mapped back to the transcript kmers to create a database of corresponding probes, which may be used in downstream analyses. For example, these probes can be used to detect expression levels. Such probes can be certain sequences to be identified in sequencing data or physical probes that can provide a signal when a specific sequence is detected, e.g., via hybridization. The measured levels of such probes can be aggregated (potentially with weights) to determine an expression level of a corresponding protein that may be a candidate cancer antigen. The aggregation can be a weighted sum, where each weight multiples a measurement amount of a particular kmer that contributes to the protein. The aggregated amount can be normalized, e.g., based on a total number of molecules analyzed.

The database can be created in such a way to facilitate going from DNA to protein space and vice versa. A peptide can be stored in connection with one or more kmers, and a peptide entry can have fields for each unique kmer location that contributes to generating that peptide. Alternatively or in addition, a kmer entry can be stored with fields(s) for each peptide that the kmer is included in the open reading frame that codes for the protein.

The database can be used to identify where a TE could have been generated in the human genome as well as identifying what proteins could have been generated by an over-expressed transcript. Without this database, one would need to realign the many kmer and peptide sequences. The database can be queried based on peptide and/or DNA kmer sequences. In some implementations, any sequences that could have been generated by a non-TE region of the genome are removed.

Embodiments can perform the identification of transposable element immunotherapy candidate cancer antigens using the vaccinaTE toolkit.

FIG. 2 provides an outline of computational tools available for developing a TE vaccine database according to embodiments of the present disclosure. Once the initial database of candidate cancer antigens is created, embodiments can determine which of the corresponding kmers are overexpressed in a tumor cohort. A series of software tools can perform this process.

At block 210, annotations of a reference sequence can be used to identify TE regions, and particular types of TE regions, e.g., L1HS. Accordingly, the underlying database of TE candidate cancer antigens can be based on TE annotations from a human reference genome sequence. The open reading frames (ORFs) can be automatically detected and the resulting ORFs can be extracted. Thus, this routine can start in a DNA space of the TE regions and identify ORFs corresponding to an RNA space.

Accordingly, a step of the pipeline can identify unique open reading frames (ORFs) across all TEs. The generate-ORFs command takes a genome sequence file and a transposable element annotation file and generates the transcripts and predicted protein sequences for downstream analysis. There are several TE databases of interest to the cancer research community on the UCSC Xenahub [35].

At block 220, a routine determines whether peptides corresponding to the ORFs bind to MHCs. These ORFs can be defined as kmers of RNA, e.g., by each ORF including a collection of kmers at different locations in the ORF. This routine can translate the ORFs to peptides (e.g., as in block 130), and then determine whether those peptides bind to one or more MHC alleles.

As shown in FIG. 2, the ORFs are used in the findBinders tool to generate a database of all peptides (typically 8, 9, 10, and 11mers of the peptides) predicted to bind to HLA alleles of interest, e.g., HLA-A02, HLA-A24, or HLA-A68. A tool called netMHCpan-4.0 [33] was used to predict MHC-I binding, but other tools are available, such as MHCflurry [34]

Accordingly, the peptides within the protein sequences that bind to the HLA genotypes in an individual patient or patient population can be identified. The findBinders script can run netMHCpan-4.0 or MHCflurry (or other tool) to generate a database of potential TE candidate cancer antigens. This database can be used to quantify HLA-peptide kmer expression in RNA-seq data.

At block 230, the peptides identified to bind to WIC (e.g., ones in the database at block 150) are used to predict corresponding RNA sequences that encode a peptide. This routine can in turn map the resulting RNA sequences back to particular locations in the genome that can be transcripted to the corresponding RNA. The duplicates can be resolved where each possible RNA kmer sequence is identified and used for measuring an expression level of the protein. Peptides predicted to bind to WIC can be mapped to transposable element ORFs using the TE sequence database.

Unique and multimapping DNA kmers can be used for quantifying expression of TEs from RNA-seq data. The vacKmer tool can be used to predict what mRNAs can encode the peptides and match the resulting kmer sequences to the transposable element loci that could have generated the particular peptide. This creates the genomic sequence database that can be used for quantifying transposable element expression in RNA-seq data.

At block 240, sequencing information from a sample can be analyzed to count the presence of RNA kmers, in order to determine an expression level for a corresponding protein. At block 240, the expression level of a particular protein can be compared to a baseline expression level for a healthy cell, and therefore used to detect a protein that is overexpressed in a tumor cell. The RNA kmers can be ranked by levels of overexpression. The highest ranked RNA kmers (e.g., top N (e.g., 10, 20, 30, etc.) or top X % (e.g., 5%, 10%, etc.)) can then be used to identify the cancer antigens, e.g., by in silico translation. The unique kmers can be mapped to identify the correct frame for translating to protein sequences. The mapping can identify the correct reading frame so that the kmer generates the protein sequence that would be generated by the DNA sequence of the TE. Descriptions herein of prediction and mapping can be performed using in silico techniques, which can model biochemical processes such as translation and transcription. Thus, such terms can refer to in silico techniques in the present context.

As an example, a list of kmers ranked in terms of RNA overexpression relative to a normal control can be produced (e.g., the top 100, 200, 300 kmers, etc.). The most highly ranked kmers might correspond to ones that are never expressed as proteins. For the ranking, a p-value can be generated using a distribution (e.g., a negative binomial distribution) for how overexpressed the kmer is relative to the normal control or cohort thereof. Thus, the element described in block 240 can filter out kmers that are likely to also be expressed as mRNA transcripts in normal cells. Other criteria can also be used (e.g., water solubility of the peptide corresponding to the over-expressed transcript) to determine the ranking of a particular candidate peptide for experimental validation. Furthermore, the MHC haplotype of a human subject can be determined for each sample, so the rank of the peptides can then be based on how likely they are to be presented by a patient of that MHC haplotype. Additionally, a distance (e.g., the hamming-distance) between the candidate cancer antigen and the closest normal protein antigen can be used as another criteria for prioritizing peptides that are strongly immunogenic.

When this analysis is performed for a particular individual or a particular cohort, an additional analysis can be used to confirm whether the subject is likely to respond to a vaccine. This analysis involves APOBEC genes.

APOBEC is a class of proteins/genes that protects the genome from transposable elements. Embodiments of the disclosed methods can use APOBEC mutation signatures as a secondary confirmation of overexpression of transposable elements. APOBEC can also be used to predict responsiveness to checkpoint blockade therapy. The usefulness of this approach is shown by the fact that overexpression of transposable elements can be correlated with response to immune-therapies.

Activation of the APOBEC antiviral response within cells is a hallmark of cancer [28,32]. The APOBEC family of proteins is also involved in repressing transposable elements through several mechanisms, including random mutagenesis of single-stranded RNA and DNA. To provide additional support to transposable element signal, a random mutagenesis database was generated using published APOBEC mutagenesis motifs [29,30,36]. The APOBEC mutation database along with the MHC bound TE peptides can be used for a complete analysis of expression signatures using the probeAnalysis tool. The probeAnalysis tool generates a ranked list of MHC bound peptides and APOBEC kmers for each sample. Analysis routines can annotate these lists for precision medicine applications.

APOBEC is active when transposable elements are active, but is otherwise inactive. One can then predict that when transposable element expression is high, higher APOBEC activity should result. APOBEC activity can be seen through very specific mutations in DNA and RNA, e.g., mutating a C to a T as an attempt to break the transposable element before reintegration into the genome. Thus, the RNA can be analyzed to detect mutations (e.g., more than a threshold) caused by the APOBEC pathway. For a given subject, if APOBEC is active, then there is a higher likelihood of identifying TE candidate cancer antigens specific for the subject. Whereas if APOBEC is off, then the likelihood is lower that the subject is a candidate for this type of therapy.

At block 205, a cancer patient's RNA-seq sequencing read file is downloaded, e.g., in FASTA format. The FASTA file provides the sequences of the RNA molecules obtained from the RNA sequencing of a biological sample from a subject, e.g., cells or a fluid.

At block 215, the APOBEC mutation binding sequence is identified in any of the RNA sequences. Activation of the APOBEC antiviral response within cells is a hallmark of cancer [28,32]. The APOBEC family of proteins is also involved in repressing transposable elements through several mechanisms, including random mutagenesis of single-stranded RNA and DNA. APOBEC3A is the most active APOBEC in cancer and is involved in repressing viral and retroelement reintegration events in the human genome. APOBEC3A causes a C>T substitution across the genome at the DNA-level, but Sharma et al. (2016) infra identified a secondary structure preference and a [CT][CT][ATC][TC]C[GA] binding motif preference. Similarly, APOBEC3G was recently found to preferentially bind to a N[CGT]N[CT])C motif.

At block 225, an inverted repeat structure is identified. Sharma et al. (2016) found that an inverted repeat was found in 98% of confirmed APOBEC3G mRNA edits due to a hairpin structure that facilitates APOBEC3G binding to RNA. The hairpin structure is found in the fasta file. Each potential mutation site will have this hairpin structure. It is a result of the RNA folding back on itself to form the hairpin shape that APOBEC can then bind to and mutate the sequence.

At block 235, an APOBEC3G kmer database was generated. The database can be used for comparison to the RNA sequencing data of a particular subject. The database can be generated synthetically on a computer, e.g., using the Gencode V32 transcriptome reference [42]. Synthetically mutated kmers containing these motifs were generated, filtering out kmers that match kmers in the normal transcriptome database as well as kmers related to common polymorphisms in the human population using the dbSNP resource [43]. The filtering is done since the detection of sequences that match regularly occurring sequences in the healthy population would not be associated with APOBEC activity.

Block 240 can use the sequencing results to count the occurrence of kmers (identified in block 230) corresponding to the identified peptides from block 220. Block 240 can also count the APOBEC kmers to estimate an APOBEC signature that has been found in tumor samples. The APOBEC signature can correspond to the number of kmers in the patient RNA-seq data that match a predicted APOBEC mutation generated in our database, which was generated in block 235. A reference distribution using healthy controls is used to estimate the threshold for activation of APOBEC. The threshold for an active APOBEC signature is identified using a reference cohort of healthy control RNA-seq fastq files, e.g., a specified number of standard deviations from the average of the reference cohort can be used.

Most bioinformatic tools actively ignore transposable elements because they are repetitive sequences that require special attention. As described above, the present disclosure includes a software suite that implements bioinformatic tools specifically designed for the unique challenges associated with transposable element analysis. Embodiments can include generation of a transposable element epitope database, locus-specific quantification of transposable elements, differential expression analysis, and identification of MHC-bound peptide in mass spectrometry data.

IV. METHOD OF IDENTIFYING CANCER ANTIGENS

As described above, some embodiments can identify candidate cancer antigens that may be used in a cancer vaccine. Such proteins may be highly expressed in cancer cells (e.g., on the surface of cancer cells), but not expressed or minimally expressed in healthy cells. Further, such proteins may be expressed in at least a subpopulation as opposed to being related to a specific mutation. Examples of such proteins are generated from transposable elements in the genome, e.g., short interspersed nuclear elements (SINEs) and long interspersed nuclear elements (LINEs), such as LINE-1 (L1) element L1 *Homo sapiens* (L1HS).

Figure 3:
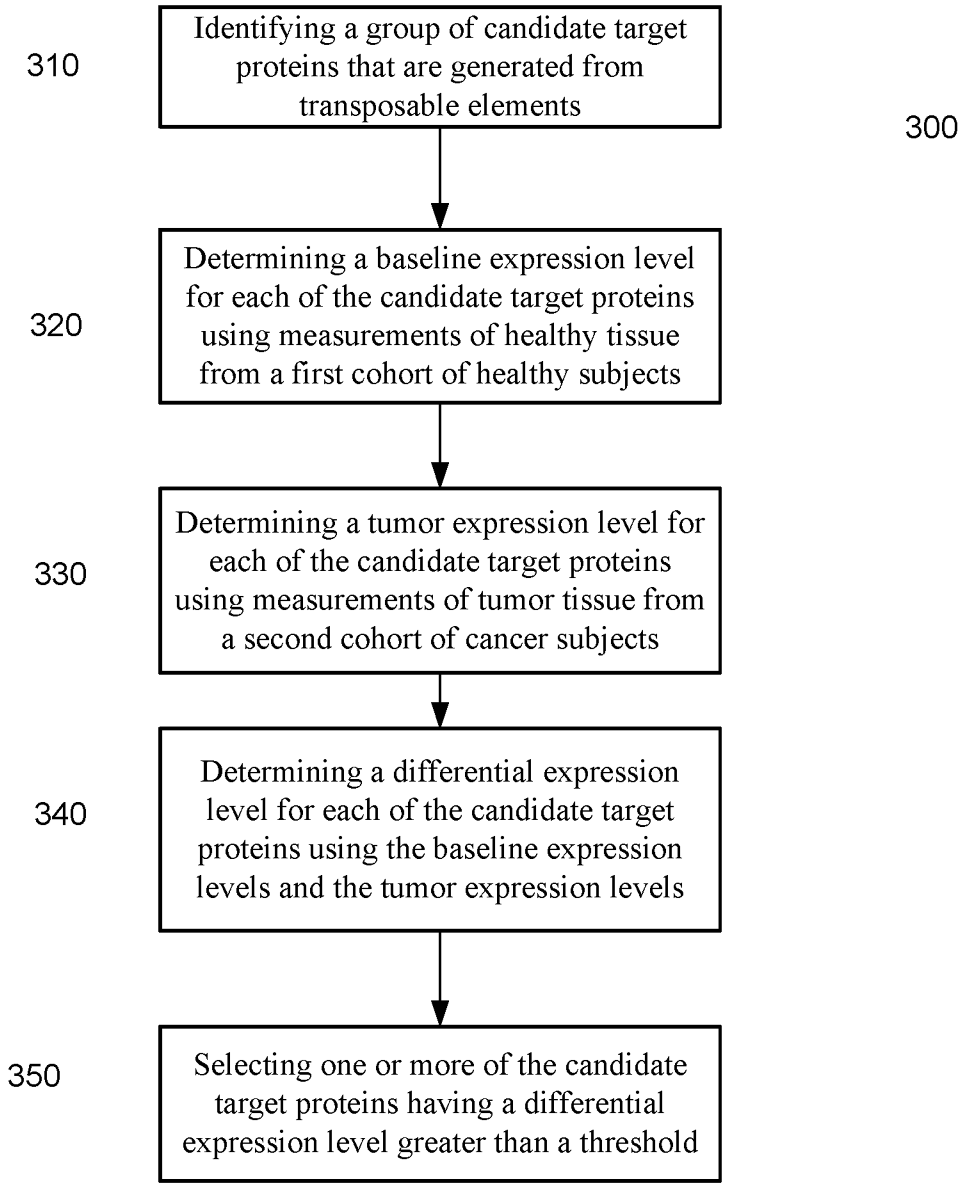
FIG. 3 is a flowchart illustrating a method for antigenic peptides for use in cancer treatment according to embodiments of the present disclosure.

FIG. 3 is a flowchart illustrating a method for identifying cancer antigens according to embodiments of the present disclosure. Method 300 and any of the methods described herein may be totally or partially performed with a computer system including one or more processors, which can be configured to perform the steps. Thus, embodiments are directed to computer systems configured to perform the steps of any of the methods described herein, potentially with different components performing a respective step or a respective group of steps.

At block 310, a group of candidate cancer antigens that are generated from transposable elements is identified. As an example, the initial identification of the candidate cancer antigens can be performed as described for FIGS. 1 and 2. At an initial stage, certain kmers (e.g., corresponding to RNA in open reading frames) may be identified, and the final identification of the cancer antigens can be performed after analyzing kmer occurrence in healthy and tumor samples. The group of candidate cancer antigens may be further filtered based on other criteria as described herein, e.g., that a peptide epitope of the protein binds to an MHC such as a class I MHC, e.g., a human HLA, which may be expressed by a particular subject or patient so that the peptide epitope can be presented to patient T cells in the subject.

The kmers can be identified first in ORFs in TE regions, with the protein corresponding to a given ORF being mapped to the unique kmers (e.g., identified by sequence and location) in the ORF. As another example, sequences of peptides that bind to MHC can be used to predict (e.g., via in silico reverse transcription) corresponding kmers that can be analyzed to determine an expression level of the candidate cancer antigen.

In some implementations, additional candidate cancer antigen can be identified, starting from an initial set. For a given peptide sequence, one can identify similar peptides that are known to be bound to MHCs, using machine learning approaches like net-MHC (Nielsen et al, *Protein Sci* 12, 1007-1017 (2003); incorporated by reference herein). Once those similar peptides are known, the peptide sequences can be used to identify corresponding RNA sequences that can in turn identify which of the transposable elements uniquely express those peptides.

At block 320, a baseline expression level is determined for each of the candidate cancer antigens using measurements of tissue from a first cohort of healthy subjects. The cohort can be of one or more subjects. In some implementations, a baseline expression level can be determined for kmers, and the expression analysis can occur in RNA space. Later, the expression levels for the kmers can optionally be used to determine a baseline expression level for corresponding proteins. As another example, the identified kmers can be translated to proteins. The expression level for the protein can be measured directly, e.g., using mass spectrometry. The baseline expression level can be determined for a particular tissue type, e.g., by analyzing a biopsy from the particular tissue type. In embodiments, the baseline expression level can be determined using measurements of non-cancerous tissue from the same subject.

In some embodiments, the baseline expression level can vary based on a subject's age, as the normal expression level for certain proteins can vary with age. The baseline expression level can also be determined for a particular tissue type, e.g., as method 300 may be implemented to identify candidate cancer antigens for a particular tissue type. Thus, the first cohort can have a particular age range and/or have tissue sample all from the same tissue type (e.g., breast, lungs, colon, liver, breast, prostate, etc.). The first cohort can also have a same or similar WIC haplotypes. A cohort can also share certain demographic information.

In other implementations, the expression levels of the proteins can be analyzed directly, e.g., using mass spectrometry. Whichever techniques are used, a tissue biopsy can be analyzed to perform the measurements. Alternatively, the analysis could use measurements performed by a different entity (e.g., published data), but which is still determined from healthy samples.

At block 330, a tumor expression level is determined for each of the candidate cancer antigens using measurements of tumor tissue from a second cohort of cancer subjects. The second cohort can have similar criteria as the first cohort, e.g., same age and/or tissue type. In one implementation, the tumor cohort comes from The Cancer Genome Atlas project, which includes publicly available data, with identifying characteristics to form various cohorts of samples. In another implementation, tumor samples from a subject can be analyzed, e.g., via RNA sequencing or mass spectrometry of proteins.

In some embodiments, the tumor expression level may be determined from measurements of the occurrence of various kmers. For instance, an expression level for a particular protein can be determined using measured amounts of various RNA kmers that can be translated to the protein. The amount of occurrence for each particular kmer (e.g., as measured via an intensity signal or by counting individual RNA molecules with the particular kmer), which can be translated to the protein, can be aggregated (e.g., a weighted sum) to determine the overall expression level for the protein.

The expression levels for kmers can be determined in various ways, e.g., using sequencing results or using sequence-specific probes, which can provide an intensity signal.

At block 340, a differential expression level is determined for each of the candidate cancer antigens using the baseline expression level and the tumor expression level. The differential expression level can be determined by comparing the tumor expression level to the baseline expression level. As examples, the comparison can include a ratio or a subtraction.

At block 350, one or more of the candidate cancer antigens having a differential expression level greater than a threshold can be selected. The proteins can be ranked based on a score that is dependent on the differential expression levels. As examples, the threshold can correspond to the N (e.g., 10) proteins having the highest differential or within a top range (e.g., by percentage) of differential expression levels. Constraints in synthesizing peptides/size may also be used in selecting candidate cancer antigens for the final library.

In some embodiments, the score can be further based on other criteria, such as chemical data like the solubility of the protein. For example, a hydrophobic candidate cancer antigen would be insoluble in water and would be unlikely to result in an effective cancer vaccine.

The comparison of the differential expression level to a threshold can be performed in RNA space. If a particular set of one or more kmers have expression levels above a threshold, the set of kmers can be mapped to the one or more of the candidate cancer antigens. The mapping can include finding the reading frame of a kmer within a transposable element. The mapping can also include identifying multiple kmers corresponding to a protein, and/or a single kmer coding for multiple proteins. Thus, there can be multiple mappings for a protein. Proteins can be grouped together, with pointers back to two locations in the genome that could have generated that protein. There can be different weights of a mapping between a kmer and a protein. The weights can be used to estimate a total expression of a particular protein by determining a weighted sum of the expression levels for each of the kmers mapped to the particular protein.

Depending on how the cohorts are defined, common targets can be identified for a broad range of subjects, e.g., as defined in a cohort. For example, candidate cancer antigens can be defined for a given tissue type for a subject within a particular age range. In this manner, the most common candidate cancer antigens can be identified, and vaccines based on these candidate cancer antigens can be administered. In other embodiments, a more personalized approach can be performed, using a specific measurement from a subject. For example, the measurements from a particular subject can be used to identify the highest ranked candidate cancer antigens for that subject, and vaccines based on those candidate cancer antigens can be administered. In another example, a determination of the subject's MHC haplotype can be used to identify higher ranked candidate cancer antigens for that subject.

Once the candidate cancer antigens are identified and ranked, vaccines can be designed and synthesized. For a personalized approach, the vaccines corresponding to the most highly overexpressed proteins for a particular subject can be selected for administration. Given that some candidate cancer antigens are shared across cohorts (particularly cohorts sharing one or more MHC alleles), vaccines can be predesigned and used for a matching patient.

V. IDENTIFICATION OF CANDIDATE TRANSPOSABLE ELEMENT CANCER

Embodiments (e.g., as described in FIGS. 1-3) can identify candidate cancer antigens corresponding to TEs, e.g., LINEs, such as L1Hs. L1HS sequences are rarely expressed. When they are expressed, there is a high likelihood that such expression correlates to genomic instability and cancer. And, because they are the youngest sub-class of LINEs evolutionarily, they are more likely to be shared across individuals because they came into the human genome relatively recently.

A. Generation of LINE-1 Epitope Database

The identification of the candidate cancer antigens can be performed as described for FIGS. 1-3. For example, at block 110 certain transposable elements can be identified. In some embodiments, the hg38 L1HS RepeatMasker annotation from the UCSC Genome Browser Table Browser tool (genome.ucsc.edu) can be used. The hg38 annotation contains 1,620 L1HS genomic loci.

As described for block 120, open reading frames were identified within each locus. A total of 11,129 unique open reading frames were found. Open reading frames were correlated to peptides (e.g., as is block 130), and the peptides were then screened for binding to the 81 most common HLA haplotypes using the netMHC-4.0 software [1]. This generated 60,842 unique 8, 9, and 10mer peptides predicted to bind to at least one HLA haplotype, e.g., as described in block 140. These peptides can be reverse transcribed to determine RNA kmers that may be analyzed for expression levels.

B. Relation Between Loci, Kmers, and Peptides

In the process of creating the database of candidate cancer antigens, some embodiments can identify regions (e.g., around particular loci) corresponding to TEs, identify kmers corresponding to those loci (where the kmers are DNA or RNA), and the kmers can be translated into peptides. Additionally, kmers correlating to DNA or RNA can be predicted from peptides that bind a particular WIC protein. For example, the peptides can be mapped to RNA kmers, which can then be used to measure expression levels. The determination of which kmers correspond to which peptides, and vice versa, is described herein as mapping.

Regarding mapping, a given kmer can map to two or more proteins. A given RNA sequence (open reading frame) generates one peptide, but a given kmer sequence can occur in different open reading frames, and thus a kmer can map to more than one protein. For example, if the kmer is located at two or more loci and each locus maps to a different protein, a kmer can map to two or more proteins. In such a case, the expression of the kmer can contribute to (e.g., split among) both of the proteins, e.g., using a weight determined for a given protein. The weight can be stored in the database and determined by the number of kmers that map to multiple TE loci. Besides expression levels for which proteins can be ranked, other criteria can be used, e.g., whether a protein is hydrophobic or other biochemistry criteria to select which protein is the better candidate cancer antigen.

Conversely, a given protein can map back to multiple locations in the genome. Such mapping can be done at block 150, e.g., to identify additional kmers corresponding to TEs. In such a case, each expression level of a kmer can contribute (e.g., as defined by a weight) to an overall expression for the protein to which the kmers can be translated.

Further, each transposable element can include multiple unique kmers. Thus, when doing the gene expression analysis, there can be multiple mappings to that unique locus (each mapping via a different kmer). The relative counts for each of those kmers (e.g., via a microarray or via RNA sequencing) can be used to estimate the overall expression of that unique locus, e.g., that translated to a same protein. Then, the expression levels of each locus mapping to a protein can be aggregated.

Accordingly, in some embodiments, selecting one or more of the candidate cancer antigens can including mapping a set of kmers to the one or more of the candidate cancer antigens.

C. MHC

The database of candidate cancer antigens can be sorted by major histocompatibility complex (MHC) haplotype. The cell packages the peptide into the MHC complex and moves the complex to the cell surface. This complex on the cell surface is what is recognized by the T cell receptor, resulting in T dependent immune responses.

Thus, a database that takes account of MHC haplotypes can be used to select candidate cancer antigens, by, for example, focusing on the MHC haplotype of a subject person. The MHC haplotype of a subject can be measured in various ways, e.g., by genotyping the DNA using a microarray or by DNA sequencing.

When using mass spectrometry, peptides can be purified after binding to MHCs. More particularly, a peptide library can be contacted with recombinantly produced peptide receptive MHC molecules bound to a solid surface, such as a column. Peptides that do not bind the peptide receptive MHC molecules flow through the column. Peptides that bind the MHC molecules are eluted and then can be identified using mass spectrometry. Then, the sequences of the eluted peptides can be matched to a transposable elements, e.g., using a database of predicted transposable element mass spectra, as may be determined using steps described in FIGS. 1 and 2, such as steps 140 and 220. Current mass spectrometry databases are not able to identify these peptides, but the method described here is able to identify MHC-bound peptides from tumor cells, which can be used to prioritize candidates for cancer vaccine therapies. Accordingly, determining the tumor expression level can comprise using mass spectrometry data from peptides eluted from MHC.

VI. DETERMINING EXPRESSION LEVELS

The expression of a transposable element can be measured in various ways, e.g., in RNA space or in protein space. In RNA space, certain sequences (referred to as kmers) can be quantified in cells of one or more tissue types, for both healthy and tumor tissues. The expression of a set of one or more kmers can be mapped to the expression of a particular protein, e.g., as a weighted sum. As noted above, certain kmers can contribute to more than one protein. In protein space, the expression measurements can be performed directly on the proteins. In some implementations, such measurements can be performed using mass spectrometry.

Figure 4:
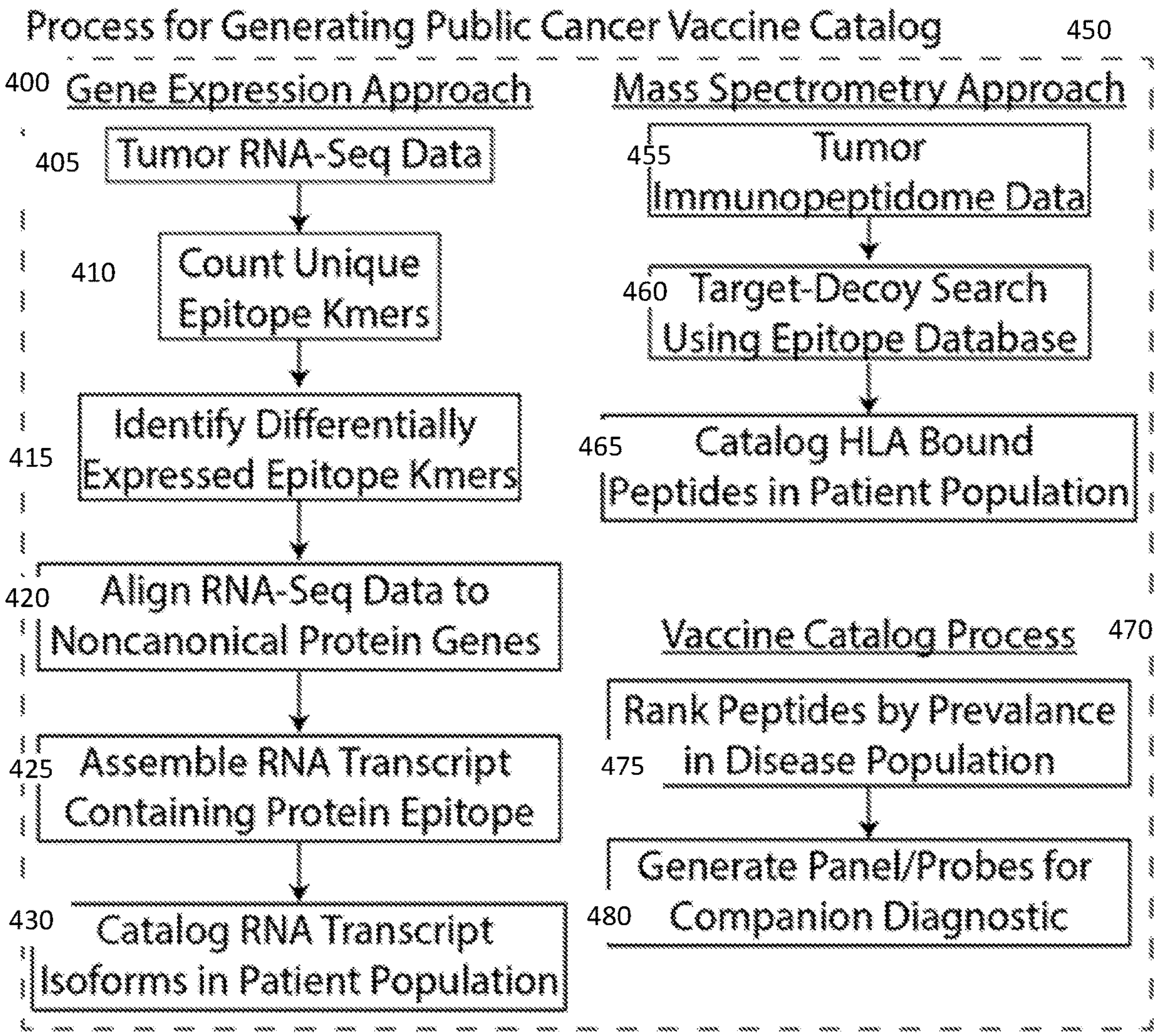
FIG. 4 shows a gene expression approach 400 and a mass spectrometry approach 450 for generating a vaccine catalog according to embodiments of the present disclosure.

FIG. 4 shows a gene expression approach 400 and a mass spectrometry approach 450 for generating a vaccine catalog according to embodiments of the present disclosure.

A. RNA

Accurate identification and quantification of transposable elements can use locus-specific sequences. The repetitive nature of L1HS and other transposable elements leads to multimapping of sequence reads, where a read can map to several locations in the genome. In some embodiments, to address the multimapping, embodiments can quantify the expression of locus-specific sequences. The locus-specific sequences can be unique. To be unique, the sequences (kmers) are (in general) relatively long (e.g., 20-30mers). In other embodiments, multimapping is addressed by having various kmers contribute to the protein generated from each locus.

Although not required, uniqueness may be used as a feature for identifying loci that have a particular relationship to cancer. For example, gene fusion events can occur in some cancers (Ph+ Leukemia) where two chromosomes break and merge together to form a new chromosome. This causes the regulation of these chromosomes to change and may result in the generation of TE peptides that are unique to a particular locus. By focusing on unique kmers, these loci can be identifies. But if uniqueness was not enforced, then we may identify TE sequences that are expressed at several loci in the human genome.

Embodiments can then determine if the expression of a kmer is statistically different compared to a reference dataset of control gene expression data across human tissues and developmental stages. The comparison of expression can occur on a per tissue and/or per developmental stage basis. The resulting differential expression levels for the candidate cancer antigens can be used to select vaccines. When the baseline expression level is determined for a particular tissue, a personalized expression threshold for differentially expressed transposable elements can be determined for the subject's specific tumor, e.g., in block 320 of FIG. 3.

The quantification analysis can use reads from part or all of an RNA fragment. In a clinical setting, one may want to confirm the presence of the entire transcript sequence, which can be done by assembling the whole sequence from the fragments. This can be done by aligning the RNA-seq reads to the reference using bwa [Grabherr M. et al. "Full-length transcriptome assembly from RNA-Seq data without a reference genome," Nat Biotechnol. 2011 May 15; 29(7):644-52] and assembling the full length transcript using the trinity software [Li H. and Durbin R., "Fast and accurate short read alignment with Burrows-Wheeler transform," Bioinformatics 2009 Jul. 15; 25(14):1754-60].

One challenge of quantifying the expression of TE is that they are very repetitive. Software techniques described herein can find unique kmers, which can be used as a barcode to identify specific transposable element sequences that are candidate cancer antigens. By querying across the genome and analyzing expression data (e.g., overexpression of TE kmers in the RNA transcriptome), the database of reference normal samples can be used to isolate the tumor specific overexpression of transposable elements. Embodiments can rank those peptides by any of a number of factors, including, a score determined over expression of the kmer relative to normal tissue, water solubility, ability to be presented by a subject's MHC alleles, as well as other factors mentioned herein. The result of the analysis is a list of potential vaccine peptides for use in cancer therapy. These can be used alone or in combination with another therapy such as checkpoint blockade therapy. The unique kmers can correspond to the length of the peptides and be on the order of 24, 27, or 30 bases long.

Referring back to the gene expression approach 400 of FIG. 4, block 405 receives RNA expression data from, as exemplified in approach 400, RNA sequencing of tumor tissue. Various techniques for obtaining the RNA expression data can be performed, as will be appreciated by one of skill in the art.

At block 410, the occurrence of each of the unique epitope kmers can be counted. Each of the sequence reads can be compared to the library of kmers (e.g., as determined according to FIG. 1) for the TEs. The expression level for each of a plurality of candidate cancer antigen kmers can be quantified in various ways, e.g., as a ratio to a total number of sequence reads, to a control sequence that is common across tissue types, or via other normalization techniques. Normalization can be used for comparing across multiple subjects, but is not needed for prioritizing for a particular subject.

At block 415, differentially expressed kmers are identified by comparing to reference levels determined from normal tissue. As described herein, the reference levels can be determined on a per tissue basis and/or on a developmental age basis, as well as other factors. Kmers that have a sufficiently high differential expression can be identified and used for later blocks.

At block 420, the RNA sequencing data is aligned to noncanonical protein-coding genes inferred from transposable element sequences. The kmers that are highly overexpressed can be aligned to the noncanonical protein genes (e.g., in TE elements), e.g., as part of filtering out kmers that do not align to noncanonical protein genes. Overlapping reads aligning to inferred TE reference sequences can be assembled to recover full-length transcript sequences.

At block 425, RNA transcripts containing a candidate cancer antigen (termed a "protein epitope" in FIG. 4) are assembled. The kmers that contribute to a particular candidate cancer antigen can be identified as a group, thereby identifying a cancer antigen epitope that is differentially expressed in cancer.

At block 430, the RNA transcript isoforms are catalogued in the patient population. Blocks 420-430 can quantify the most abundant hits across patients to create a short list of the most widely used cancer antigens for vaccine production. This step can build a growing database of the most common hits.

B. Proteins—Mass Spectrometry Approach for Identifying Candidate Cancer Antigens from TE Peptides Certain mass spectrometric approaches rely on protein databases for identifying peptides. One of the limitations of such approaches is that peptides that are not present in the search database are not identified. Since the focus in the field has been on the identification of canonical proteins, there has been limited attention paid to potential cancer antigens from non-canonical protein coding genes, including genes within transposable elements. Disclosed herein is a novel approach for identifying potential cancer antigens by first precomputing a database of transposable element epitopes using the vaccinaTE software, e.g., as described in FIGS. 1 and 2. A mass spec peptide search database from the Immune Epitope Database (IEDB) of known MHC bound peptides and the predicted L1HS peptides was also generated. The MaxQuant software [45,46] was then used to identify these peptides in publically available MHC peptide profiling data for a cohort of triple negative breast cancer patients (PRIDE accession: PXD009738).

The mass spectrometry database of peptides from TE elements can be used to detect the expression levels by matching spectra patterns for the peptides in the database. The intensity of the peaks can provide the expression level for the protein. Certain TE peptides are not only overexpressed in cancer cells but are actually presented on the cell surface of real triple negative breast cancer patient tumors.

Referring back to the gene expression approach 400 of FIG. 4, block 455 measures tumor immunopeptidome data. The large collection of peptides associated to human leukocyte antigens (HLA) is referred to as the human immunopeptidome. The proteins can be isolated by performing an acid wash that releases the MHC bound peptides from the cell surface. [Bassani-Sternberg, M. "Mass Spectrometry Based Immunopeptidomics for the Discovery of Cancer Neoantigens," Methods Mol Biol. 2018; 1719:209-221]. Mass spectrometry was used to measure the expression of such peptides.

At block 460, a target-decoy search is performed using an epitope database as described in, for example Elias J E and Gygi S P, Methods Mol Biol 604, 55-71 (2010); incorporated by reference herein. This search corresponds to a process of creating real peptide spectra and fake peptide spectra and determining if a mass spectra matches the real peptide more often than the fake peptide.

At block 465, a catalog of HLA bound peptides is identified in the patient population. As a result, the most prevalent peptide sequences can be catalogued. Embodiments can then move forward with synthesizing those most widely seen peptides.

C. Vaccine Catalog Process

After the expression levels are measured, the candidate cancer antigens can be identified.

At block 475, the peptides can be ranked by the prevalence in the disease population. The prevalence is based on the RNA expression data or data derived from direct peptide quantification (e.g., mass spectrometry). The ranking of the expression provides the peptides that occur more frequently in cancer cells, but not in healthy cells. Techniques for ranking are described herein.

At block 480, a panel of nucleic acid probes can be generated for use companion in diagnostics. Such an approach can accelerate the identification of candidates for the vaccine therapy. Once there is a ranked set of peptides, nucleic acid probes that detect the presence of these candidate cancer antigens in tumors can be generated. The probes can be used to screen patients who are likely to benefit from treatment with the peptide vaccine.

D. Generation of APOBEC Kmer Database

Besides quantifying kmer expression, embodiments can analyze APOBEC mutations. The ability to quantify APOBEC associated RNA editing/DNA mutations was investigated using RNA-seq data as input. This is a novel approach that uses in silico mutated transcriptome kmers to detect heightened APOBEC activity, which is a sign of viral infection and TE expression, and is an independent predictor of response to checkpoint blockade therapy [39,40]. The heightened activity was measured by comparing APOBEC RNA sequences in tumor tissue and in healthy tissue ("The Genotype-Tissue Expression (GTEx) project," Nat Genet. 2013 June; 45(6):580-5).

APOBEC3A is believed to be the main enzyme responsible for the cancer APOBEC signature [28,31,36,41]. These enzymes are typically studied for their DNA mutagenesis signature, but APOBEC3A and 3G were recently found to have an RNA signature that is more specific than the C>T DNA mutagenesis signature. These APOBEC enzymes bind to a specific RNA secondary structure (used as a probe) that can be computationally modeled to detect APOBEC activity from RNA-seq data. The binding motif for APOBEC proteins can be used to make probes to detect APOBEC mutations in RNA, where the probes detect RNA expression of sequences with APOBEC mutations. This biological signature can be used to identify patients who may benefit from checkpoint blockade therapy.

APOBEC3A is the most active APOBEC in cancer and is involved in repressing viral and retroelement reintegration events in the human genome. APOBEC3A causes a C>T substitution across the genome at the DNA-level, but Sharma et al. (2016) identified a secondary structure preference and a [CT][CT][ATC][TC]<u>C</u>[GA] binding motif preference, which is an RNA sequence that binds to RNA in a tumor sample. Similarly, APOBEC3G was recently found to preferentially bind to a N[CGT]N[CT])<u>C</u> motif. Sharma et al. (2016) found that an inverted repeat was found in 98% of confirmed APOBEC3G mRNA edits due to a hairpin structure that facilitates APOBEC3G binding to RNA. Using the Gencode V32 transcriptome reference [42], kmers were synthetically mutated to contain this motif, filtering out kmers that match kmers in the normal transcriptome database as well as kmers related to common polymorphisms in the human population using the db SNP resource [43]. For example, one can start with the reference transcriptome and remove the variants that are in the human population, and then computationally mutate the sequences using the RNA sequence that APOBEC proteins bind to. These mutated sequence can then be used to measure APOBEC activity indirectly using the mutation patterns APOBEC makes when active.

Figure 13:
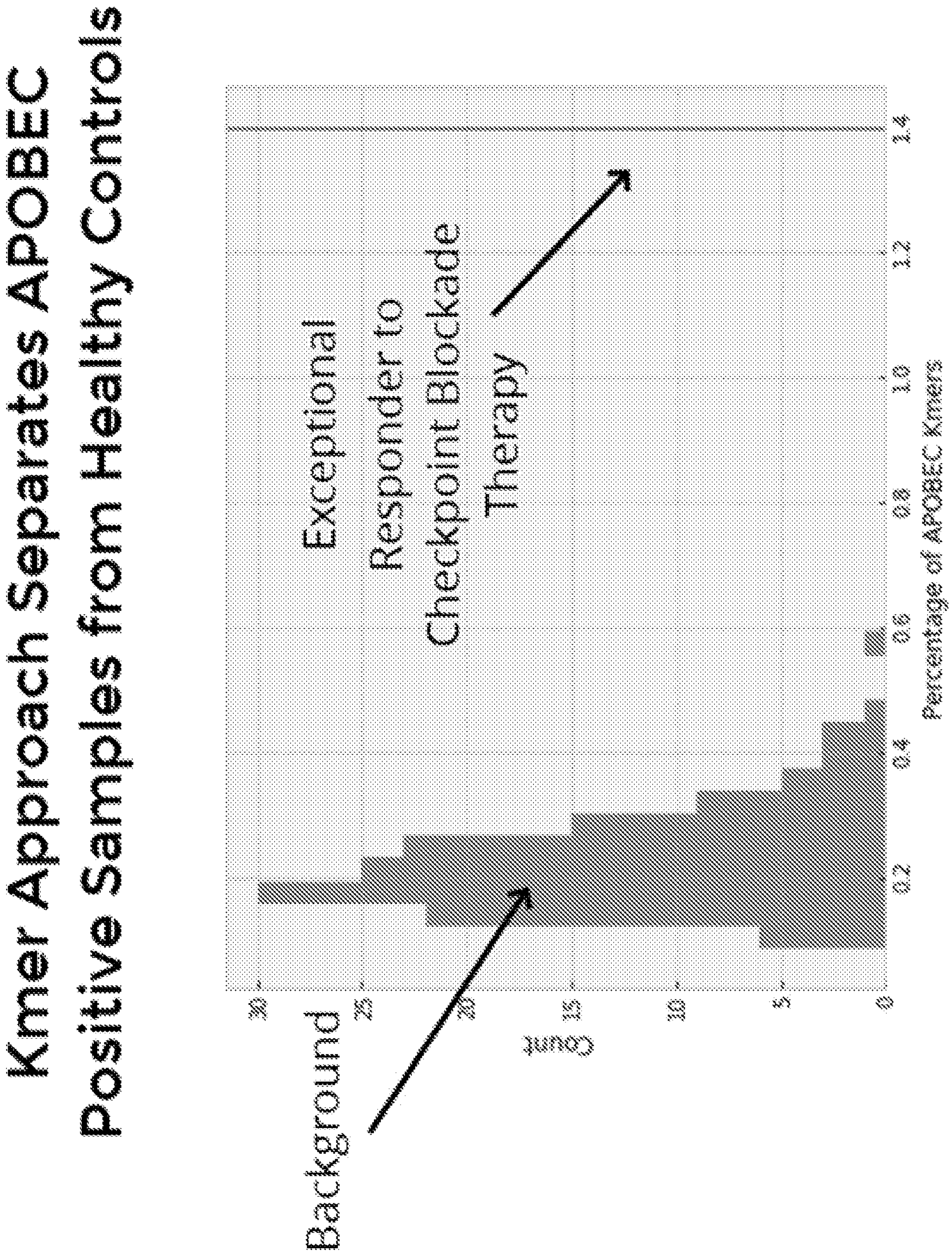
FIG. 13 shows a plot illustrating an example threshold for APOBEC measurements to indicate an exceptional response to checkpoint blockade therapy according to embodiments of the present disclosure.

Some implementations can then use the kmerCounter script to quantify the number of mutated and normal kmers in RNA-seq samples. The number of normal kmers can be used as a normalizing factor to account for biases in library depth. For example, if you sequence more, you may identify more reads, more errors, etc. Normal background expression can be used to subtract out noise. FIG. 13 shows a plot illustrating what value predicts response.

VII. SELECTING PATIENT-SPECIFIC ANTIGEN AND VACCINE

Embodiments can create a repository of presynthesized validated vaccines, which would be applicable to a significant number of individuals, as they focus on TE sequences that are not mutated but are differentially expressed. For a given individual, measurements can be made to determine which of the preselected panel of proteins/kmers are overexpressed, and then use the corresponding vaccines. One or more vaccines can be used in combination.

A. Method of Identifying Personalized Vaccine

Figure 5:
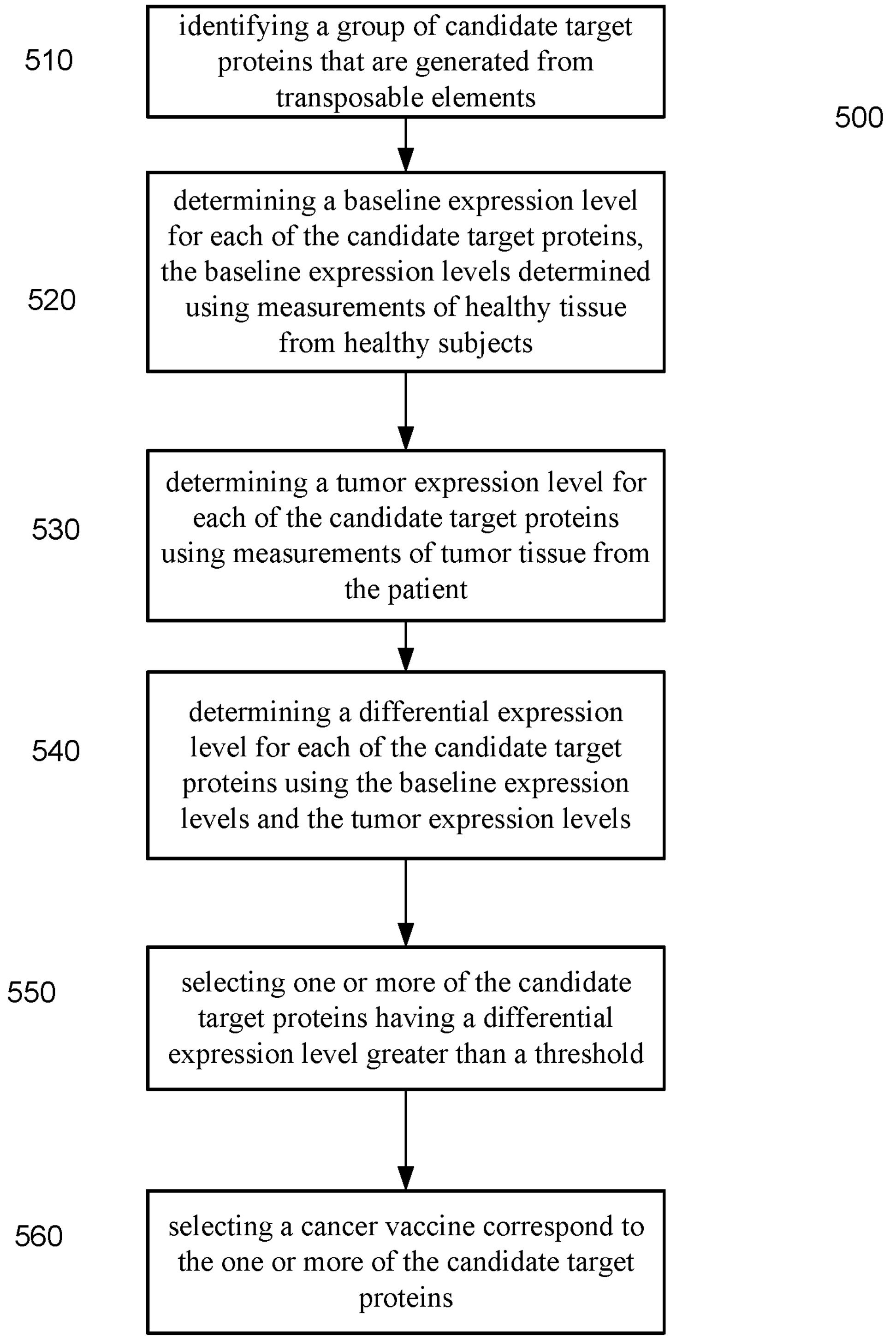
FIG. 5 is a flow chart illustrating a method 500 for identifying a cancer vaccine for a patient according to embodiments of the present disclosure.

FIG. 5 is a flow chart illustrating a method 500 for identifying a cancer vaccine for a patient according to embodiments of the present disclosure. Method 500 can be applied to each individual to find the patient-specific over expression of these antigens in the library, e.g., as determined using FIGS. 1-3.

At block 510, a group of candidate cancer antigens (referred to as candidate target proteins in FIG. 5) is identified that are generated from transposable elements. These group of candidate cancer antigens can be identified as described herein and may be shared across a cohort of patients, e.g., with a same type of cancer (e.g., of a same organ) or of patients that share one or more HLA alleles in common. In results below, we found significant overlap of these cancer antigens across indications but not in normal tissue. The cancer antigens that are shared across tissue types can be ranked highest.

At block 520, a baseline expression level is determined for each of the candidate cancer antigens. The baseline expression levels can be determined using measurements of healthy tissue from one or more healthy subjects. A baseline level can include a distribution of levels from the healthy tissue, which can provide information about the likelihood of a measured expression level being from healthy tissue. As an example, a certain number of standard deviations can be used as a cutoff to discriminate between a normally expressed and overly expressed.

At block 530, a tumor expression level is determined for each of the candidate cancer antigens using measurements of tumor tissue from the patient. The tumor expression level can be determined in various ways, e.g., as described herein. Non-tumor tissue can be collected along with the tumor tissue (e.g. tumor adjacent tissue) and expression levels in that non-tumor tissue can be measured to provide the baseline expression level.

At block 540, a differential expression level is determined for each of the candidate cancer antigens using the baseline expression levels and the tumor expression levels. The differential expression level can be determined in various ways, e.g., as described herein.

At block 550, one or more of the candidate cancer antigens having a differential expression level greater than a threshold are selected. These candidate cancer antigens would be ones that are overly expressed in the patient.

At block 560, a cancer vaccine corresponding to the one or more of the candidate cancer antigens is selected. In this manner, embodiments can determine which vaccine to use alone or in combination. For example, there may be 5-10 highly ranked candidate cancer antigens identified, and their corresponding vaccines can be used in combination.

In some implementations, an expected efficacy can be measured. For example, an expected efficacy of the cancer vaccine can be determined based on APOBEC activity in the tumor tissue. APOBEC activity can be measured by determining an amount of RNA molecules having an APOBEC mutation signature, e.g., as disclosed herein.

B. Microarray

In some embodiments, microarray technology can be used to detect the tumor expression levels for a subject for determining which vaccine(s) to use. The microarray would include probes (e.g., nucleic acids) that bind to the cancer antigens/RNA in the candidate library. A biopsy from the patient can be used to prepare the sample for use with the microarray. The expression levels for the proteins can be compared to the reference levels to determine which proteins are most highly overexpressed, e.g., as described for FIG. 5.

Figure 6A:
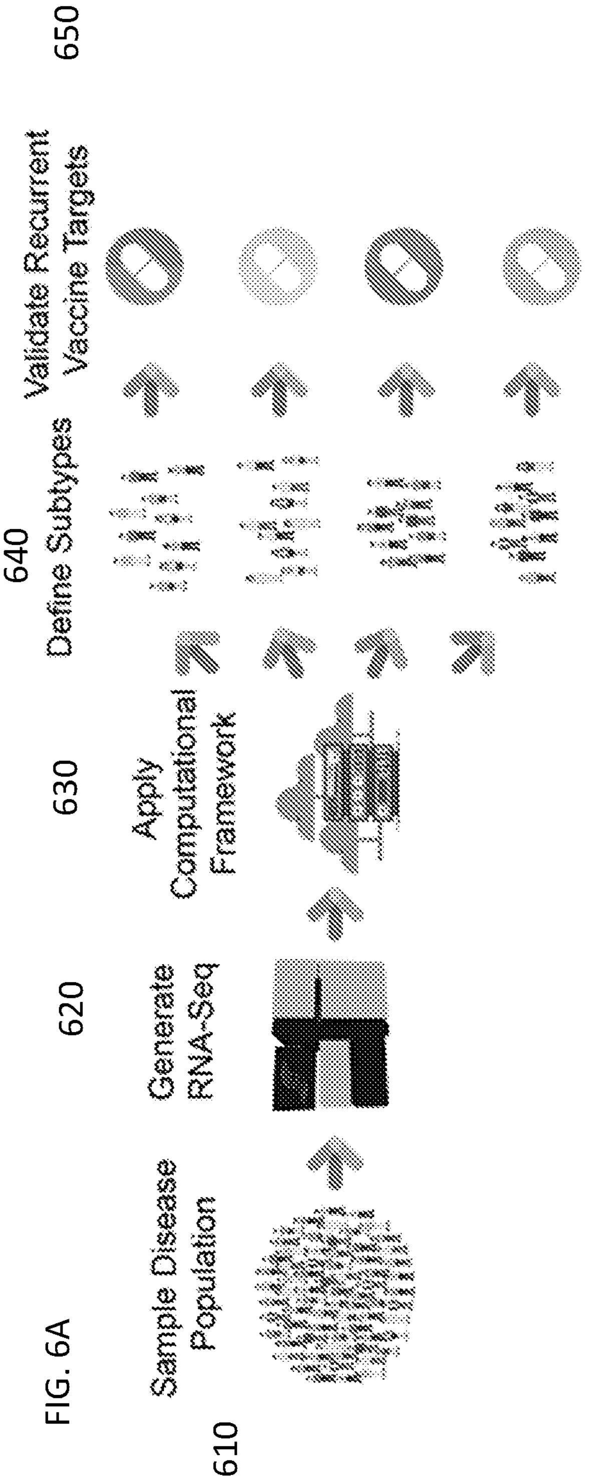
FIG. 6A illustrates the identification of the candidate cancer antigens according to embodiments of the present disclosure.
Figure 6B:
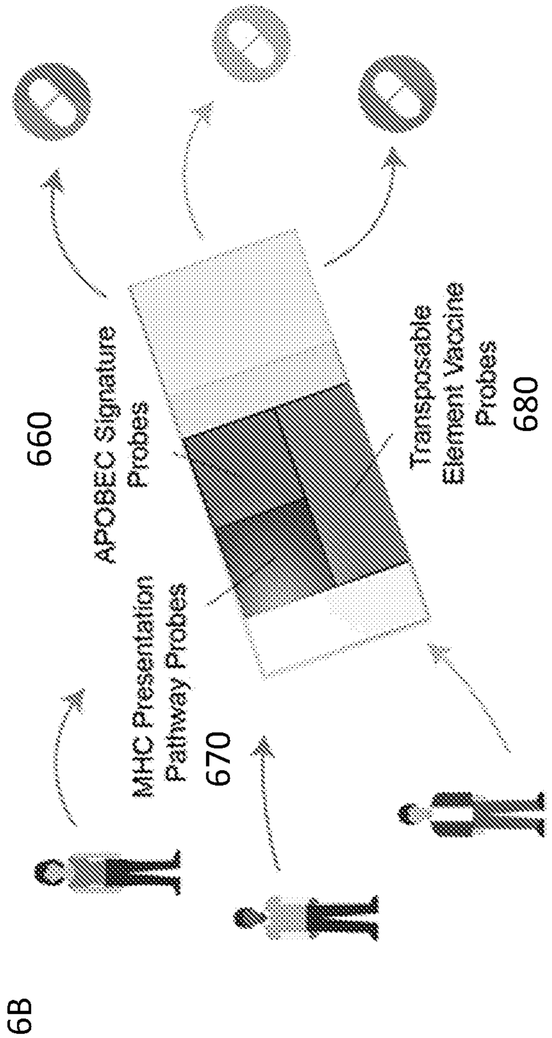
FIG. 6B shows a microarray for use in determining vaccines to provide to a subject according to embodiments of the present disclosure.

FIGS. 6A and 6B show a process for prioritizing shared TE candidate cancer antigens and matching patient tumor samples to repository of validated vaccine therapies according to embodiments of the present disclosure. FIG. 6A shows a process for screening cancer RNA-seq data and defining subtype groups based on shared TE epitope expression. Thus, FIG. 6A illustrates the identification of the candidate cancer antigens according to embodiments of the present disclosure.

At block 610, samples are obtained from the disease population. The disease population can be a subpopulation having particular characteristics, e.g., cancer of a same tissue type, of a same age and other demographic information, similar HLA type, and other characteristics described herein.

At block 620, RNA sequencing data is generated from the samples. One will appreciate the various RNA sequencing techniques that can be used. As an alternative, direct protein measurements can be performed, e.g., mass spectrometry.

At block 630, a computational framework as described herein is applied to detect TE proteins (e.g., L1HS) that are overexpressed. Such a computational framework can determine an expression of TE proteins on a surface of the cancer cells and compare the measured expression to a baseline expression expected in healthy cells.

At block 640, patients that coexpress these L1HS candidate cancer antigens are identified. In this manner, the candidate cancer antigens that occur often in the population can be identified. Since these candidate cancer antigens occur in a significant portion of the selected population (e.g., as determined by a threshold, such as 5%, 10%, or 20%), it is likely that a new patient will have the same cancer antigen overexpressed. Each subtype can have a same cancer antigen overly expressed.

At block 650, candidate cancer antigens are validated clinically. This step can take the vaccines that are shared within a group of patients and develop them into therapies. Testing can be performed for safety and efficacy in model organisms and human subjects.

FIG. 6B shows a microarray for use in determining vaccines to provide to a subject according to embodiments of the present disclosure. The microarray correlates TE expression with MHC presentation and APOBEC expression signatures. Transposable element vaccine probes 680 that detect the candidate cancer antigens can be printed onto a microarray, which can also include MHC presentation pathway probes (670) and APOBEC signature probes (660). Depending on the intensity of the signals from the probes, it can be determined which candidate vaccines to select for treatment The APOBEC signature probes 660 can be used to determine whether the subject would be responsive to certain vaccines, e.g., as a high level of APOBEC activity can be used to confirm that TE overexpression is present. Probes 660 can be used as an orthogonal signal to help guide the identification of the appropriate treatment for the patient.

MHC presentation pathway probes 670 can quantify the expression of MHC molecules so as to determine which MHC haplotype is present. Further, downregulation of MHC associated genes can be correlated with progressive disease. Patients who have downregulation with MHC tend to not respond to checkpoint blockade. If this patient has downregulation of MHC, an additional immune therapy that increases the MHC expression can be used. An option is to increase the expression using a cytokine like interferon gamma (Garrido, F. at al., The urgent need to recover MHC class I in cancers for effective immunotherapy, Curr Opin Immunol. 2016 April; 39:44-51).

In some embodiments, a microarray can comprise a first array of nucleic acid probes (e.g., 680) that hybridize to cDNA from transposable elements in a human genome. The first array of nucleic acid probes can includes one or more sequences from table 2 of the Appendix, which provides RNA sequence probes from various L1HS loci. Each row of table 2 provides a sequence, along with Class, Chromosome, Start Index, Stop Index, Strand, ORF, and Peptide Start Index. The class is L1HS for each of the sequences in table 2, but other classes of transposable elements can be used. The start and stop index refers to where the TE starts and stops in the genome. The strand refers to which strand is the sense strand for the TE, i.e., +/−. The ORF is the open reading frame within this locus. The Peptide start index refers to where in this ORF the peptide in question starts. The first array can include at least any 5, 10, 15, 20, 25, 30, 35, 40, 45, or 50 sequences from the list. In some implementations, the first array includes probes that include at least the five sequences:

```
                                    (SEQ ID NO: 1)
TACGTTAGACCTAAAACCATAAAAACCCTAG,

                                    (SEQ ID NO: 2)
AATTCAAGATGGATTAAAGATTTATACGTTA,

                                    (SEQ ID NO: 3)
AAAGATTTATACGTTAGACCTAAAACCATAA,

                                    (SEQ ID NO: 4)
TCAAGATGGATTAAAGATTTATACGTTAGAC,
and

                                    (SEQ ID NO: 5)
CAAGATGGATTAAAGATTTATACGTTAGACC.
```

The microarray can further comprise a second array of nucleic acid probes (e.g., 670) that hybridize to cDNA corresponding to genes involved in processing antigens for presentation on MHC molecules. These probes can test for defects in the pathway, which is a common mechanism for cancer cells to evade immune recognition. The second array of nucleic acid probes can include one or more sequences from table 3 of the Appendix, which provides RNA sequence probes for detecting different MHC alleles. Each row of table 3 provides the sequence and a name of a gene in the MHC presentation pathway. These genes were found to be differentially expressed between responders and non-responders to checkpoint blockade therapy. The genes are as follows: ERAP1: Endoplasmic Reticulum Aminopeptidase 1, ERAP2: Endoplasmic Reticulum Aminopeptidase 2, TAP1: Transporter 1: ATP Binding Cassette Subfamily B Member; TAP2: Transporter 2, ATP Binding Cassette Subfamily B Member; B2M: Beta-2-Microglobulin, HLA-A: Major Histocompatibility Complex, Class I, A; HLA-B: Major Histocompatibility Complex, Class I, B; HLA-C: Major Histocompatibility Complex, Class I, C; HLA-E: Major Histocompatibility Complex, Class I, E; and HLA-F: Major Histocompatibility Complex, Class I, F. The second array can include at least any 5, 10, 15, 20, 25, 30, 35, 40, 45, or 50 sequences from the list. In some implementations, the third array includes at least one probe for each of the four genes: TAP1, ERAP1, B2M, and HLA-A.

The microarray can further comprise a third array of nucleic acid probes (e.g., 660) that hybridize to cDNA corresponding to RNA transcripts that have been mutated by the APOBEC proteins. APOBEC activity is a marker of transposable element activation and correlates with response to immunotherapy. The third array of nucleic acid probes can include one or more sequences from table 4 of the Appendix, which provides RNA sequence probes for detecting APOBEC mutations. These probes are labeled as determined by a synthetic mutational techniques, e.g., as described herein. The third array can include at least any 5, 10, 15, 20, 25, 30, 35, 40, 45, or 50 sequences from the list. In some implementations, the third array includes probes that include at least the five sequences:

```
                                    (SEQ ID NO: 6)
TCGCCTCCTAAAGTGCTGGGATTACAGGCGT,

                                    (SEQ ID NO: 7)
GATCTCTTGACCTCGTGATCCACCCTCCTTG,

                                    (SEQ ID NO: 8)
CCTCTGCCTCCTGGGTTTGAGCAATTCTCCT,

                                    (SEQ ID NO: 9)
AAGTGCTAGGATTACAGGCGTGAGCCTCTGC,
and

                                   (SEQ ID NO: 10)
CTAACAGTGAAACCCTGTCTCTACTAAAAAT
```

VIII. RESULTS

A. Creation of LINE-1 Peptide Kmer Database and APOBEC Signature

Figure 7:
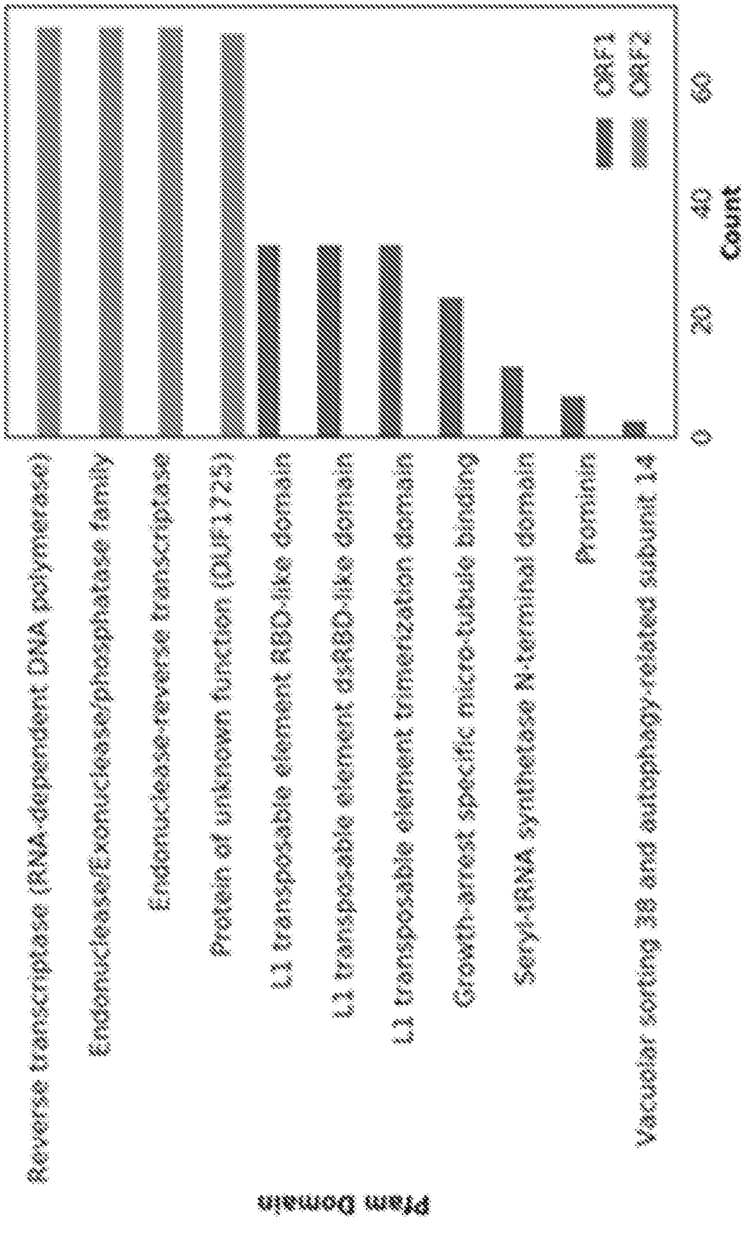
FIG. 7 shows a predicted L1HS open reading frames contain expected protein coding domains according to embodiments of the present disclosure.

In order to quantify the expression of L1HS and APOBEC antigen signatures in healthy and cancer tissue samples, a database of kmers was generated using the Gencode V32 genome and transcriptome reference files and the L1base 2.0 annotation for full length L1HS elements and L1HS elements with intact ORF2 sequences [37,42]. This resulted in the generation of 38 unique ORF1 sequences and 56 unique ORF2 sequences. These ORF sequences were then analyzed for conserved protein domains using the Pfam software [38]. We found that ORF1 contained conserved LINE-1 domains, including the L1 RNA Binding Domain (RBD)-Like domain, the double stranded RBD-like domain, and the L1 trimerization domain (FIG. 7). FIG. 7 shows that the open reading frames that corresponded to the transposable element sequences correspond to known domains within L1HS open reading frames. ORF2 contained the endonuclease domain, the reverse transcriptase domain, and the domain of unknown function.

FIGS. 8A-8D show an overview of the general properties of the open reading frames in terms of MHC bound sequences according to embodiments of the present disclosure. The overview provides features of the L1HS peptides, including basic statistics about the peptides and where they are in the reference L1HS sequence.

Figure 8:
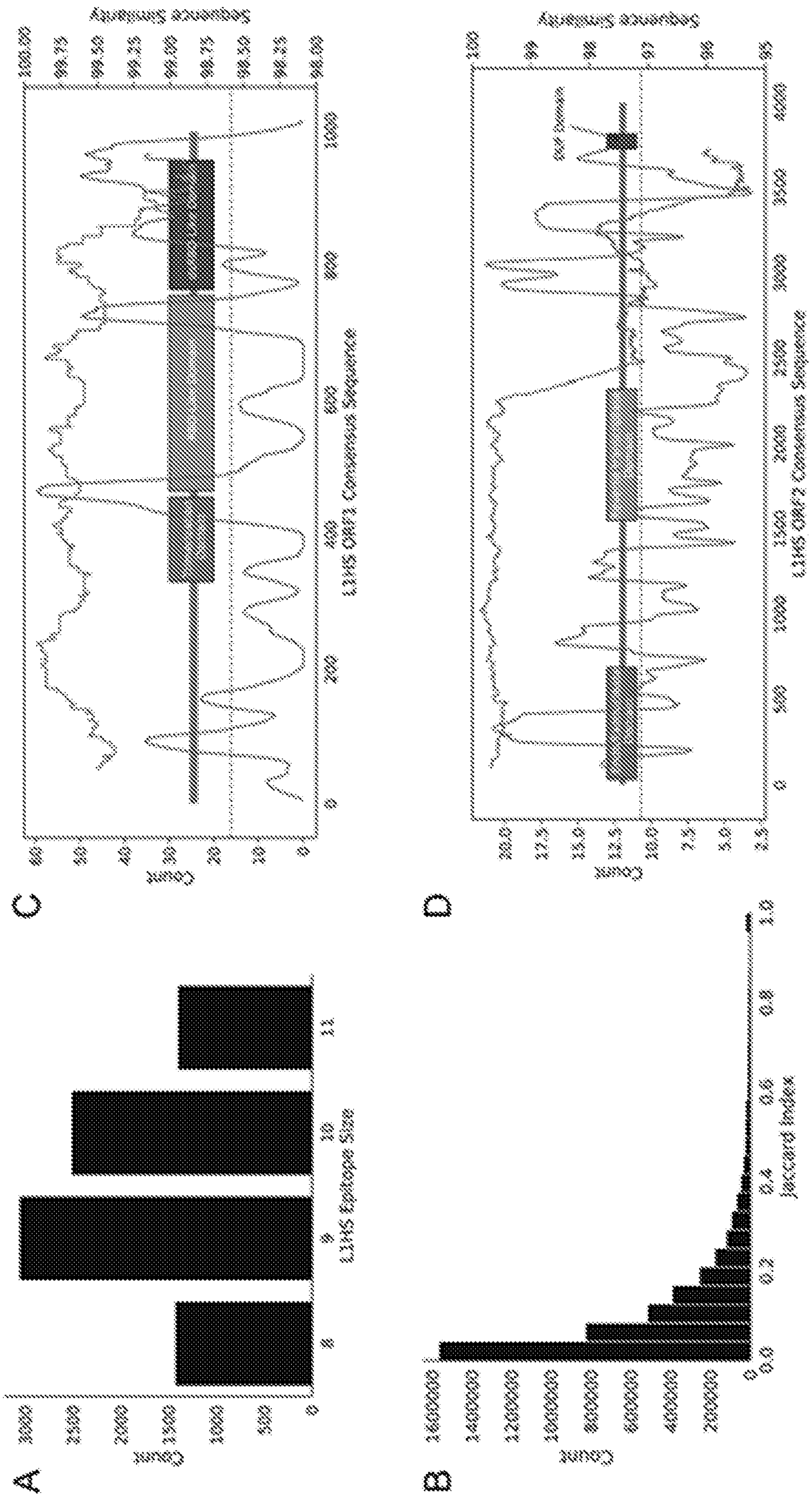
FIGS. 8A-8D show MHCI binding prediction identifies large number of L1HS candidate cancer antigens according to embodiments of the present disclosure.

FIG. 8A shows a barplot of netMHCpan-4.0 predicted L1HS epitope lengths. FIG. 8A shows the distribution of the epitope lengths. We searched for 8 mers to 11 mers and found a maximum around 9 and 10 mers, which correspond to the DNA sequence that are related to the particular proteins at the L1HS sites.

FIG. 8B shows a histogram of Jaccard similarity index values for pairwise comparison of 2,427 HLA alleles. The Jaccard index is a measure of how similar our two sets are. In this instance, the similarity can be considered as follows: considering all of the HLA haplotypes, quantifying them, and making a set of all of the epitopes that bind to those haplotypes, FIG. 8B is the distribution of their overlap (e.g., as a percent overlap). FIG. 8B shows that HLA is a very diverse region of the human genome.

FIG. 8B shows that the MHC haplotypes do not bind to the same set of epitopes. In fact, there is a relatively low overlap between any two HLA types. Across all of the L1HS loci, there is relatively low overlap across all the MHC haplotypes. Thus, each haplotype has a somewhat unique set of peptides that are associated with the L1HS. But, one would be able to reuse vaccines for other people having the same MHC (HLA).

FIGS. 8C and 8D are coverage plots for predicted MHC Class I binding peptides across consensus L1HS ORF1 and ORF2 sequences. Protein domains were annotated using Pfam software. Protein domains were annotated using Pfam software. The plots are across all L1HS loci in the reference human genome. L1HS has two open reading frames corresponding to two different regions within the L1HS genome. ORF 1 is gene 1 and ORF 2 is gene 2. One encodes a localization factor that takes the L1HS genome and brings it to the human genome. The second encodes the machinery needed to copy all the L1HS genome and insert it into the human genome.

The red line corresponds to the sequence similarity across an L1HS ORF multiple sequence alignment. The sequence similarity is across other L1HS regions of the genome. In the first open reading frame in FIG. 8C, the sequence similarity is pretty high. The similarity trails off in the end, but in ORF 2, there is a dramatic decrease in the sequence similarity towards the end. This is expected because one of the defense mechanisms in the cell is to mutate the three prime ends so the downstream end of the gene breaks. Thus, we would expect more mutations towards the end of the sequence. There would be more unique kmers towards the end of the gene where there is more heterogeneiry across L1HS sequences.

The data in FIGS. 8A-8D are generated as follows. All unique 8, 9, 10, and 11 mer peptide sequences using the kmerTools generate function. This analysis yielded 22,358 unique L1HS peptide kmers. The netMHCpan-4.0 tool was then used to predict which of these peptides are likely to bind to at least one of the 2,427 available HLA genotypes. A total of 8,405 unique L1HS peptides were predicted to bind to at least one HLA. An additional filter was applied to remove peptides that mapped to canonical proteins. Open reading frames were translated from the RepeatMasker database which resulted in a final set of 2,316 candidate L1HS peptide epitopes (candidate cancer antigens).

Filtering for predicted MHC binders generated a preference for 9mer epitopes (FIG. 8A). There were 2,069 kmers that mapped to a single L1HS locus and 247 kmers that mapped to more than one locus. The average overlap across HLA alleles was 12% with one exemplary peptide predicted to bind to 407 different HLA alleles. Clustering HLA genotypes using the Gephi force model found that most of the HLA genotypes clustered in a central mass with a small number of HLA types having a significant differences and clustering outside of the main cluster. For example, HLA-A03*02, HLA-A03:01, and HLA-A11:01 clustered separately from the majority of the HLA genotypes due to a small amount of overlap with all other HLAs.

Hotspots within the L1HS ORFs for generating MHCI binding peptides were analyzed as shown in FIGS. 8C and 8D. The average coverage across the ORF1 and ORF2 sequences was 16 and 11 kmers, respectively. There were hotspots at the junction between the trimerization and RBD-like domain, at the junction between the RBD-like domain and the dsRBD-like domain, and across the sdRBD-like domain in ORF1 (FIG. 8C). The similarity across ORF1 sequences was fairly constant across the length of the ORF. The endonuclease domain and the region between the reverse transcriptase and DUF domains were the most highly covered. Surprisingly, we found below average coverage for the reverse transcriptase domain (FIG. 8D). The similarity across ORF2 sequences was high across the necessary endonuclease and reverse transcriptase domains, but dropped sharply towards the 3' end of the element.

B. MHC Kmers Expressed Across Developmental Stages

A strength of this approach relies on the ability to identify L1HS peptides that are almost never expressed in healthy tissue. This is a challenge to identify because access to healthy tissue is limited, but fortunately a database of healthy human tissue was recently published (N=310) [48]. The mammalian expression database is particularly useful because it includes 7 human tissue types sampled across 23 developmental timepoints.

Transposable expression is expected to be higher during embryonal human developmental stages because regions of the genome that are not usually expressed become activated to support early human development [21]. We identified 1,649 L1HS epitope kmers with a count of at least 2 reads. There were 667 L1HS epitopes that were never detected across all 311 RNA-seq samples. We found 11 L1HS epitopes with decreasing expression across developmental stages and 36 kmers with increasing expression (Kruskal test: adjusted p-value $<0.05$).

Figure 9:
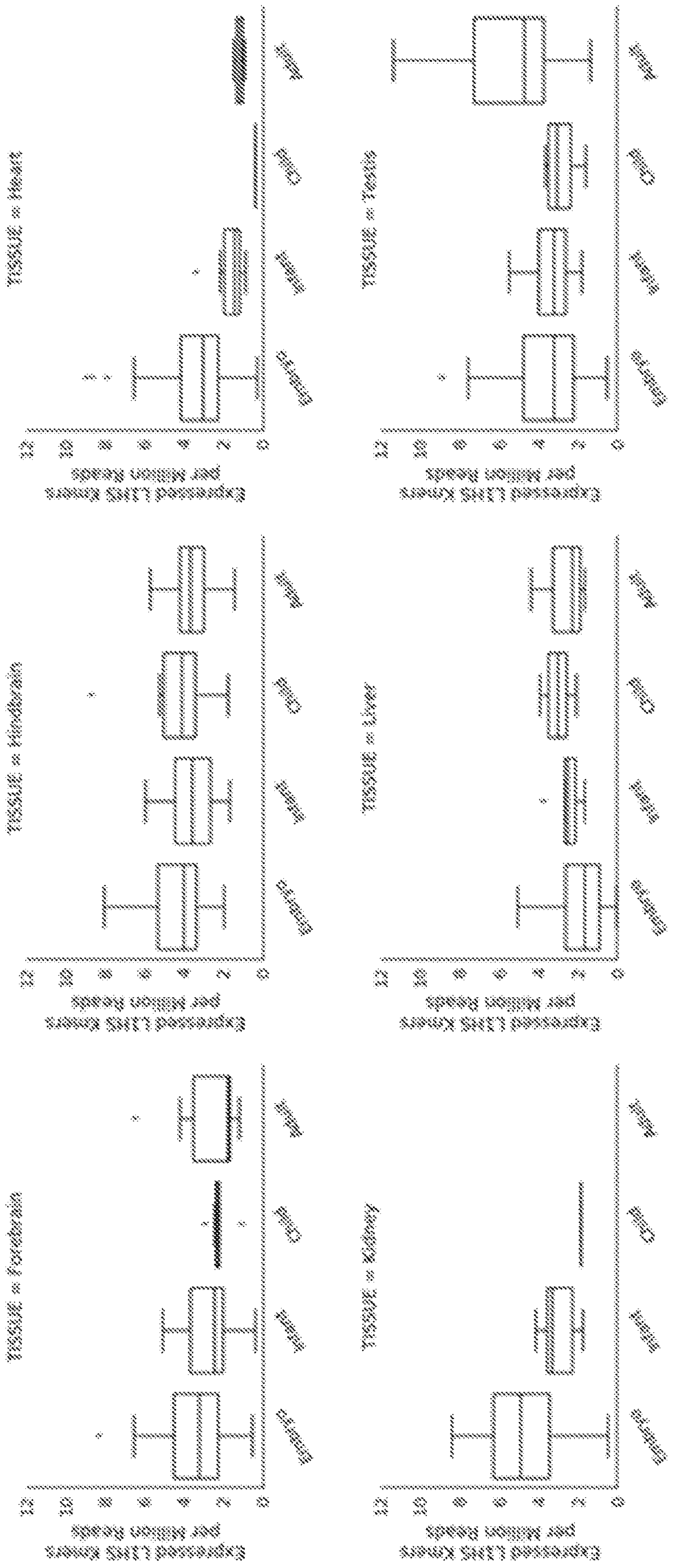
FIG. 9 shows L1HS expression varies based on tissue and developmental stage according to embodiments of the present disclosure.

FIG. 9 shows L1HS expression varies based on tissue and developmental stage according to embodiments of the present disclosure. Box plots of the number of expressed L1HS epitope kmers per million RNA-seq reads across 6 tissue type and 4 developmental stages. FIG. 9 is across all L1HS loci.

FIG. 9 shows the expression can vary across developmental stages and across tissue types. In general, we found that there was consistent expression across brain samples, which is expected because brain tissue expresses these elements at higher levels, but heart tissue decreased across developmental stages. Interestingly, there is like a slight pattern where expression for heart tissue increased from child to adult. There could be another region where there is a higher expression in L1HS elements in adults, indicating a need to be careful about L1HS elements that are expressed in normal tissues. Embodiments can normalize this expression to normal L1HS expression.

Overall, consistently low expression of L1HS epitope kmers was observed across developmental stages and tissue types. As expected, constant expression of L1HS epitope sequences in brain tissues across developmental stages [24]. Similarly, constant expression across developmental stages in germline testis tissue was observed, but as well as constant expression in liver tissue (Kruskal test: p-value >0.05). Extracranial tissue including heart and kidney had high levels of expression in the embryo, but significantly lower expression in postnatal samples (Kruskal test: p-value <0.05).

Figure 10:
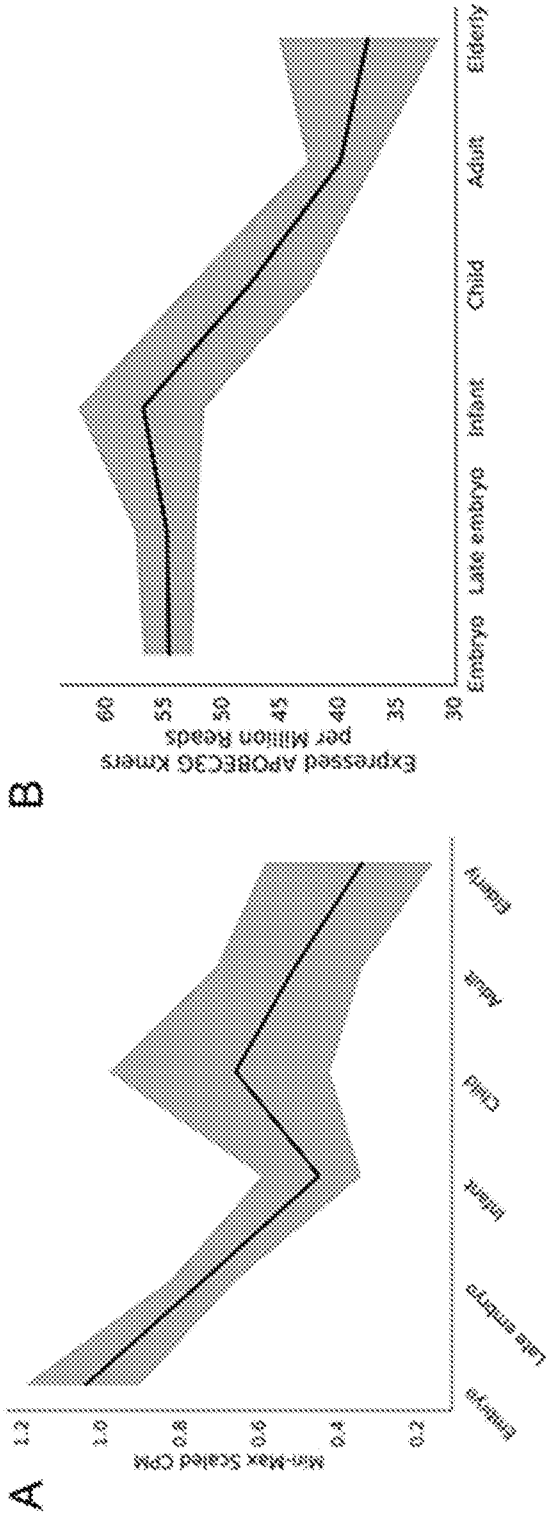
FIG. 10 shows APOBEC3C expression is highest in embryonic tissue according to embodiments of the present disclosure.

FIG. 10A shows average APOBEC3 expression across 7 tissue types and 23 developmental stages, and FIG. 10B shows average APOBEC3G kmer expression across the same cohort.

Differential expression of several APOPBEC genes was observed with the highest expression at embryonic stages. Interestingly, a spike in L1HS expression and APOBEC expression was observed in the school-age children samples. A similar expression pattern was seen in synthetically mutated APOBEC3C kmers where embryonic tissue had the highest number of mutated kmers and later stages had lower expression.

FIGS. 10A-10B show that lower APOBEC3C expression is observed across developmental stages, which is consistent with how APOBEC functions. At early ages, one has higher expression of transposable elements, where APOBEC gets turned on in order to dampen down the transposable element activity. But later in life when transposable element expression decreases, APOBEC expression also decreases.

C. L1HS Peptides are Presented on Triple Negative Breast Cancer Cells but not Matched Normal Cells Triple negative breast cancer (TNBC) is an aggressive disease that is resistant to multimodal therapy. Immunotherapy has recently been approved as a first-line treatment for TNBC, but response rates remain low and additional strategies are needed to improve durable response rates [50]. The disclosed analysis of RNA-seq identifies TE T cell epitopes that are likely to be presented on MHC, but there are additional regulatory mechanisms that may prevent some of these peptides from being efficiently processed and presented on the MHC. Recent improvements in the resolution of mass spectrometry equipment has allowed for the identification of short peptides, including MHC-bound peptides [51,52]. Isolation of MHC peptides followed by high-resolution mass spectrometry identifies potential cancer antigens for TNBC.

While it is known that TEs are overexpressed in cancer cells, there has been limited data presented to show that TE peptides are presented by cancer cell MHCs. The L1HS epitope database, Immune Epitope Database (IEDB), and a publicly available immunopeptidome dataset for a cohort of TNBC tumor and matched normal samples was used to investigate whether shared candidate cancer antigens were presented on cancer samples but not matched normal samples (Table 1). Using the MaxQuant search algorithm for mass spectrum matching, we identified three L1HS peptides presented on 5 different patient tumor samples (Table 1). Two of the peptides were shared across different TNBC samples, suggesting that public antigens are similarly processed and presented across individuals with likely different HLA genotypes. This evidence shows that L1HS peptides are identifiable in patient tumor samples using mass spectrometry analysis and further supports these molecules as viable cancer antigens for combination immunotherapy. Furthermore, no L1HS peptides were detected on matched normal tissue samples that were similarly analyzed by MHC peptidome profiling.

TABLE 1

MHC-bound L1HS peptides on triple negative breast cancer tumor samples

| Sample | Peptide | L1HS ORF | Protein Domain |
|---|---|---|---|
| Tumor 1 | KIKGWRKI (SEQ ID NO: 11) | ORF2 | Endonuclease domain |
| Tumor 2 | IKRNEQSL (SEQ ID NO: 12) | ORF1 | Trimerization domain |
| Tumor 3 | IKRNEQSL (SEQ ID NO: 12) | ORF1 | Trimerization domain |
| Tumor 4 | SFYEASIIL (SEQ ID NO: 13) | ORF2 | Reverse transcriptase domain |
| Tumor 5 | SFYEASIIL (SEQ ID NO: 13) | ORF2 | Reverse transcriptase domain |

Table 1 shows peptides that map to L1HS open reading frames that were presented on triple negative breast cancer tumors. Although the distribution of predicted binders did not show a preference to protein domain, all of the peptides for this small set of samples that were presented on the tumor cell surface mapped to a functional domain within the L1HS gene. This shows that while using the disclosed algorithmic approaches, there was no preference towards a particular protein domain.

L1HS epitope expression was then investigated using the TCGA TNBC cohort (N=190). A total of 1,428 L1HS epitope kmers were found with a count of at least 2 reads. There were 162 L1HS epitope sequences that were never detected in the healthy tissue compendium. The average number of expressed kmers per sample was 72, and the average number of expressed kmers predicted to bind to one of the patient's HLA alleles was 22. The average overlap in kmers across unrelated TNBC tumor samples with nonzero L1HS kmer expression was 6%. The number of expressed HLA-matched L1HS epitope binders was correlated with the TNBC patient's overall survival data A 58% decrease in the Cox proportional hazard ratio (95% CI: 0.19-0.97, p<0.05) was observed. Further amplification of the anti-L1HS immune response may through the use of TE peptides promote the antitumor immune response.

Figure 11:
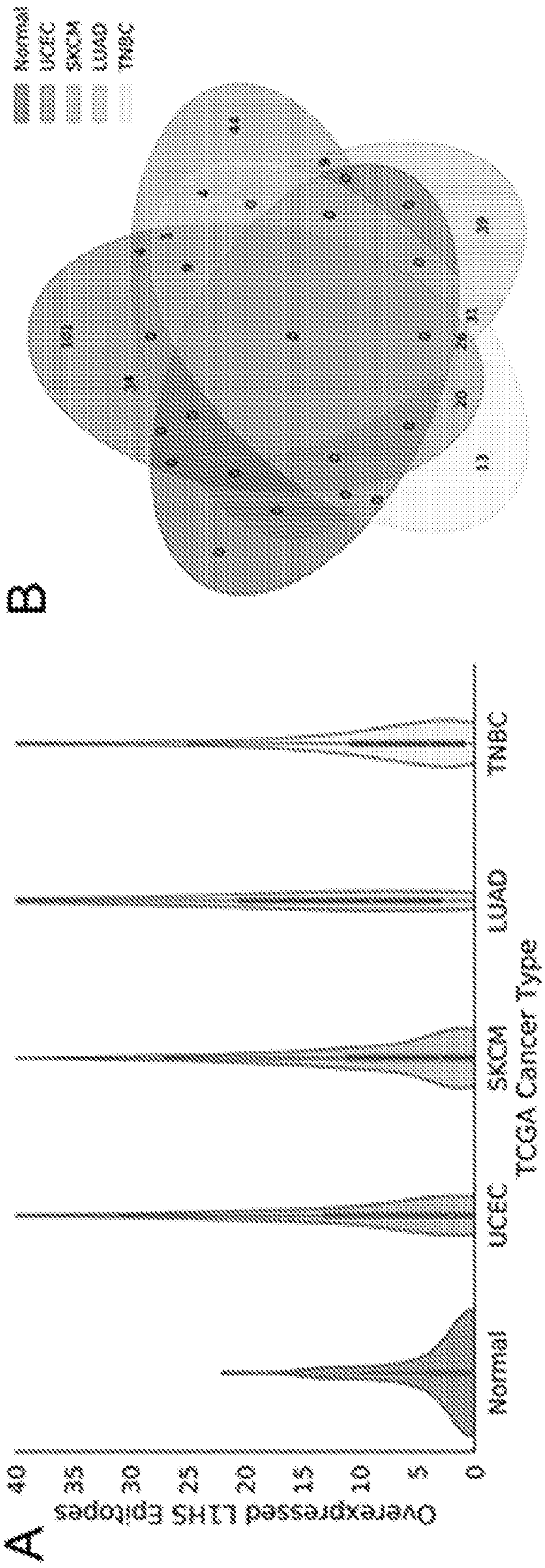
FIG. 11 shows TCGA cancers express L1HS epitope sequences that are not expressed in healthy postnatal human samples.

D. Shared L1HS Epitope Expression Occurs Across TCGA Cancer Types but not Normal Samples It was then investigated whether the expressed L1HS epitopes were specific to cancer types or whether there were shared epitopes across diseases (FIGS. 11A and 11B). L1HS epitopes were expressed higher in cancer tissue samples than the matched set of postnatal healthy control samples (FIG. 11A). We found that most of the epitopes were disease specific (FIG. 11B), which is consistent with previous studies in cell-specific expression of permissive loci [49]. There were 9 L1HS epitopes that were expressed in all four TCGA cancer types but not in the healthy control data set.

FIGS. 11A and 11B show TCGA cancers express L1HS epitope sequences that are not expressed in healthy postnatal human samples. FIG. 11A shows a violin plot of overexpressed L1HS epitope sequences in postnatal healthy samples and four TCGA cancer types. In general, there is some expression in normal but there are more outlier levels of expression in cancer. FIG. 11B shows a Venn diagram of recurrent (n>5) L1HS epitopes across cancer types and healthy controls. UCEC: uterine corpus endometrial carcinoma, SKCM: skin cutaneous melanoma, LUAD: lung adenocarcinoma, TNBC: triple negative breast cancer. As one can see, many of the epitopes differ from one type of cancer to another, but there is some overlap. For example, there are 13 cancer antigens that were identified that are only in triple negative breast cancer and there are 101 that are unique to uterine carcinoma. The overlap of all of the candidate antigens with the normal tissue is zero across all the sets.

E. L1HS Kmers that Correlate with Checkpoint Blockade Response

Some embodiments can use TE vaccine therapies in combination with checkpoint blockade therapy. To investigate the clinical efficacy of this approach, the number of predicted L1HS epitopes was correlated to the response to checkpoint blockade therapy in a set of 129 melanoma tumor samples. It was found that patients with a complete response to checkpoint blockade therapy had more predicted MHC-bound LINE-1 peptides compared to samples with progressive disease or stable disease (Mann-Whitney U-test p-value <0.05, FIGS. 11A and 11B). Patients with a partial response had the second highest abundance of L1HS epitopes. Amplifying the immune response against these epitopes may increase the response rate to checkpoint blockade therapy.

Figure 12:
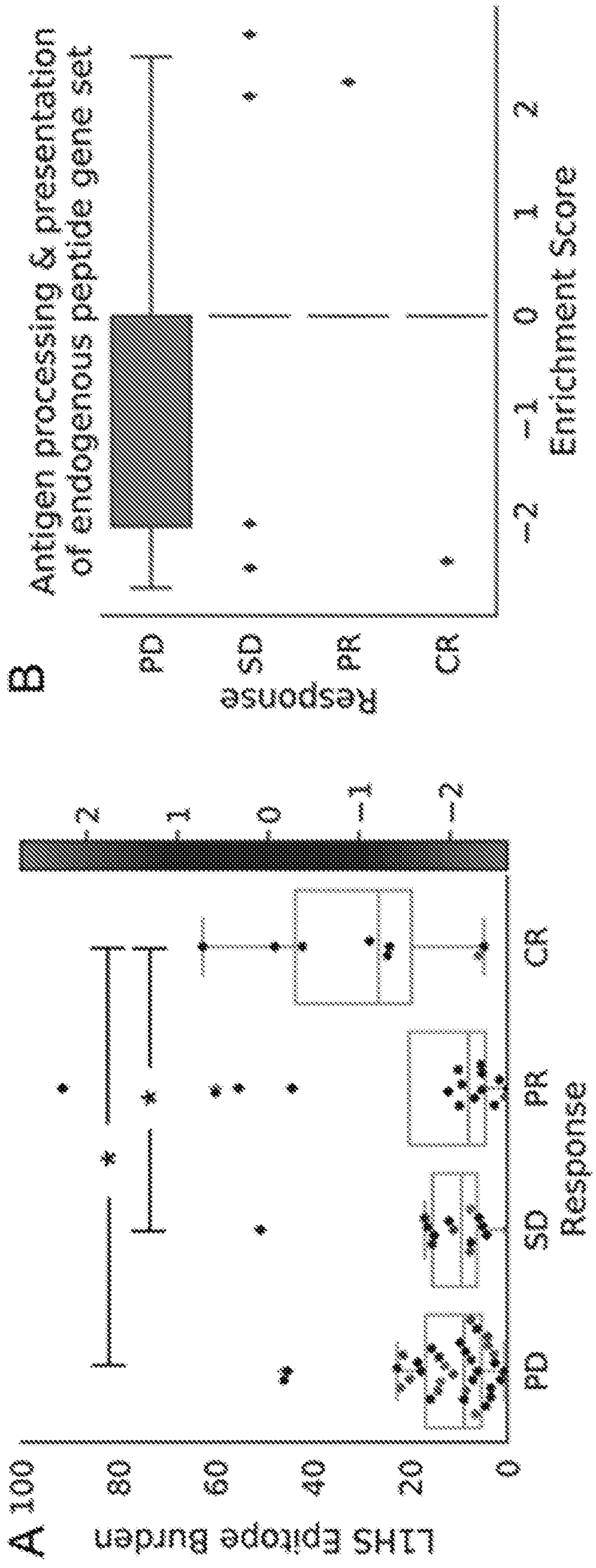
FIG. 12 shows MHC bound peptide burden correlates with complete response to checkpoint blockade therapy.

FIGS. 12A and 12B show MHC bound peptide burden correlates with complete response to checkpoint blockade therapy. FIG. 12A shows a box plot of the total L1HS epitope expression across melanoma checkpoint blockade response groups (N=73). FIG. 12B shows a gene set enrichment analysis of the Gene Ontology antigen processing and presentation of endogenous peptide gene set.

FIGS. 12A and 12B show that the number of L1 epitopes per patient correlates with complete response to checkpoint blockade therapy. This data is for a set of melanoma patients for which RNA sequencing was performed. The patients were also given checkpoint blockade therapy, where it is known if the patient responded or didn't respond. In general, we find that the patients that have a complete response to the tumor have significantly higher number of L1HS epitopes detectable in their RNA sequencing data. The other responses do not have zero L1HS, but lower. Thus, by giving a vaccine therapy, these patients could have a better response to checkpoint blockade therapy.

Progressive disease (PD) means that checkpoint blockade therapy was given and the tumor kept progressing. Stable disease (SD) means the tumor stayed the same size, and then partial response (PR) means that the tumor reduced in size but did not meet the criterion for complete response.

IX. CONCLUSION

Checkpoint blockade therapy has generated remarkable responses in a subset of cancer patients, but further research into combination therapies is needed to increase the number of patients who benefit [4,10,53]. Disclosed herein is a computational framework for prioritizing transposable element (TE) epitopes for personalized cancer vaccine therapies. It is hypothesized that combination TE vaccine immunization and checkpoint blockade therapy may tip the balance in favor of immune-mediated destruction of the tumor. A combination cancer vaccine and checkpoint blockade therapy was used recently to treat glioblastoma and this study found that these therapies work synergistically [10]. The power of the immune system to destroy cancer at a cellular level, throughout the body, and to maintain a memory against recurrence allows for this therapeutic approach to achieve durable response and potentially cure patients of their cancer.

We identified peptides that are expressed in cancer cells but not healthy cells. We applied our approach to a large cohort of 311 healthy RNA-seq datasets across 23 developmental stages and 7 tissue types. While we detected L1HS expression in these samples, we found that cancer cells express additional L1HS peptides that were never detected in the healthy control cohort. This suggests that it is possible to identify a subset of L1HS peptides that are only expressed in cancer cells, so amplification of an immune response against these peptides may not generate off-target effects that may be toxic to the patient.

Much of the data on TE expression in the literature is based on RNA-seq data, but whether these elements generate peptides that are presented on human cancer cell MHCs has not been sufficiently investigated. Disclosed herein is evidence that L1HS peptides are indeed presented by cancer cells in triple negative breast cancer tumors but not matched normal tissue samples. This shows that not only are these elements aberrantly expressed in cancer cells, but these TE transcripts are translated into proteins and these proteins are properly processed and presented by MHC molecules. Moreover, we found that expression of predicted MHC bound TE peptides lead to a 58% reduction in the Cox proportional hazards ratio for the TCGA TNBC cohort. Thus, people having cancers with these overexpressed peptides generally do better, as they have less risk than patients that have low express. This underscores the benefit of these molecules for treating cancer, since the expression of these molecules correlates with better patient outcomes, presumably since these molecules may induce immune responses that limit tumor growth.

Lastly, L1HS epitope expression was correlated with response to checkpoint blockade therapy in melanoma [54, 55]. Surprisingly, the expression of L1HS epitopes correlated with the complete response group of melanoma patients. Introduction of checkpoint blockade therapy may have augmented the immune response. Notably, the expression of these peptides was low, but detectable in non-responders or partial responders.

These results provide hope that further expansion of T-cells that are able to recognize cancer cells through identification of tumor-specific TE expression analysis may increase the number of patients that experience durable responses. One of the many strengths of this approach is that these peptides are shared across individuals. We propose a novel therapeutic paradigm for matching tumors to a repository of validated cancer vaccines for efficient distribution and administration of therapy. This includes the screening of large cancer RNA-seq data sets for the most commonly overexpressed epitopes, prioritizing epitopes that correlate with patient benefit. We then propose synthesizing, quality control, and validation of these peptides before mass production and distribution to treat cancer at scale.

Transposable elements make up ~40% of the human genome, encode viral like proteins, and are strongly repressed in somatic cells. This makes them attractive targets for cancer vaccine development, but the sequence similarity and complexity of the genome makes it difficult to identify which peptides to prioritize. Disclosed herein is an exciting new computational framework based on unique expression of MHC bound peptide kmers. This approach was able to identify expression of L1HS epitopes that correlated with better survival outcomes and complete response to checkpoint blockade therapy.

X. EXAMPLE SYSTEMS

Figure 14:
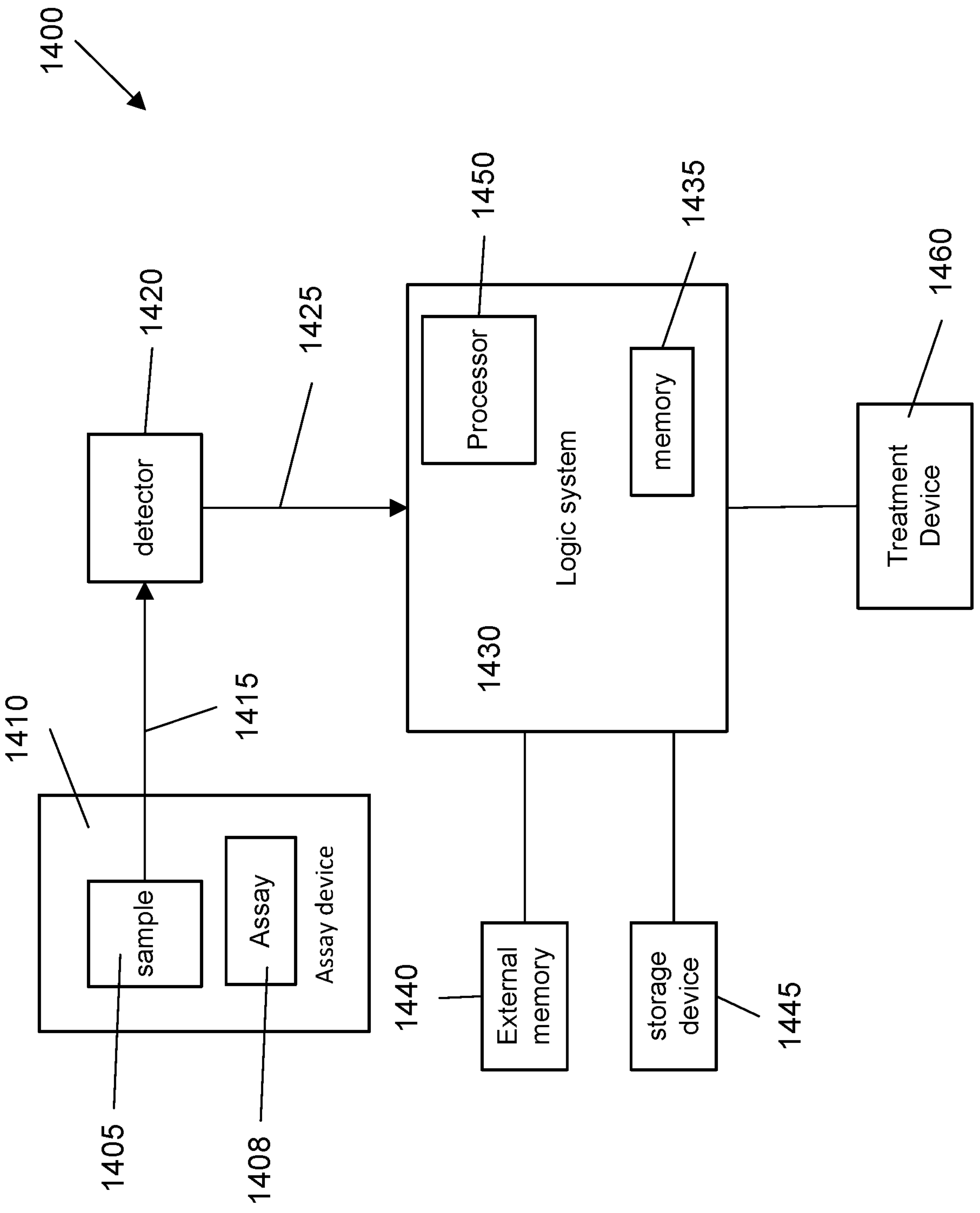
FIG. 14 illustrates a measurement system according to an embodiment of the present disclosure.

FIG. 14 illustrates a measurement system 1400 according to an embodiment of the present disclosure. The system as shown includes a sample 1405, such as cell-free DNA molecules within an assay device 1410, where an assay 1408 can be performed on sample 1405. For example, sample 1405 can be contacted with reagents of assay 1408 to provide a signal of a physical characteristic 1415. An example of an assay device can be a flow cell that includes probes and/or primers of an assay or a tube through which a droplet moves (with the droplet including the assay). Physical characteristic 1415 (e.g., a fluorescence intensity, a voltage, or a current), from the sample is detected by detector 1420. Detector 1420 can take a measurement at intervals (e.g., periodic intervals) to obtain data points that make up a data signal. In one embodiment, an analog-to-digital converter converts an analog signal from the detector into digital form at a plurality of times. Assay device 1410 and detector 1420 can form an assay system, e.g., a sequencing system that performs sequencing according to embodiments described herein. A data signal 1425 is sent from detector 1420 to logic system 1430. As an example, data signal 1425 can be used to determine sequences and/or locations in a reference genome of DNA molecules. Data signal 1425 can include various measurements made at a same time, e.g., different colors of fluorescent dyes or different electrical signals for different molecule of sample 1405, and thus data signal 1425 can correspond to multiple signals. Data signal 1425 may be stored in a local memory 1435, an external memory 1440, or a storage device 1445.

Logic system 1430 may be, or may include, a computer system, ASIC, microprocessor, etc. It may also include or be coupled with a display (e.g., monitor, LED display, etc.) and a user input device (e.g., mouse, keyboard, buttons, etc.). Logic system 1430 and the other components may be part of a stand-alone or network connected computer system, or they may be directly attached to or incorporated in a device (e.g., a sequencing device) that includes detector 1420 and/or assay device 1410. Logic system 1430 may also include software that executes in a processor 1450. Logic system 1430 may include a computer readable medium storing instructions for controlling measurement system 1400 to perform any of the methods described herein. For example, logic system 1430 can provide commands to a system that includes assay device 1410 such that sequencing or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

System 1400 may also include a treatment device 1460, which can provide a treatment to the subject. Treatment device 1460 can determine a treatment and/or be used to perform a treatment. Examples of such treatment can include surgery, radiation therapy, chemotherapy, immunotherapy, targeted therapy, hormone therapy, and stem cell transplant. Logic system 1430 may be connected to treatment device 1460, e.g., to provide results of a method described herein. The treatment device may receive inputs from other devices, such as an imaging device and user inputs (e.g., to control the treatment, such as controls over a robotic system).

Figure 15:
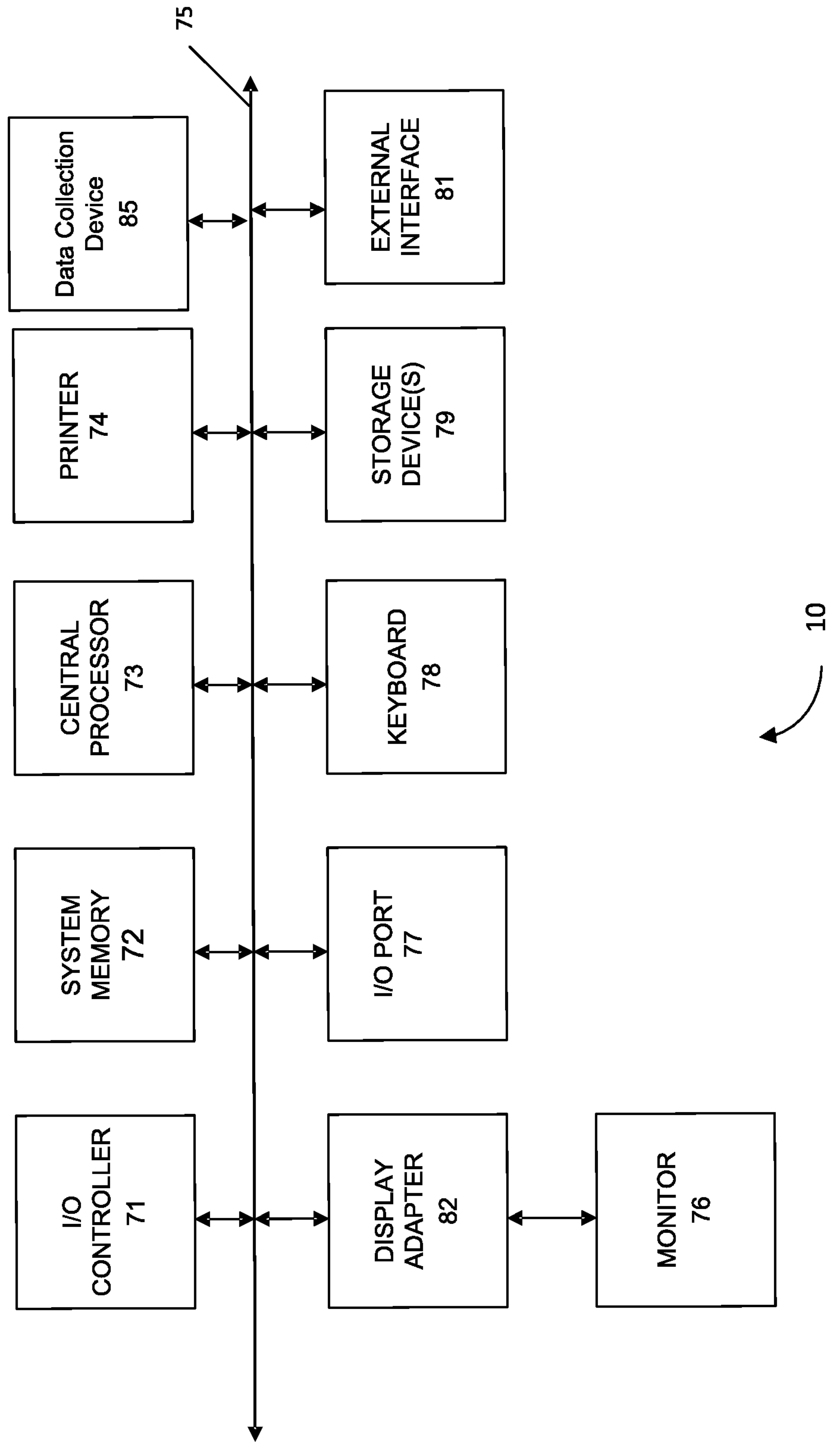
FIG. 15 shows a block diagram of an example computer system usable with systems and methods according to embodiments of the present disclosure.

Any of the computer systems mentioned herein may utilize any suitable number of subsystems. Examples of such subsystems are shown in FIG. 15 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 15 are interconnected via a system bus 75. Additional subsystems such as a printer 74, keyboard 78, storage device(s) 79, monitor 76 (e.g., a display screen, such as an LED), which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk) or Blu-ray disk, flash memory, and the like. The computer readable medium may be any combination of such storage or transmission devices. In addition, the order of operations may be re-arranged. A process can be terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the disclosure. However, other embodiments of the disclosure may be directed to specific embodiments relating to each individual aspect, or specific combinations of these individual aspects.

The above description of example embodiments of the present disclosure has been presented for the purposes of illustration and description. It is not intended to be exhaustive or to limit the disclosure to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

XI. REFERENCES

All patents, patent applications, publications, and descriptions mentioned herein are incorporated by reference in their entirety for all purposes. None is admitted to be prior art.

1. Murphy S L. Mortality in the United States, 2017. 2018; 8.
2. Wilking N, Karolinska Institutet, Solna, Sweden, Lopes G, Sylvester Comprehensive Cancer Center, University of Miami, FL, US, Meier K, HKK Soltau, Lower Saxony & Heidekreis-Klinikum GmbH, Soltau, Germany, et al. Can we Continue to Afford Access to Cancer Treatment? Eur Oncol Haematol. 2017; 13: 114. doi:10.17925/EOH.2017.13.02.114
3. CD28 and CTLA-4 have opposing effects on the response of T cells to stimulation. J Exp Med. 1995; 182: 459-465.
4. Zappasodi R, Merghoub T, Wolchok J D. Emerging Concepts for Immune Checkpoint Blockade-Based Combination Therapies. Cancer Cell. 2018; 33: 581-598. doi:10.1016/j.ccell.2018.03.005
5. Ribas A, Wolchok J D. Cancer immunotherapy using checkpoint blockade. Science. 2018; 359: 1350-1355. doi:10.1126/science.aar4060
6. Pitt J M, Vétizou M, Daillère R, Roberti M P, Yamazaki T, Routy B, et al. Resistance Mechanisms to Immune-Checkpoint Blockade in Cancer: Tumor-Intrinsic and -Extrinsic Factors. 2016; 44. doi:10.1016/j.immuni.2016.06.001
7. Simon S, Labarriere N. PD-1 expression on tumor-specific T cells: Friend or foe for immunotherapy? Oncoimmunology. 2017; 7. doi:10.1080/2162402X.2017.1364828
8. Seidel J A, Otsuka A, Kabashima K. Anti-PD-1 and Anti-CTLA-4 Therapies in Cancer: Mechanisms of Action, Efficacy, and Limitations. Front Oncol. 2018; 8. doi:10.3389/fonc.2018.00086
9. Khair D O, Bax H J, Mele S, Crescioli S, Pellizzari G, Khiabany A, et al. Combining Immune Checkpoint Inhibitors: Established and Emerging Targets and Strategies to Improve Outcomes in Melanoma. Front Immunol. 2019; 10. doi:10.3389/fimmu.2019.00453
10. Liu C, Schaettler M, Bowman-Kirigin J, Kobayashi D, Miller C, Johanns T, et al. IMMU-09. COMBINA- TION IMMUNE TREATMENT OF A HIGHLY AGGRESSIVE ORTHOTOPIC MURINE GLIOBLASTOMA WITH CHECKPOINT BLOCKADE AND MULTI-VALENT NEOANTIGEN VACCINATION. Neuro-Oncol. 2019; 21: vi120-vi121. doi:10.1093/neuonc/noz175.503
11. Lee K L, Benz S C, Hicks K C, Nguyen A, Gameiro S R, Palena C, et al. Efficient Tumor Clearance and Diversified Immunity through Neoepitope Vaccines and Combinatorial Immunotherapy. Cancer Immunol Res. 2019; 7: 1359-1370. doi:10.1158/2326-6066.CIR-18-0620
12. Burg S H van der, Arens R, Ossendorp F, Hall T van, Melief C J M. Vaccines for established cancer: overcoming the challenges posed by immune evasion. Nat Rev Cancer. 2016; 16: 219-233. doi:10.1038/nrc.2016.16
13. Banchereau J, Palucka K. Cancer vaccines on the move. Nat Rev Clin Oncol. 2018; 15: 9-10. doi:10.1038/nrclinonc.2017.149
14. Laumont C M, Vincent K, Hesnard L, Audemard É, Bonneil É, Laverdure J-P, et al. Noncoding regions are the main source of targetable tumor-specific antigens. Sci Transl Med. 2018; 10. doi:10.1126/scitranslmed.aau5516
15. Kong Y, Rose C M, Cass A A, Williams A G, Darwish M, Lianoglou S, et al. Transposable element expression in tumors is associated with immune infiltration and increased antigenicity. Nat Commun. 2019; 10: 1-14. doi:10.1038/s41467-019-13035-2
16. Bourque G, Burns K H, Gehring M, Gorbunova V, Seluanov A, Hammell M, et al. Ten things you should know about transposable elements. Genome Biol. 2018; 19: 199. doi:10.1186/s13059-018-1577-z
17. Finnegan D J. Transposable elements: How non-LTR retrotransposons do it. Curr Biol. 1997; 7: R245-R248. doi:10.1016/50960-9822(06)00112-6
18. Kassiotis G, Stoye J P. Immune responses to endogenous retroelements: taking the bad with the good. Nat Rev Immunol. 2016; 16: 207-219. doi:10.1038/nri.2016.27
19. Burns K H. Our Conflict with Transposable Elements and Its Implications for Human Disease. Annu Rev Pathol Mech Dis. 2020; 15: 51-70. doi:10.1146/annurev-pathmechdis-012419-032633
20. De Cecco M, Criscione S W, Peterson A L, Neretti N, Sedivy J M, Kreiling J A. Transposable elements become active and mobile in the genomes of aging mammalian somatic tissues. Aging. 2013; 5: 867-883.
21. Gerdes P, Richardson S R, Mager D L, Faulkner G J. Transposable elements in the mammalian embryo: pioneers surviving through stealth and service. Genome Biol. 2016; 17: 100. doi:10.1186/s13059-016-0965-5
22. Chung N, Jonaid G M, Quinton S, Ross A, Sexton C E, Alberto A, et al. Transcriptome analyses of tumor-adjacent somatic tissues reveal genes co-expressed with transposable elements. Mob DNA. 2019; 10: 39. doi:10.1186/s13100-019-0180-5
23. Saleh A, Macia A, Muotri A R. Transposable Elements, Inflammation, and Neurological Disease. Front Neurol. 2019; 10. doi:10.3389/fneur.2019.00894
24. Terry D M, Devine S E. Aberrantly High Levels of Somatic LINE-1 Expression and Retrotransposition in Human Neurological Disorders. Front Genet. 2020; 10. doi:10.3389/fgene.2019.01244
25. Sacha J B, Kim I-J, Chen L, Ullah J H, Goodwin D A, Simmons H A, et al. Vaccination with Cancer- and HIV Infection-Associated Endogenous Retrotransposable Elements Is Safe and Immunogenic. J Immunol. 2012; 189: 1467-1479. doi:10.4049/jimmunol.1200079
26. Sheppard N C, Jones R B, Burwitz B J, Nimityongskul F A, Newman L P, Buechler M B, et al. Vaccination against Endogenous Retrotransposable Element Consensus Sequences Does Not Protect Rhesus Macaques from SIVsmE660 Infection and Replication. PLOS ONE. 2014; 9: e92012. doi:10.1371/journal.pone.0092012
27. Jeong H-H, Yalamanchili H K, Guo C, Shulman J M, Liu Z. An ultra-fast and scalable quantification pipeline for transposable elements from next generation sequencing data. Pac Symp Biocomput Pac Symp Biocomput. 2018; 23: 168-179.
28. Swanton C, McGranahan N, Starrett G J, Harris R S. APOBEC Enzymes: Mutagenic Fuel for Cancer Evolution and Heterogeneity. Cancer Discov. 2015; 5: 704-712. doi:10.1158/2159-8290.CD-15-0344
29. Sharma S, Baysal B E. Stem-loop structure preference for site-specific RNA editing by APOBEC3A and APOBEC3G. Peed. 2017; 5: e4136. doi:10.7717/peerj.4136
30. Sharma S, Patnaik S K, Taggart R T, Baysal B E. The double-domain cytidine deaminase APOBEC3G is a cellular site-specific RNA editing enzyme. Sci Rep. 2016; 6: 1-12. doi:10.1038/srep39100
31. Refsland E W, Harris R S. The APOBEC3 Family of Retroelement Restriction Factors. In: Cullen B R, editor. Intrinsic Immunity. Berlin, Heidelberg: Springer Berlin Heidelberg; 2013. pp. 1-27. doi:10.1007/978-3-642-37765-5_1
32. Roberts S A, Lawrence M S, Klimczak L J, Grimm S A, Fargo D, Stojanov P, et al. An APOBEC cytidine deaminase mutagenesis pattern is widespread in human cancers. Nat Genet. 2013; 45: 970.
33. Jurtz V, Paul S, Andreatta M, Marcatili P, Peters B, Nielsen M. NetMHCpan-4.0: Improved Peptide-WIC Class I Interaction Predictions Integrating Eluted Ligand and Peptide Binding Affinity Data. J Immunol. 2017; 199: 3360-3368. doi:10.4049/jimmunol.1700893
34. O'Donnell T J, Rubinsteyn A, Bonsack M, Riemer A B, Laserson U, Hammerbacher J. MHCflurry: Open-Source Class I WIC Binding Affinity Prediction. Cell Syst. 2018; 7: 129-132.e4. doi:10.1016/j.cels.2018.05.014
35. Goldman M, Craft B, Kamath A, Brooks A, Zhu J, Haussler D. The UCSC Xena Platform for cancer genomics data visualization and interpretation. bioRxiv. 2018; 326470. doi:10.1101/326470
36. Sharma S, Patnaik S K, Taggart R T, Kannisto E D, Enriquez S M, Gollnick P, et al. APOBEC3A cytidine deaminase induces RNA editing in monocytes and macrophages. Nat Commun. 2015; 6: 1-15. doi:10.1038/ncomms7881
37. Penzkofer T, Jäger M, Figlerowicz M, Badge R, Mundlos S, Robinson P N, et al. L1Base 2: more retrotransposition-active LINE-1s, more mammalian genomes. Nucleic Acids Res. 2017; 45: D68-D73. doi:10.1093/nar/gkw925
38. El-Gebali S, Mistry J, Bateman A, Eddy S R, Luciani A, Potter S C, et al. The Pfam protein families database in 2019. Nucleic Acids Res. 2019; 47: D427-D432. doi:10.1093/nar/gky995
39. Boichard A, Pham T V, Yeerna H, Goodman A, Tamayo P, Lippman S, et al. APOBEC-related mutagenesis and neo-peptide hydrophobicity: implications for response to immunotherapy. Oncoimmunology. 2018; 8. doi:10.1080/2162402X.2018.1550341
40. Wang S, Jia M, He Z, Liu X-S. APOBEC3B and APOBEC mutational signature as potential predictive markers for immunotherapy response in non-small cell lung cancer. Oncogene. 2018; 37: 3924-3936. doi: 10.1038/s41388-018-0245-9
41. Burgess D J. Switching APOBEC mutation signatures. Nat Rev Genet. 2019; 20: 253-253. doi:10.1038/s41576-019-0116-4
42. Harrow J, Frankish A, Gonzalez J M, Tapanari E, Diekhans M, Kokocinski F, et al. GENCODE: the reference human genome annotation for The ENCODE Project. Genome Res. 2012; 22: 1760-1774.
43. Kitts A, Sherry S. The single nucleotide polymorphism database (dbSNP) of nucleotide sequence variation. NCBI Handb McEntyre J Ostell J Eds Bethesda MD US Natl Cent Biotechnol Inf. 2002.
44. Vita R, Overton J A, Greenbaum J A, Ponomarenko J, Clark J D, Cantrell J R, et al. The immune epitope database (IEDB) 3.0. Nucleic Acids Res. 2015; 43: D405-D412.
45. Cox J, Mann M. MaxQuant enables high peptide identification rates, individualized ppb-range mass accuracies and proteome-wide protein quantification. Nat Biotechnol. 2008; 26: 1367-1372.
46. Cox J, Neuhauser N, Michalski A, Scheltema R A, Olsen J V, Mann M. Andromeda: A Peptide Search Engine Integrated into the MaxQuant Environment. J Proteome Res. 2011; 10: 1794-1805. doi:10.1021/pr101065j
47. Bastian M, Heymann S, Jacomy M. Gephi: an open source software for exploring and manipulating networks. Third international AAAI conference on weblogs and social media. 2009.
48. Cardoso-Moreira M, Halbert J, Valloton D, Velten B, Chen C, Shao Y, et al. Gene expression across mammalian organ development. Nature. 2019; 571: 505-509. doi:10.1038/s41586-019-1338-5
49. Philippe C, Vargas-Landin D B, Doucet A J, van Essen D, Vera-Otarola J, Kuciak M, et al. Activation of individual L1 retrotransposon instances is restricted to cell-type dependent permissive loci. Burns K, editor. eLife. 2016; 5: e13926. doi:10.7554/eLife.13926
50. Marra A, Viale G, Curigliano G. Recent advances in triple negative breast cancer: the immunotherapy era. BMC Med. 2019; 17: 90. doi:10.1186/s12916-019-1326-5
51. Bassani-Sternberg M. Mass Spectrometry Based Immunopeptidomics for the Discovery of Cancer Neoantigens. Methods Mol Biol Clifton N J. 2018; 1719: 209-221. doi:10.1007/978-1-4939-7537-2_14
52. Purcell A W, Ramarathinam S H, Ternette N. Mass spectrometry-based identification of MHC-bound peptides for immunopeptidomics. Nat Protoc. 2019; 14: 1687-1707. doi:10.1038/541596-019-0133-y
53. Minn A J, Wherry E J. Combination Cancer Therapies with Immune Checkpoint Blockade: Convergence on Interferon Signaling. Cell. 2016; 165: 272-275. doi: 10.1016/j.cell.2016.03.031
54. Hugo W, Zaretsky J M, Sun L, Song C, Moreno B H, Hu-Lieskovan S, et al. Genomic and Transcriptomic Features of Response to Anti-PD-1 Therapy in Metastatic Melanoma. Cell. 2016; 165: 35-44. doi:10.1016/j.cell.2016.02.065
55. Riaz N, Havel J J, Makarov V, Desrichard A, Urba W J, Sims J S, et al. Tumor and Microenvironment Evolution during Immunotherapy with Nivolumab. Cell. 2017; 171: 934-949.e16. doi:10.1016/j.cell.2017.09.028

TABLE 2

Example L1HS probes

| | | |
|---|---|---|
| (SEQ ID NO: 1) | TACGTTAGACCTAAAACCATAAAAACCCTAG | L1HS\|chr10\|33510845\|33516877\|-\|11\|825 |
| (SEQ ID NO: 2) | AATTCAAGATGGATTAAAGATTTATACGTTA | L1HS\|chr10\|33510845\|33516877\|-\|13\|689 |
| (SEQ ID NO: 3) | AAAGATTTATACGTTAGACCTAAAACCATAA | L1HS\|chr10\|33510845\|33516877\|-\|15\|429 |
| (SEQ ID NO: 4) | TCAAGATGGATTAAAGATTTATACGTTAGAC | L1HS\|chr10\|33510845\|33516877\|-\|16\|391 |
| (SEQ ID NO: 5) | CAAGATGGATTAAAGATTTATACGTTAGACC | L1HS\|chr10\|33510845\|33516877\|-\|17\|367 |
| (SEQ ID NO: 14) | GATTTATACGTTAGACCTAAAACCATAAAAA | L1HS\|chr10\|33510845\|33516877\|-\|17\|371 |
| (SEQ ID NO: 15) | AAGATTTATACGTTAGACCTAAAACCATAAA | L1HS\|chr10\|33510845\|33516877\|-\|18\|353 |
| (SEQ ID NO: 16) | ATTCAAGATGGATTAAAGATTTATACGTTAG | L1HS\|chr10\|33510845\|33516877\|-\|19\|257 |
| (SEQ ID NO: 17) | ATCAATTCAAGATGGATTAAAGATTTATACG | L1HS\|chr10\|33510845\|33516877\|-\|20\|205 |
| (SEQ ID NO: 18) | TCAATTCAAGATGGATTAAAGATTTATACGT | L1HS\|chr10\|33510845\|33516877\|-\|9\|959 |
| (SEQ ID NO: 19) | TATACGTTAGACCTAAAACCATAAAAACCCT | L1HS\|chr10\|33510845\|33516877\|-\|9\|967 |
| (SEQ ID NO: 20) | TATACAAAAATCAATTCAAGATGGCTTAAAG | L1HS\|chr10\|76586841\|76591753\|+\|20\|122 |
| (SEQ ID NO: 21) | TAGGCGTGGGCAAGGACTTCACGTCCAAAAC | L1HS\|chr10\|76586841\|76591753\|+\|20\|155 |
| (SEQ ID NO: 22) | CTTATACAAAAATCAATTCAAGATGGCTTAA | L1HS\|chr10\|76586841\|76591753\|+\|8\|857 |
| (SEQ ID NO: 23) | GCCCTAAAAGAGCTCCTGAAGGAAGCGGTAA | L1HS\|chr11\|78677772\|78683803\|-\|4\|191 |
| (SEQ ID NO: 24) | AGCTCCTGAAGGAAGCGGTAAACATGGAAAG | L1HS\|chr11\|78677772\|78683803\|-\|4\|195 |
| (SEQ ID NO: 25) | AAGCGGTAAACATGGAAAGGAACAACCGGTA | L1HS\|chr11\|78677772\|78683803\|-\|4\|199 |

TABLE 2-continued

| Example L1HS probes | | |
|---|---|---|
| (SEQ ID NO: 26) | GCGGTAAACATGGAAAGGAACAACCGGTACC | L1HS\|chr11\|78677772\|78683803\|-\|4\|199 |
| (SEQ ID NO: 27) | CTAAAAGAGCTCCTGAAGGAAGCGGTAAACA | L1HS\|chr11\|78677772\|78683803\|-\|6\|186 |
| (SEQ ID NO: 28) | GAAGCGGTAAACATGGAAAGGAACAACCGGT | L1HS\|chr11\|78677772\|78683803\|-\|7\|93 |
| (SEQ ID NO: 29) | GACAAGAATGCCCTCTCTCACCGCTCCTATT | L1HS\|chr11\|85324758\|85330822\|+\|11\|387 |
| (SEQ ID NO: 30) | AGACAAGAATGCCCTCTCTCACCGCTCCTAT | L1HS\|chr11\|85324758\|85330822\|+\|13\|123 |
| (SEQ ID NO: 31) | TCAACTACATGGAAACTGATCAACCTGCTCC | L1HS\|chr11\|90400067\|90406099\|-\|10\|148 |
| (SEQ ID NO: 32) | GCTCAACTACATGGAAACTGATCAACCTGCT | L1HS\|chr11\|90400067\|90406099\|-\|10\|148 |
| (SEQ ID NO: 33) | AACTGATCAACCTGCTCCTGAATGACTACTG | L1HS\|chr11\|90400067\|90406099\|-\|10\|153 |
| (SEQ ID NO: 34) | TGATCAACCTGCTCCTGAATGACTACTGGGT | L1HS\|chr11\|90400067\|90406099\|-\|10\|154 |
| (SEQ ID NO: 35) | AAACTGATCAACCTGCTCCTGAATGACTACT | L1HS\|chr11\|90400067\|90406099\|-\|11\|108 |
| (SEQ ID NO: 36) | ATGAGTGAATTCCCATTCACAATTGTTTCAA | L1HS\|chr11\|90400067\|90406099\|-\|16\|184 |
| (SEQ ID NO: 37) | CACAGACTGGCAAGTTGGATAAAGACTCAAG | L1HS\|chr11\|90400067\|90406099\|-\|9\|24 |
| (SEQ ID NO: 38) | GACACAGACTGGCAAGTTGGATAAAGACTCA | L1HS\|chr11\|90400067\|90406099\|-\|9\|24 |
| (SEQ ID NO: 39) | ACAGACTGGCAAGTTGGATAAAGACTCAAGA | L1HS\|chr11\|90400067\|90406099\|-\|9\|25 |
| (SEQ ID NO: 40) | AGCTCCTGAAGGAAGCGCTAAACATGGAAAG | L1HS\|chr15\|51417216\|51423247\|-\|2\|195 |
| (SEQ ID NO: 41) | AGGAAATAAAAGAGGACACAAACAATTGGAA | L1HS\|chr18\|54426981\|54430582\|+\|5\|221 |
| (SEQ ID NO: 42) | AGAGAAATGCAAATCAAAACCACTATGAGAT | L1HS\|chr1\|104770247\|104776279\|-\|24\|100 |
| (SEQ ID NO: 43) | TCAGAGAAATGCAAATCAAAACCACTATGAG | L1HS\|chr1\|104770247\|104776279\|-\|24\|100 |
| (SEQ ID NO: 44) | ATCAGAGAAATGCAAATCAAAACCACTATGA | L1HS\|chr1\|104770247\|104776279\|-\|24\|100 |
| (SEQ ID NO: 45) | GAAATGCAAATCAAAACCACTATGAGATATC | L1HS\|chr1\|104770247\|104776279\|-\|24\|101 |
| (SEQ ID NO: 46) | GAGAAATGCAAATCAAAACCACTATGAGATA | L1HS\|chr1\|104770247\|104776279\|-\|24\|101 |
| (SEQ ID NO: 47) | CTCACACCAGTTAGAATGGCAATCATTAAAA | L1HS\|chr1\|104770247\|104776279\|-\|24\|112 |
| (SEQ ID NO: 48) | TCACACCAGTTAGAATGGCAATCATTAAAAA | L1HS\|chr1\|104770247\|104776279\|-\|24\|113 |
| (SEQ ID NO: 49) | ACACCAGTTAGAATGGCAATCATTAAAAAGT | L1HS\|chr1\|104770247\|104776279\|-\|24\|113 |
| (SEQ ID NO: 50) | AAGCGCTAAACATGGAAAGGAACAACCGGTA | L1HS\|chr1\|197707714\|197713747\|+\|4\|199 |
| (SEQ ID NO: 51) | GAATCACTAAACATGGAAAGGAACAACCGGT | L1HS\|chr1\|247687173\|247693205\|+\|5\|198 |
| (SEQ ID NO: 52) | TCCACACGTATGTTTATTGCAGCACTATTCA | L1HS\|chr22\|48985761 \|48991793\|-\|12\|927 |
| (SEQ ID NO: 53) | CATCCACACGTATGTTTATTGCAGCACTATT | L1HS\|chr22\|48985761 \|48991793\|-\|26\|117 |
| (SEQ ID NO: 54) | GAGCTGATGGAGCTGAAAACCAAGACTCGAG | L1HS\|chr22\|48985761\|48991793\|-\|2\|54 |
| (SEQ ID NO: 55) | AGCTGATGGAGCTGAAAACCAAGACTCGAGA | L1HS\|chr22\|48985761\|48991793\|-\|2\|55 |
| (SEQ ID NO: 56) | ATGGAGCTGAAAACCAAGACTCGAGAACTAC | L1HS\|chr22\|48985761\|48991793\|-\|3\|0 |
| (SEQ ID NO: 57) | GAGCTGAAAACCAAGACTCGAGAACTACGTG | L1HS\|chr22\|48985761\|48991793\|-\|3\|2 |
| (SEQ ID NO: 58) | TGAAAACCAAGACTCGAGAACTACGTGAAGA | L1HS\|chr22\|48985761\|48991793\|-\|3\|3 |
| (SEQ ID NO: 59) | CTGAAAACCAAGACTCGAGAACTACGTGAAG | L1HS\|chr22\|48985761\|48991793\|-\|3\|3 |
| (SEQ ID NO: 60) | TTCCCCAATCTAGCAAGGCAGACCAACGTTC | L1HS\|chr2\|102566355\|102572386\|-\|4\|65 |
| (SEQ ID NO: 61) | GGCAGACCAACGTTCAGATTCAGGAAATACA | L1HS\|chr2\|102566355\|102572386\|-\|5\|67 |
| (SEQ ID NO: 62) | GCGCTAAACATGGAAAGGAACAACCGGTACC | L1HS\|chr2\|112503812\|112509846\|-\|4\|199 |
| (SEQ ID NO: 63) | AAGATTTAAACGTTAAACCTAAAACCATAAA | L1HS\|chr2\|196905587\|196911637\|+\|18\|363 |
| (SEQ ID NO: 64) | TTGTCCCTGTTTGCAGACGACATGATTGTTT | L1HS\|chr2\|196905587\|196911637\|+\|18\|94 |

TABLE 2-continued

| Example L1HS probes | | |
|---|---|---|
| (SEQ ID NO: 65) | GTCTATGTGAAAAGACCAAATCTACGTCTGA | L1HS\|chr2\|196905587\|196911637\|+\|4\|30 |
| (SEQ ID NO: 66) | CAACAAGAGGAGCTAACTATCCTAAATATGT | L1HS\|chr2\|86655238\|86661269\|-\|10\|104 |
| (SEQ ID NO: 67) | GAAGCGCTAAACATGGAAAGGAACAACCGGT | L1HS\|chr3\|158019676\|158025705\|+\|4\|198 |
| (SEQ ID NO: 68) | ATAGGCGTGGGCAAGGACTTCACGTCCAAAA | L1HS\|chr3\|159095379\|159101395\|-\|23\|154 |
| (SEQ ID NO: 69) | GTCGGGTTACCCTCAAAGGAAAGCCCATCAG | L1HS\|chr3\|54394322\|54400324\|-\|2\|118 |
| (SEQ ID NO: 70) | CGGGTTACCCTCAAAGGAAAGCCCATCAGAC | L1HS\|chr4\|189137085\|189143105\|+\|4\|118 |
| (SEQ ID NO: 71) | CTCCTGAAGGAAGCGCTAAACATGGAAAGGA | L1HS\|chr4\|79704552\|79710582\|+\|4\|195 |
| (SEQ ID NO: 72) | AGGACATAGGCGTGGGCAAGCACTTCATGTC | L1HS\|chr4\|90675739\|90681758\|-\|12\|721 |
| (SEQ ID NO: 73) | ATTCAGGACATAGGCGTGGGCAAGCACTTCA | L1HS\|chr4\|90675739\|90681758\|-\|21\|231 |
| (SEQ ID NO: 74) | ATAGGCGTGGGCAAGCACTTCATGTCCAAAA | L1HS\|chr4\|90675739\|90681758\|-\|21\|234 |
| (SEQ ID NO: 75) | GGCGTGGGCAAGCACTTCATGTCCAAAACAC | L1HS\|chr4\|90675739\|90681758\|-\|21\|235 |
| (SEQ ID NO: 76) | TTCAGGACATAGGCGTGGGCAAGCACTTCAT | L1HS\|chr4\|90675739\|90681758\|-\|22\|171 |
| (SEQ ID NO: 77) | GCAAGCACTTCATGTCCAAAACACCAAAAGC | L1HS\|chr4\|90675739\|90681758\|-\|22\|177 |
| (SEQ ID NO: 78) | TAGGCGTGGGCAAGCACTTCATGTCCAAAAC | L1HS\|chr4\|90675739\|90681758\|-\|24\|81 |
| (SEQ ID NO: 79) | CTAAAAGAGCTCCTGAAGGAAGCACTAAACA | L1HS\|chr5\|123933969\|123935868\|+\|4\|193 |
| (SEQ ID NO: 80) | GTTACCCTCAAAGGAAAGCCCATCAGACTAA | L1HS\|chr5\|152076868\|152082892\|+\|8\|10 |
| (SEQ ID NO: 81) | AAAGAGCTCCTGAAGGAAGCACTAAACATGG | L1HS\|chr6\|117102131\|117108164\|+\|3\|223 |
| (SEQ ID NO: 82) | CCAGATTCATAAAGCAAGTCCTCAGTCACCT | L1HS\|chr6\|70010347\|70016553\|+\|10\|24 |
| (SEQ ID NO: 83) | GATTCATAAAGCAAGTCCTCAGTCACCTACA | L1HS\|chr6\|70010347\|70016553\|+\|10\|25 |
| (SEQ ID NO: 84) | AGATTCATAAAGCAAGTCCTCAGTCACCTAC | L1HS\|chr6\|70010347\|70016553\|+\|9\|122 |
| (SEQ ID NO: 85) | TAAAGCAAGTCCTCAGTCACCTACAAAGAGA | L1HS\|chr6\|70010347\|70016553\|+\|9\|125 |
| (SEQ ID NO: 86) | AAGTCCTCAGTCACCTACAAAGAGACTTAGA | L1HS\|chr6\|70010347\|70016553\|+\|9\|127 |
| (SEQ ID NO: 87) | AGATTCATAAAGCAAGTCCTCAATGACCTAC | L1HS\|chr7\|141920659\|141926713\|-\|10\|24 |
| (SEQ ID NO: 88) | GATTCATAAAGCAAGTCCTCAATGACCTACA | L1HS\|chr7\|141920659\|141926713\|-\|10\|25 |
| (SEQ ID NO: 89) | ATACAGAGAAGTGCTTAAAGGAGCTGATGGA | L1HS\|chr7\|145561496\|145564596\|+\|2\|53 |
| (SEQ ID NO: 90) | CTCCTGAAGGAAGCGGTAAACATGGAAAGGA | L1HS\|chr7\|30439242\|30445275\|+\|4\|195 |
| (SEQ ID NO: 91) | AAGAGCTCCTGAAGGAAGCGGTAAACATGGA | L1HS\|chr7\|30439242\|30445275\|+\|8\|85 |
| (SEQ ID NO: 92) | GATCAAGTGGAAGAAAGGGTATCAGCAATGG | L1HS\|chr7\|8351723\|8353976\|+\|1\|21 |
| (SEQ ID NO: 93) | ATCAAGTGGAAGAAAGGGTATCAGCAATGGA | L1HS\|chr7\|8351723\|8353976\|+\|1\|22 |
| (SEQ ID NO: 94) | CAAGTGGAAGAAAGGGTATCAGCAATGGAAG | L1HS\|chr7\|8351723\|8353976\|+\|1\|23 |
| (SEQ ID NO: 95) | AAAGAGCTCCTGAAGGAAGCAGTAAACATGG | L1HS\|chr8\|122296510\|122298300\|-\|1\|164 |
| (SEQ ID NO: 96) | AATATTTATGCACCCAATACAGGAGCACTCA | L1HS\|chr8\|75621331\|75627356\|-\|7\|112 |
| (SEQ ID NO: 97) | CGTCTGACTGGTGTACCTGAAAGTGATGTGG | L1HS\|chr8\|8470859\|8476907\|+\|1\|38 |
| (SEQ ID NO: 98) | TTACCCTCAAAGGAAAGCCCATCAGACTAAC | L1HS\|chr8\|91522091\|91528122\|-\|2\|227 |
| (SEQ ID NO: 99) | CTGCCCTAAAAGAGCTCCTGAAGGAAGCGCT | L1HS\|chr8\|91522091\|91528122\|-\|2\|298 |
| (SEQ ID NO: 100) | CCCTAAAAGAGCTCCTGAAGGAAGCGCTAAA | L1HS\|chr8\|91522091\|91528122\|-\|5\|192 |
| (SEQ ID NO: 101) | AGAATAACCAATACAGAGAAGTGCTTAAAGG | L1HS\|chrX\|149178166\|149184186\|-\|1\|78 |
| (SEQ ID NO: 102) | GAATAACCAATACAGAGAAGTGOTTAAAGGA | L1HS\|chrX\|149178166\|149184186\|-\|1\|79 |
| (SEQ ID NO: 103) | AATACAGAGAAGTGCTTAAAGGAGCTGATGG | L1HS\|chrX\|149178166\|149184186\|-\|1\|82 |

TABLE 2-continued

| Example L1HS probes | | |
|---|---|---|
| (SEQ ID NO: 104) | AAGTGCTTAAAGGAGCTGATGGAGCTGAAAA | L1HS\|chrX\|149178166\|149184186\|-\|1\|84 |
| (SEQ ID NO: 105) | AGTGCTTAAAGGAGCTGATGGAGCTGAAAAC | L1HS\|chrX\|149178166\|149184186\|-\|1\|85 |
| (SEQ ID NO: 106) | TACTTCATGTCCAAAACACCAAAAGCAATGG | L1HS\|chrX\|54118685\|54124745\|-\|14\|721 |
| (SEQ ID NO: 107) | ATATATATGCACCCAATACAGGAGCACTCAG | L1HS\|chrX\|91332922\|91336076\|-\|3\|113 |
| (SEQ ID NO: 108) | GCCCTAAAAGAGCTCCTGAAGGAAGCGCTAA | L1HS\|chrY\|3443550\|3449566\|+\|2\|191 |

TABLE 3

| Example MHC Presentation Pathway Probes | | |
|---|---|---|
| (SEQ ID NO: 109) | TCTTTTCTCTTTGATGTAAAAGTCTTTGATC | ERAP2 |
| (SEQ ID NO: 110) | GCGGAAACCCCGACTCAAATACAGGAAATGT | ERAP2 |
| (SEQ ID NO: 111) | CATACCATTTGGTTTAAGCCTTACATTCATG | ERAP2 |
| (SEQ ID NO: 112) | TTCCAAATGAATGGTCTCTGGTCAAATGAAT | ERAP2 |
| (SEQ ID NO: 113) | TCTTGCCCCAAATATGCATTTGTTCTCAGTT | ERAP2 |
| (SEQ ID NO: 114) | GAAGACCCTGAATGGAGGGCCCTGCAGGAGA | ERAP2 |
| (SEQ ID NO: 115) | TGGCAGGTGCCTGTAGTCCCAGCTACTCGGC | ERAP2 |
| (SEQ ID NO: 116) | ATACCTTGTAGCCTACATAGTTTGTGATTTC | ERAP2 |
| (SEQ ID NO: 117) | AAGCAGCCCCGCACTTCTCGAAGGTCTGAGT | ERAP2 |
| (SEQ ID NO: 118) | TTCTTTTGTATTGTTATTTACAATATTGTTA | ERAP2 |
| (SEQ ID NO: 119) | TCTTCCTTGCTCCATGCCCAGGGGCTGACTT | ERAP1 |
| (SEQ ID NO: 120) | ATGGATCAAATTTAATGTGGGCATGAATGGC | ERAP1 |
| (SEQ ID NO: 121) | TTCCCCTAATAACCATCACAGTGAGGGGGAG | ERAP1 |
| (SEQ ID NO: 122) | TAGGGAGGTGATTTTTTTTCTCTCTCTGCTT | ERAP1 |
| (SEQ ID NO: 123) | TCGGGCCGAAGCGCCGCTCAGCGCCAGCCTG | ERAP1 |
| (SEQ ID NO: 124) | CTTTCTCAACATTATTGTATTTTCCACTTAT | ERAP1 |
| (SEQ ID NO: 125) | CCAGAGCACTGAAGCATCTCCAAAACGTAGT | ERAP1 |
| (SEQ ID NO: 126) | GTTTTGGTCACCTGAGGAACCTATCTTTGTT | ERAP1 |
| (SEQ ID NO: 127) | CTCTGTTGCTGACTTGATTCAAGTTGCAGCG | ERAP1 |
| (SEQ ID NO: 128) | TACTATTGCTTGTATATTGTGGTATACGGTG | ERAP1 |
| (SEQ ID NO: 129) | AGTGGGCAGTTTCTTGTGCAGATTTGCCTTT | TAP2 |
| (SEQ ID NO: 130) | TAAAGGAAAGTATGAATGGAGAGGGGAAAGC | TAP2 |
| (SEQ ID NO: 131) | CTGCAGACAGTTCAGCGCGCCCACCAGATCC | TAP2 |
| (SEQ ID NO: 132) | AAATAATGCAACAGTCAAACCTAATTTTACA | TAP2 |
| (SEQ ID NO: 133) | GATGAGGAAACTGAAGCTCAAAGAGGCTCAA | TAP2 |
| (SEQ ID NO: 134) | TGCTCCAGAGTTCTTTTTGTTCACTCCTACC | TAP2 |
| (SEQ ID NO: 135) | CTTTCTTTCATCCTGGGGCTGACTTGCAGCT | TAP2 |
| (SEQ ID NO: 136) | AGCTTTGCATAAAACTCCTCAAAAGAGTTGC | TAP2 |
| (SEQ ID NO: 137) | TAATTTTACAGAGAAACTGACATGAAATCAC | TAP2 |
| (SEQ ID NO: 138) | TGATGCCATCTAATGGTCCCAGAAGAAACTG | TAP2 |

TABLE 3-continued

| Example MHC Presentation Pathway Probes | | |
|---|---|---|
| (SEQ ID NO: 139) | CCCGCTACATCGCCGTGGAGTACGTAGACGA | HLA-F |
| (SEQ ID NO: 140) | ATAAATTTTAAAAATAAAGAATAAAAATATA | HLA-F |
| (SEQ ID NO: 141) | AAATGGGCTATTTAGAGTGTTACCTCTCACT | HLA-F |
| (SEQ ID NO: 142) | AGGTCCTGTTTTTGTTCTACCCCAATCACTG | HLA-F |
| (SEQ ID NO: 143) | TCAGCGGAAACTTGATGATAACATGGTGGTC | HLA-F |
| (SEQ ID NO: 144) | ATGCAAGTCACCTTTCTAAGTCCCAGACAGC | HLA-F |
| (SEQ ID NO: 145) | TGACTTTATAGAAGCCAACTTCAGTTTGAAC | HLA-F |
| (SEQ ID NO: 146) | AACAGATAATTATCCAGCCCCAATACCAAGA | HLA-F |
| (SEQ ID NO: 147) | AAGGAGGCTGATCCCTGAGATTGTTGGGATA | HLA-F |
| (SEQ ID NO: 148) | GCACCATCTTATGAAAAGGGTCCAGATTAAG | HLA-F |
| (SEQ ID NO: 149) | TCTGCGGACGCTGCGCGGCTACTACAATCAG | HLA-E |
| (SEQ ID NO: 150) | CACCTTCCCAGGCTGATCTGAGGTAAACTTT | HLA-E |
| (SEQ ID NO: 151) | GTGGAAAAGGAGGGAGCTACTCTAAGGCTGA | HLA-E |
| (SEQ ID NO: 152) | CACACCCTGCAGTGGATGCATGGCTGCGAGC | HLA-E |
| (SEQ ID NO: 153) | AGAGAGCCTCCACTAGAGTGATGCTAAGTGG | HLA-E |
| (SEQ ID NO: 154) | TCCGAGGATGGTGCCGCGGGCGCCGTGGATG | HLA-E |
| (SEQ ID NO: 155) | CGGGTCTCACACCCTGCAGTGGATGCATGGC | HLA-E |
| (SEQ ID NO: 156) | TCATTCCCCTCACCTTCCCAGGCTGATCTGA | HLA-E |
| (SEQ ID NO: 157) | GGTGACAGGGTGAAACGCCATCTCAAAAAAT | HLA-E |
| (SEQ ID NO: 158) | GATGGAAACGGCCTCTACCGGGAGTAGAGAG | HLA-E |
| (SEQ ID NO: 159) | CTACTTCATGATCTCCAGCCTTCCTAATAAA | TAP1 |
| (SEQ ID NO: 160) | TCGAAACTTAACTCTCATGTCCATTCTCACC | TAP1 |
| (SEQ ID NO: 161) | AAGGCTGTGGGCTCCTCAGAGAAAATATTTG | TAP1 |
| (SEQ ID NO: 162) | TGCTGGTGCCCACCGCGCTGCCACTGCTCCG | TAP1 |
| (SEQ ID NO: 163) | TGCAGGCATGAGCCACTGCGCCCGACTGGTT | TAP1 |
| (SEQ ID NO: 164) | CCGCTACCTGCACAGGCAGGTGGCTGCAGTG | TAP1 |
| (SEQ ID NO: 165) | GCGTCGGCTTCTAGGCTGCCTGGGCTCGGAG | TAP1 |
| (SEQ ID NO: 166) | AGTCCCTTTTTTTGTGGTCTCTTTATAGATT | TAP1 |
| (SEQ ID NO: 167) | GAAGCCAACTATGGAGGAAATCACAGCTGCT | TAP1 |
| (SEQ ID NO: 168) | TCGGGAGCCTCTGGGTGCCCGGCGGTCAGGG | TAP1 |
| (SEQ ID NO: 169) | GAATGGAGAATGGCATGAGTTTTCCTGAGTT | HLA-B |
| (SEQ ID NO: 170) | AGGAGCGAGGGGACCGCAGGCGGGGGCGCAG | HLA-B |
| (SEQ ID NO: 171) | ATTTTCTGACTCTTCCCATCAGACCCCCCAA | HLA-B |
| (SEQ ID NO: 172) | CAGCGCTAGAATGTCGCCCTCCGTTGAATGG | HLA-B |
| (SEQ ID NO: 173) | GTGTAGGAGGAAGAGTTCAGGTGGAAAAGGA | HLA-B |
| (SEQ ID NO: 174) | CATGGGTGGTCCTAGGGTGTCCCATGAAAGA | HLA-B |
| (SEQ ID NO: 175) | CTCAGAGACTCGAACTTTCCAATGAATAGGA | HLA-B |
| (SEQ ID NO: 176) | GCAGCGGGATGGCGAGGACCAAACTCAGGAC | HLA-B |
| (SEQ ID NO: 177) | GACGTCTCTGAGGAAATGGAGGGGAAGACAG | HLA-B |

TABLE 3-continued

| Example MHC Presentation Pathway Probes | | |
|---|---|---|
| (SEQ ID NO: 178) | GCCCTCACAGGACATTTTCTTCCCACAGGTG | HLA-B |
| (SEQ ID NO: 179) | CTGAGGACTATTTATAGACAGCTCTAACATG | B2M |
| (SEQ ID NO: 180) | CAGAGTAACATTTTAGCAGGGAAAGAAGAAT | B2M |
| (SEQ ID NO: 181) | GACCAAAACATCATATCAGCATTTTTTCTTC | B2M |
| (SEQ ID NO: 182) | AGCTCTGCAGACATCCCATTCCTGTATGGGG | B2M |
| (SEQ ID NO: 183) | TGGTATTGCAGGATAAAGGCAGGTGGTTACC | B2M |
| (SEQ ID NO: 184) | CTCCAGAGAAAGGCTCTTAAAAATGCAGCGC | B2M |
| (SEQ ID NO: 185) | AGCCGACATTGAAGTTGACTTACTGAAGAAT | B2M |
| (SEQ ID NO: 186) | GGGTGTTTCTAGAGAGATATATCTGGTCAAG | B2M |
| (SEQ ID NO: 187) | AGGAATCTGATGCTCAAAGAAGTTAAATGGC | B2M |
| (SEQ ID NO: 188) | TTAAGATAGTTAAGCGTGCATAAGTTAACTT | B2M |
| (SEQ ID NO: 189) | TAGAAGTGTGCCCCGCCTTGTTACTGGAAGC | HLA-C |
| (SEQ ID NO: 190) | GCGGAGCAGCTGAGAGCCTACCTGGAGGGCA | HLA-C |
| (SEQ ID NO: 191) | GGGAAGCGGCCTCTGCGGAGAGGAGCGAGGG | HLA-C |
| (SEQ ID NO: 192) | CCCGGCCCGGCCGCGGAGTATTGGGACCGGG | HLA-C |
| (SEQ ID NO: 193) | TTCTTGTCCCACTGGGAGTTTCAAGCCCCAG | HLA-C |
| (SEQ ID NO: 194) | GACCGCGGGGGCGGGGCCAGGGTCTCACACC | HLA-C |
| (SEQ ID NO: 195) | CCCTGAGCTGGGAGCCATCTTCCCAGCCCAC | HLA-C |
| (SEQ ID NO: 196) | CGCCCAGAGTCTCCCCGTCTGAGATCCACCC | HLA-C |
| (SEQ ID NO: 197) | AGGAAGAGCTCAGGTGGAAAAGGAGGGAGCT | HLA-C |
| (SEQ ID NO: 198) | GCAAAGGCACCTGAATGTGTCTGCGTTCCTG | HLA-C |
| (SEQ ID NO: 199) | ACTGAGAGGCAAGAGTTGTTCCTGCCCTTCC | HLA-A |
| (SEQ ID NO: 200) | AGTTTCTTTTCTCCCTCTCCCAACCTACGTA | HLA-A |
| (SEQ ID NO: 201) | ACTCTCGGGGGCCCTGGCCCTGACCCAGACC | HLA-A |
| (SEQ ID NO: 202) | GGGCCAGGTTCTCACACCATCCAGATAATGT | HLA-A |
| (SEQ ID NO: 203) | CGTCCACAATCATGGGCCTACCCAGTCTGGG | HLA-A |
| (SEQ ID NO: 204) | CGCTGTTCTAAAGCCCGCACGCACCCACCGG | HLA-A |
| (SEQ ID NO: 205) | GAAGGCCCAGTCACAGACTGACCGAGTGGAC | HLA-A |
| (SEQ ID NO: 206) | TCCAGGACCCACACCTGCTTTCTTCATGTTT | HLA-A |
| (SEQ ID NO: 207) | GGAAGAGCTCAGATAGAAAAGGAGGGAGTTA | HLA-A |
| (SEQ ID NO: 208) | ATGAGAAGGATGGAGGGAAGGGCTGGAGAAG | HLA-A |

TABLE 4

| Example APOBEC probes | | |
|---|---|---|
| (SEQ ID NO: 6) | TCGCCTCCTAAAGTGCTGGGATTACAGGCGT | Synthetically Mutated Kmer |
| (SEQ ID NO: 7) | GATCTCTTGACCTCGTGATCCACCCTCCTTG | Synthetically Mutated Kmer |
| (SEQ ID NO: 8) | CCTCTGCCTCCTGGGTTTGAGCAATTCTCCT | Synthetically Mutated Kmer |
| (SEQ ID NO: 9) | AAGTGCTAGGATTACAGGCGTGAGCCTCTGC | Synthetically Mutated Kmer |
| (SEQ ID NO: 10) | CTAACAGTGAAACCCTGTCTCTACTAAAAAT | Synthetically Mutated Kmer |

TABLE 4-continued

| Example APOBEC probes | | |
|---|---|---|
| (SEQ ID NO: 209) | GTATTTTGAGTAGAGATGGGGTTTCACTGTG | Synthetically Mutated Kmer |
| (SEQ ID NO: 210) | TGTATTTTGAGTAGAGATGGGGTTTCACTGT | Synthetically Mutated Kmer |
| (SEQ ID NO: 211) | TTGTATTTTGAGTAGAGATGGGGTTTCACTG | Synthetically Mutated Kmer |
| (SEQ ID NO: 212) | TCCTGGGCCCAAGCGATCCTCCTACCTCAGC | Synthetically Mutated Kmer |
| (SEQ ID NO: 213) | GCCTCCTAAGTAGCTGGGATTACAGACGTGT | Synthetically Mutated Kmer |
| (SEQ ID NO: 214) | ACTCCTGGGCTCAAGTGATCCTCTTACCTTG | Synthetically Mutated Kmer |
| (SEQ ID NO: 215) | CCTGGGCCCAAGCGATCCTCCTACCTCAGCC | Synthetically Mutated Kmer |
| (SEQ ID NO: 216) | CCGCCATTGCCGCAGATCCAGCGCCCAGAGA | Synthetically Mutated Kmer |
| (SEQ ID NO: 217) | AACCTCTGCCTCCTGGGTTTGAGCAATTCTC | Synthetically Mutated Kmer |
| (SEQ ID NO: 218) | CTTTCTCTAAAAGGTATTTGAAATATCTCAC | Synthetically Mutated Kmer |
| (SEQ ID NO: 219) | CTCCTGGGCCCAAGCGATCCTCCTACCTCAG | Synthetically Mutated Kmer |
| (SEQ ID NO: 220) | GGGATTACAGGCATGCACCACTACGCCTGGC | Synthetically Mutated Kmer |
| (SEQ ID NO: 221) | GAGTCTCACTCTGTCACTAGGCTGGAGTGCA | Synthetically Mutated Kmer |
| (SEQ ID NO: 222) | CGCCATTGCCGCAGATCCAGCGCCCAGAGAG | Synthetically Mutated Kmer |
| (SEQ ID NO: 223) | GCCGCTTCTAGACCATGGAGGAGAAGAAAGC | Synthetically Mutated Kmer |
| (SEQ ID NO: 224) | CAAAAGGGTCATTATCTCTGCCCCCTCTGCT | Synthetically Mutated Kmer |
| (SEQ ID NO: 225) | CCTCAGCCTCCTAAGTAACTGGGACTACAGG | Synthetically Mutated Kmer |
| (SEQ ID NO: 226) | CAGCCTCCCTAGTAGCTGGGACTACAGGCGT | Synthetically Mutated Kmer |
| (SEQ ID NO: 227 | CCACGCCATTCTCCTGCCTCAGCCTCCCTAG | Synthetically Mutated Kmer |
| (SEQ ID NO: 228) | GGCCATGGCCGCTTCTAGACCATGGAGGAGA | Synthetically Mutated Kmer |
| (SEQ ID NO: 229) | GCCATGGCCGCTTCTAGACCATGGAGGAGAA | Synthetically Mutated Kmer |
| (SEQ ID NO: 230) | TGTGCGGGGCGCCCTCTGCCACGCAGCCGGC | Synthetically Mutated Kmer |
| (SEQ ID NO: 231) | CGACCTCAGGTGATCCTCCTGCCTCGGCCTC | Synthetically Mutated Kmer |
| (SEQ ID NO: 232) | CCATGGCCGCTTCTAGACCATGGAGGAGAAG | Synthetically Mutated Kmer |
| (SEQ ID NO: 233) | AGGAGAAGATGTGGAGACTTCTAAGAAATGG | Synthetically Mutated Kmer |
| (SEQ ID NO: 234) | CCTCCTGAGTAGCTGGGATTACAGGCGCCTA | Synthetically Mutated Kmer |
| (SEQ ID NO: 235) | TGCCTCAGCCTCCTAAGTAACTGGGACTACA | Synthetically Mutated Kmer |
| (SEQ ID NO: 236) | CGTGCAGGTACCATTAGGAAGCAGCGGGATA | Synthetically Mutated Kmer |
| (SEQ ID NO: 237) | GTGCAGGTACCATTAGGAAGCAGCGGGATAA | Synthetically Mutated Kmer |
| (SEQ ID NO: 238) | TGCAGGTACCATTAGGAAGCAGCGGGATAAG | Synthetically Mutated Kmer |
| (SEQ ID NO: 239) | TTCAAGTGATTCTCCTGCCTCAGTCTCCTGA | Synthetically Mutated Kmer |
| (SEQ ID NO: 240) | GGGAAGCTGAAAGTCCCTGAATGGGTGGATA | Synthetically Mutated Kmer |
| (SEQ ID NO: 241) | TCCGCCTCCTGGTTCAAGCAATTCTCCTGCC | Synthetically Mutated Kmer |
| (SEQ ID NO: 242) | CGCCCGCCACTACGCCCGGCTAATTTTTTTT | Synthetically Mutated Kmer |
| (SEQ ID NO: 243) | CAAGTGATTCTCCTGCCTCAGTCTCCTGAGT | Synthetically Mutated Kmer |
| (SEQ ID NO: 244) | TGCTGGGATTGCAGGCATGAGCCACTGCGCC | Synthetically Mutated Kmer |
| (SEQ ID NO: 245) | AAAGGGTCATTATCTCTGCCCCCTCTGCTGA | Synthetically Mutated Kmer |
| (SEQ ID NO: 246) | CCATTGCCGCAGATCCAGCGCCCAGAGAGAC | Synthetically Mutated Kmer |
| (SEQ ID NO: 247) | AAAAGGGTCATTATCTCTGCCCCCTCTGCTG | Synthetically Mutated Kmer |

TABLE 4-continued

| Example APOBEC probes | | |
|---|---|---|
| (SEQ ID NO: 248) | CGGGAAGCTGAAAGTCCCTGAATGGGTGGAT | Synthetically Mutated Kmer |
| (SEQ ID NO: 249) | GGATTGGTTATTACTCTTCTGTGATGCCTGC | Synthetically Mutated Kmer |
| (SEQ ID NO: 250) | ATTGGTTATTACTCTTCTGTGATGCCTGCTT | Synthetically Mutated Kmer |
| (SEQ ID NO: 251) | GATTGGTTATTACTCTTCTGTGATGCCTGCT | Synthetically Mutated Kmer |
| (SEQ ID NO: 252) | TCAAGTGATTCTCCTGCCTCAGTCTCCTGAG | Synthetically Mutated Kmer |
| (SEQ ID NO: 253) | CGTTTCTAGATGAGAATTCACAAGCGACTCA | Synthetically Mutated Kmer |
| (SEQ ID NO: 254) | TTGGCCATGGCCGCTTCTAGACCATGGAGGA | Synthetically Mutated Kmer |
| (SEQ ID NO: 255) | TGGCCATGGCCGCTTCTAGACCATGGAGGAG | Synthetically Mutated Kmer |
| (SEQ ID NO: 256) | CCTCCTGGGCCCAAGCGATCCTCCTACCTCA | Synthetically Mutated Kmer |
| (SEQ ID NO: 257) | ATTAACTCGAGCCTTTAGTTTTTATCCATGT | Synthetically Mutated Kmer |
| (SEQ ID NO: 258) | CAGCCTCCTGAGCAGCTGGGACTACAGGCGC | Synthetically Mutated Kmer |
| (SEQ ID NO: 259) | GCCATTGCCGCAGATCCAGCGCCCAGAGAGA | Synthetically Mutated Kmer |
| (SEQ ID NO: 260) | TTTGGCCATGGCCGCTTCTAGACCATGGAGG | Synthetically Mutated Kmer |
| (SEQ ID NO: 261) | AAGTGATTCTCCTGCCTCAGTCTCCTGAGTA | Synthetically Mutated Kmer |
| (SEQ ID NO: 262) | CTGCCGCCATTGCCGCAGATCCAGCGCCCAG | Synthetically Mutated Kmer |
| (SEQ ID NO: 263) | CCATTAAGCCAGATGTCAGAAGCTACACCAT | Synthetically Mutated Kmer |
| (SEQ ID NO: 264) | TGCCGCCATTGCCGCAGATCCAGCGCCCAGA | Synthetically Mutated Kmer |
| (SEQ ID NO: 265) | ATGTGCGGGGCGCCCTCTGCCACGCAGCCGG | Synthetically Mutated Kmer |
| (SEQ ID NO: 266) | GAGGAGAAGATGTGGAGACTTCTAAGAAATG | Synthetically Mutated Kmer |
| (SEQ ID NO: 267) | CGGCCTCCTAGAGTGCTGGGATTACAGGCCT | Synthetically Mutated Kmer |
| (SEQ ID NO: 268) | CTCCGCCTCCTGGTTCAAGCAATTCTCCTGC | Synthetically Mutated Kmer |
| (SEQ ID NO: 269) | TTTGTTCAAGTCTCTCTGTGTCCGGGGTGAG | Synthetically Mutated Kmer |
| (SEQ ID NO: 270) | TTGTTCAAGTCTCTCTGTGTCCGGGGTGAGC | Synthetically Mutated Kmer |
| (SEQ ID NO: 271) | GTTTGTTCAAGTCTCTCTGTGTCCGGGGTGA | Synthetically Mutated Kmer |
| (SEQ ID NO: 272) | TTTTAGTAGAGACAGGGCTTCACTATGTTGG | Synthetically Mutated Kmer |
| (SEQ ID NO: 273) | AGAGAAAGGGTTTCACTATGTTGGCCAGGCT | Synthetically Mutated Kmer |
| (SEQ ID NO: 274) | AGCCTTCTGAGTAGCTGGGATTACAGGCACC | Synthetically Mutated Kmer |
| (SEQ ID NO: 275) | ACGTGCAGGTACCATTAGGAAGCAGCGGGAT | Synthetically Mutated Kmer |
| (SEQ ID NO: 276) | GACGTGCAGGTACCATTAGGAAGCAGCGGGA | Synthetically Mutated Kmer |
| (SEQ ID NO: 277) | CCGGGAAGCTGAAAGTCCCTGAATGGGTGGA | Synthetically Mutated Kmer |
| (SEQ ID NO: 278) | TTTAGTAGAGACAGGGCTTCACTATGTTGGC | Synthetically Mutated Kmer |
| (SEQ ID NO: 279) | TGCCTCAGCCTCCTTAGTAGCTGAGATTACA | Synthetically Mutated Kmer |
| (SEQ ID NO: 280) | ATGATGTGCGGGGCGCCCTCTGCCACGCAGC | Synthetically Mutated Kmer |
| (SEQ ID NO: 281) | GCTTCAGTCAACTTCTTAGAGTTTTCTAAGA | Synthetically Mutated Kmer |
| (SEQ ID NO: 282) | GTGTTTGTTCAAGTCTCTCTGTGTCCGGGGT | Synthetically Mutated Kmer |
| (SEQ ID NO: 283) | AGTGTTTGTTCAAGTCTCTCTGTGTCCGGGG | Synthetically Mutated Kmer |
| (SEQ ID NO: 284) | TGTTTGTTCAAGTCTCTCTGTGTCCGGGGTG | Synthetically Mutated Kmer |
| (SEQ ID NO: 285) | TAGTGTTTGTTCAAGTCTCTCTGTGTCCGGG | Synthetically Mutated Kmer |
| (SEQ ID NO: 286) | CTAGTGTTTGTTCAAGTCTCTCTGTGTCCGG | Synthetically Mutated Kmer |

TABLE 4-continued

| Example APOBEC probes | | |
|---|---|---|
| (SEQ ID NO: 287) | CTGCCTCAGCCTCCTGAGCAGCTGGGACTAC | Synthetically Mutated Kmer |
| (SEQ ID NO: 288) | GCTAGTGTTTGTTCAAGTCTCTCTGTGTCCG | Synthetically Mutated Kmer |
| (SEQ ID NO: 289) | CGAGGTGCCTTTCTCTAAAAGGTATTTGAAA | Synthetically Mutated Kmer |
| (SEQ ID NO: 290) | GAGGTGGGGTTTCACTATGTTGGCCAGGCTG | Synthetically Mutated Kmer |
| (SEQ ID NO: 291) | GCCTCCTAGAGTGCTGGGATTACAGGCCTGA | Synthetically Mutated Kmer |
| (SEQ ID NO: 292) | TATGCTAGTGTTTGTTCAAGTCTCTCTGTGT | Synthetically Mutated Kmer |
| (SEQ ID NO: 293) | TGCTAGTGTTTGTTCAAGTCTCTCTGTGTCC | Synthetically Mutated Kmer |
| (SEQ ID NO: 294) | ATGCTAGTGTTTGTTCAAGTCTCTCTGTGTC | Synthetically Mutated Kmer |
| (SEQ ID NO: 295) | TTAGTAGAGACGGAGTTTCACTGTGTTAGCC | Synthetically Mutated Kmer |
| (SEQ ID NO: 296) | CCAAAAGGGTCATTATCTCTGCCCCCTCTGC | Synthetically Mutated Kmer |
| (SEQ ID NO: 297) | CTGGGCCCAAGCGATCCTCCTACCTCAGCCT | Synthetically Mutated Kmer |
| (SEQ ID NO: 298) | TTACAGGCGTGAGCCACTGTGCCCAGCCATA | Synthetically Mutated Kmer |
| (SEQ ID NO: 299) | AAACTTTCCTTAAAGTTCTTATTGCCTTTGC | Synthetically Mutated Kmer |
| (SEQ ID NO: 300) | AACTTTCCTTAAAGTTCTTATTGCCTTTGCA | Synthetically Mutated Kmer |
| (SEQ ID NO: 301) | ACTTTCCTTAAAGTTCTTATTGCCTTTGCAC | Synthetically Mutated Kmer |
| (SEQ ID NO: 302) | GCCAAAAGGGTCATTATCTCTGCCCCCTCTG | Synthetically Mutated Kmer |
| (SEQ ID NO: 303) | CTTTCCTTAAAGTTCTTATTGCCTTTGCACT | Synthetically Mutated Kmer |

What is claimed is:

1. A method for identifying antigenic peptides for use in cancer treatment, the method comprising:

identifying a group of candidate cancer antigens that are generated from transposable elements;

determining a baseline expression level for each of the candidate cancer antigens using measurements of healthy tissue from a first cohort of healthy subjects;

determining a tumor expression level for each of the candidate cancer antigens using measurements of tumor tissue from a second cohort of cancer subjects;

determining a differential expression level for each of the candidate cancer antigens using the baseline expression levels and the tumor expression levels; and selecting one or more of the candidate cancer antigens having the differential expression level greater than a threshold, where the one or more candidate cancer antigens are identified as one or more antigenic peptides.

2. The method of claim 1, wherein identifying the group of candidate cancer antigens that are generated from the transposable elements includes identifying a set of kmers.

3. The method of claim 2, wherein selecting one or more of the candidate cancer antigens includes mapping the set of kmers to the one or more of the candidate cancer antigens.

4. The method of claim 1, wherein determining the tumor expression level comprises using mass spectrometry data from peptides eluted from MHC.

5. The method of claim 1, wherein determining the tumor expression level comprises using tumor RNA expression data.

6. The method of claim 5, where the tumor RNA expression data is obtained from RNA sequencing of samples.

7. The method of claim 1, wherein the one or more of the candidate cancer antigens are further selected based on one or more other criteria.

8. The method of claim 7, wherein the one or more other criteria include a water solubility of the one or more of the candidate cancer antigens or binding to a particular MHC haplotype.

9. The method of claim 1, wherein the baseline expression level is measured for different cohorts, each sharing one or more MHC alleles.

10. The method of claim 1, wherein the baseline expression level is measured for a particular tissue type.

11. The method of claim 1, wherein the transposable elements include L1HS.

12. A method of identifying a cancer vaccine for a patient, the method comprising:

identifying a group of candidate cancer antigens that are generated from transposable elements;

determining a baseline expression level for each of the candidate cancer antigens, the baseline expression levels determined using measurements of healthy tissue from healthy subjects;

determining a tumor expression level for each of the candidate cancer antigens using measurements of tumor tissue from the patient;

determining a differential expression level for each of the candidate cancer antigens using the baseline expression levels and the tumor expression levels;

selecting one or more of the candidate cancer antigens having the differential expression level greater than a threshold; and selecting, as the cancer vaccine, a peptide corresponding to the one or more of the candidate cancer antigens.

13. The method of claim 12, further comprising:

determining an expected efficacy of the cancer vaccine based on APOBEC activity in the tumor tissue.

14. The method of claim 12, wherein the tumor expression level for a candidate cancer antigen is measured by detecting RNA on a microarray using nucleic acid probes.

15. The method of claim 12, further comprising:

detecting an MHC haplotype of the patient, wherein the cancer vaccine is selected based on the MHC haplotype.

16. The method of claim 12, wherein the tumor expression level for a candidate cancer antigen is determined by measuring RNA expression.

17. The method of claim 16, wherein the RNA expression is measured by sequencing RNA molecules.

18. The method of claim 12, wherein the tumor expression level for a candidate cancer antigen is measured by analyzing proteins using mass spectrometry.

19. The method of claim 7, wherein the one or more other criteria comprise at least one criterion selected from the group consisting of:

(a) a water solubility of the one or more of the candidate cancer antigens, (b) an ability of the one or more of the candidate cancer antigens to be presented by an MHC or HLA allele of a cancer subject, (c) a distance between the one or more of the candidate cancer antigens and a corresponding closest normal protein antigen, (d) a hydrophobicity of the one or more of the candidate cancer antigens, and (e) an immunogenicity.

* * * * *